United States Patent
Yanagi et al.

(10) Patent No.: US 10,416,147 B2
(45) Date of Patent: Sep. 17, 2019

(54) METHOD OF MANUFACTURING MEMBRANE DEVICE, MEMBRANE DEVICE, AND NANOPORE DEVICE

(71) Applicant: Hitachi, Ltd., Chiyoda-ku, Tokyo (JP)

(72) Inventors: Itaru Yanagi, Tokyo (JP); Kenichi Takeda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/063,982

(22) PCT Filed: Mar. 18, 2016

(86) PCT No.: PCT/JP2016/058833
§ 371 (c)(1),
(2) Date: Jun. 19, 2018

(87) PCT Pub. No.: WO2017/158845
PCT Pub. Date: Sep. 21, 2017

(65) Prior Publication Data
US 2019/0004030 A1    Jan. 3, 2019

(51) Int. Cl.
*H01L 21/00* (2006.01)
*G01N 33/487* (2006.01)
(Continued)

(52) U.S. Cl.
CPC ... *G01N 33/48721* (2013.01); *B81C 1/00087* (2013.01); *B81B 2203/0353* (2013.01); *C12Q 1/6869* (2013.01)

(58) Field of Classification Search
CPC .................................................. B81C 1/00087
(Continued)

(56) References Cited

U.S. PATENT DOCUMENTS

| 6,619,133 B1 | 9/2003 | Goshoo et al. |
| 2005/0052724 A1 | 3/2005 | Suzuki et al. |

(Continued)

FOREIGN PATENT DOCUMENTS

| JP | 2000-171318 A | 6/2000 |
| JP | 2005-045463 A | 2/2005 |

(Continued)

OTHER PUBLICATIONS

Yanagi, I. et al. "Fabricating nanopores with diameters of sub-1 nm to 3 nm using multilevel pulse-voltage injection", Scientific Reports; May 21, 2014; vol. 4.

(Continued)

*Primary Examiner* — Ajay Arora
(74) *Attorney, Agent, or Firm* — Procopio, Cory, Hargreaves & Savitch LLP

(57) ABSTRACT

A method of manufacturing a membrane device comprises: a first step of forming a pillar structure on a part of a Si substrate by etching; a second step of forming a first insulation layer on the Si substrate so as to expose a Si surface of an upper part of the pillar structure; a third step of forming a second insulation layer on the pillar structure and the first insulation layer; and a fourth step of etching the Si substrate from an opposite side of the second insulation layer and etching the pillar structure with the first insulation layer being a mask, to thereby form a membrane, which is a region free of the pillar structure in the second insulation layer.

8 Claims, 42 Drawing Sheets

(51) Int. Cl.
*B81C 1/00* (2006.01)
*C12Q 1/6869* (2018.01)

(58) Field of Classification Search
USPC .......................................................... 438/106
See application file for complete search history.

(56) References Cited

U.S. PATENT DOCUMENTS

| | | |
|---|---|---|
| 2005/0070042 A1 | 3/2005 | Barth |
| 2005/0102721 A1 | 5/2005 | Barth |
| 2012/0037591 A1 | 2/2012 | Tringe et al. |
| 2014/0264651 A1* | 9/2014 | Dehe .................. B81C 1/00182 257/416 |
| 2014/0285224 A1 | 9/2014 | Albuschies |
| 2019/0023014 A1* | 1/2019 | Giusti .................. B41J 2/14233 |

FOREIGN PATENT DOCUMENTS

| | | |
|---|---|---|
| JP | 2005-125490 A | 5/2005 |
| JP | 2009-231324 A | 10/2009 |
| JP | 2014-531327 A | 11/2014 |

OTHER PUBLICATIONS

Kumar, A. et al. "Noise and its reduction in graphene based nanopore Devices", Nanotechnology 24; Nov. 15, 2013.

Yanagi, I. et al. "Fabrication of 3-nm-thick Si3N4 membranes for solid-state nanopores using the poly-Si sacrificial layer process", Scientific Reports; Oct. 1, 2015; vol. 5.

* cited by examiner

METHOD OF MANUFACTURING MEMBRANE DEVICE, MEMBRANE DEVICE, AND NANOPORE DEVICE

BACKGROUND OF THE INVENTION

This invention relates to a method of manufacturing a membrane device including a membrane, a membrane device, and a nanopore device having a nanopore formed in a membrane.

In order to implement a more advanced generation deoxyribonucleic acid (DNA) sequencer, a technology using a nanopore has been studied. Specifically, the technology using a nanopore involves forming a hole (nanopore) having a size comparable to that of DNA in a membrane. Further, the technology using a nanopore involves filling chambers on upper and lower sides of a thin film membrane with an aqueous solution and arranging electrodes so that the electrodes are brought into contact with the aqueous solutions in both the chambers.

The technology using a nanopore involves placing DNA to be measured in one of the chambers and applying a potential difference between the electrodes arranged in both the chambers, to thereby electrophorese the DNA. In the technology using a nanopore, a structural feature and a base sequence of the DNA are determined by measuring a change in time of an ion current flowing between the electrodes when the DNA passes through the nanopore. The technology using a nanopore is useful for acquiring structural features of various biological molecules as well as DNA.

A semiconductor substrate and a semiconductor material have high mechanical strength, and hence a nanopore device is manufactured through use of a semiconductor process. For example, in Yanagi, I., Akahori, R., Hatano, T. 86 Takeda, K. "Fabricating nanopores with diameters of sub-1 nm to nm using multilevel pulse-voltage injection" Sci. Rep. 4, 5000; DOI:10.1038/srep05000 (2014) (hereinafter referred to as "Non Patent Literature 1"), it is disclosed that a membrane is formed through use of a silicon nitride film (SiN film). Further, in Non Patent Literature 1, a fine pinhole is opened in the membrane by applying voltage stress to the membrane in an ion aqueous solution to cause puncture. The pinhole serves as a nanopore. The nanopore is also formed by etching the membrane with an aggregated electron beam.

As one of the important factors for determining DNA reading accuracy of the nanopore sequencer, there is given the thickness of the membrane. In other words, it is preferred that the thickness of the membrane be as small as possible. Each interval between adjacent bases of four kinds of bases (adenine (A), guanine (G), cytosine (C), and thymine (T)) arranged in a DNA strand is about 0.34 nanometer. As the thickness of the membrane becomes larger than the interval, a larger number of bases simultaneously enter the nanopore.

In this case, a signal obtained by current measurement is also a signal derived from a plurality of bases. Therefore, the determination accuracy of a base sequence is deteriorated, and signal analysis also becomes more complicated. Further, even when structural features of various biological molecules other than DNA are acquired, spatial resolution decreases as the thickness of the membrane becomes larger. Thus, in order to improve structure determination accuracy of an object to be measured, it is important to reduce the thickness of the membrane having a nanopore to the extent possible.

In order to reduce the thickness of the membrane, needless to say, it is preferred that a region (area) of the membrane be as narrow as possible. As the region of the membrane becomes narrower, there is a decreased probability that inevitable defects (a weak spot and a pinhole caused by, for example, a binding defect between atoms) occurring at a time of formation of the membrane are present in the membrane. Further, when the membrane is formed, it is important to avoid processes that may cause the membrane to be scraped or broken to the extent possible.

In Yanagi, I., Ishida, T., Fujisaki, K. 86 Takeda, K. "Fabrication of 3-nm-thick Si3N4 membranes for solid-state nanopores using the poly-Si sacrificial layer process" Sci. Rep. 5, 14656; doi: 10.1038/srep14656 (2015) (hereinafter referred to as "Non Patent Literature 2"), there is disclosed a method of forming a thin film SiN membrane. The forming method of Non Patent Literature 2 involves forming a thin SiN film (3 nanometers) on a Si substrate, forming a poly-Si film (150 nanometers) on the thin SiN film, and forming a SiN film (100 nanometers) on the poly-Si film. The forming method of Non Patent Literature 2 further involves opening a part of the upper SiN film, etching a rear surface of the Si substrate with a TMAH solution, and etching the poly-Si film with a KOH aqueous solution from the partially opened portion of the upper SiN film. With this, the thin film SiN membrane is formed.

The forming method of Non Patent Literature 2 does not use hydrofluoric acid at a time of forming the SiN membrane unlike Non Patent Literature 1. Therefore, in the forming method of Non Patent Literature 2, an ultrathin SiN membrane of about 3 nanometers can be formed. Further, in Non Patent Literature 2, it is disclosed that a nanopore is opened by irradiating the ultrathin SiN membrane of about 3 nanometers with an aggregated electron beam, and then a phenomenon in which DNA passes through the nanopore in an ion aqueous solution is measured based on a change in time of an ion current.

In Ashvani Kumar, Kyeong-Beom Park, Hyun-Mi Kim and Ki-Bum Kim. "Noise and its reduction in graphene based nanopore devices" Nanotechnology, 24, 495503 doi: 10.1088/0957-4484/24/49/495503 (2013) (hereinafter referred to as "Non Patent Literature 3"), as a method of reducing noise at a time of measuring an ion current flowing when the DNA passes through the nanopore, there is disclosed a method using a glass substrate. The method of Non Patent Literature 3 involves forming an amorphous Si (a-Si) film on a glass substrate, opening a part of the a-Si film by etching, opening a part of the glass substrate from a rear surface thereof, and forming a through hole so that the opened portions of the a-Si film and the glass substrate overlap each other.

The method of Non Patent Literature 3 further involves transferring by a fishing method a SiN film formed separately onto the glass substrate so as to close the opened portions and opening a pore in the SiN film. The method of Non Patent Literature 3 further involves transferring graphene onto the SiN film, forming a nanopore in the graphene, and measuring an ion current flowing when the DNA passes through the nanopore. Thus, noise at a time of ion current measurement is reduced through use of the glass substrate instead of the Si substrate.

In the forming method of Non Patent Literature 2, when the rear surface of the Si substrate is etched with the TMAH solution, one side of the thin SiN membrane (Si substrate rear surface side) is brought into contact with the TMAH solution. Further, when the poly-Si film is etched with the KOH aqueous solution from the partially opened portion of the upper SiN film, the other side of the thin SiN membrane (Si substrate upper surface side) is also brought into contact with the KOH aqueous solution. The TMAH solution and the KOH aqueous solution have characteristics of hardly etching SiN.

However, the etching amount of SiN is not completely zero. Therefore, the contact of the TMAH solution and the KOH aqueous solution with the SiN membrane damages the SiN membrane, although the damage may not be significant. In particular, when it is intended to form a thin film SiN membrane, a slight damage leads to defects of the membrane. Thus, it is required to minimize the number of times of contact of the solutions with the thin film SiN membrane at a time of wet etching.

Further, in the case of using the process of etching the poly-Si film with the KOH aqueous solution from the partially opened portion of the upper SiN film as disclosed in Non Patent Literature 2, a SiN membrane region larger than the partially opened region of the upper SiN film is formed. Actually, in Non Patent Literature 2, the partially opened region of the upper SiN film has a circular shape having a diameter of about 150 nanometers, whereas the SiN membrane region has a diameter of about 600 nanometers.

In consideration of variation in etching rate of wet etching and variation in thickness of the poly-Si film, it is not realistic that etching is stopped immediately after the SiN membrane region positioned under the poly-Si film is exposed. In other words, it is required to perform overetching in consideration of variation in etching rate of wet etching and variation in thickness of the poly-Si film. In this case, a SiN membrane region larger than the partially opened region of the upper SiN film is inevitably formed.

As described above, as the membrane region becomes narrower, there is a decreased probability that inevitable defects (a weak spot and a pinhole caused by, for example, a binding defect between atoms) occurring at a time of formation of the membrane are present in the membrane. The decreased probability is advantageous for forming the membrane. Therefore, enlargement of the SiN membrane region is disadvantageous for forming the membrane.

In Non Patent Literature 2, when an ion current flowing when the DNA passes through a nanopore is measured through use of a thin film membrane having the nanopore opened therein, noise at a time of current measurement increases. When noise at a time of current measurement is large, a current signal derived from an object to be measured becomes unclear, resulting in an increase in incorrect identification.

As one of the reasons that noise at a time of current measurement is large, there is given a large electrostatic capacitance of a structure that is sandwiched between aqueous solutions of upper and lower chambers and is formed of a membrane, a Si substrate, and a laminated film on the Si substrate. In general, as the ratio of an insulator having a low specific dielectric constant of the structure sandwiched between the aqueous solutions of the upper and lower chambers increases, the electrostatic capacitance of the structure sandwiched between the aqueous solutions of the upper and lower chambers decreases. As a result, noise at a time of measuring an ion current flowing when the DNA passes through the nanopore is reduced.

In Non Patent Literature 2, the poly-Si film is not an insulation film but a semiconductor. Therefore, only the ultrathin SiN membrane of about 3 nanometers, the upper SiN film of 100 nanometers, and the SiN film adhering to a part of the rear surface of the Si substrate are each formed of an insulation film. Under this condition, the electrostatic capacitance of the entire structure sandwiched between the aqueous solutions of the upper and lower chambers cannot be sufficiently decreased. As a result, noise at a time of measuring an ion current flowing when the DNA passes through the nanopore increases.

Further, when a SiN membrane is formed by the fishing method as in Non Patent Literature 3, the membrane is greatly damaged, and defects are liable to occur in the membrane. Further, for example, a foreign matter is liable to adhere to the membrane. Those problems cause peeling of the membrane from the a-Si film and noise at a time of measurement. Thus, stable formation of the membrane by the fishing method is difficult due to insufficient controllability. In particular, it is difficult to transfer the membrane to a wafer having a large diameter. Accordingly, it is difficult to apply the method of Non Patent Literature 3 to batch processing by a semiconductor process. In other words, the method of Non Patent Literature 3 is not suitable for formation and mass production of a membrane.

SUMMARY OF THE INVENTION

This invention has an object to manufacture a membrane device and a nanopore device, which are capable of suppressing breakage of a membrane, and includes a membrane having a low electrostatic capacitance.

An aspect of the invention disclosed in this application is a method of manufacturing a membrane device, comprising: a first step of forming a pillar structure on a part of a Si substrate by etching; a second step of forming a first insulation layer on the Si substrate so as to expose a Si surface of an upper part of the pillar structure; a third step of forming a second insulation layer on the pillar structure and the first insulation layer; and a fourth step of etching the Si substrate from an opposite side of the second insulation layer and etching the pillar structure with the first insulation layer being a mask, to thereby form a membrane, which is a region free of the pillar structure in the second insulation layer.

Another aspect of the invention disclosed in this application is a method of manufacturing a membrane device, comprising: a first step of forming a second insulation layer on a Si layer of a laminated substrate, the laminated substrate comprising a first insulation layer formed on a surface of a Si substrate and the Si layer formed on the first insulation layer, and forming a third insulation layer on a rear surface of the Si substrate; a second step of forming an opening in the third insulation layer so as to expose the rear surface of the Si substrate and etching the Si substrate with the third insulation layer being a mask; and a third step of etching the first insulation layer with the Si substrate being a mask and etching the Si layer with the first insulation layer being a mask, to thereby form a membrane, which is a region free of the Si layer in the second insulation layer.

An aspect of the invention disclosed in this application is a membrane device, comprising: a first Si layer having a first through hole; a first insulation layer having a second through hole, the second through hole having a pore diameter smaller than a pore diameter of the first through hole and communicating to the first through hole; a second Si layer formed on an outer peripheral edge of the second through hole; a second insulation layer formed on the second Si layer and the first insulation layer so as to close the second through hole; and a membrane, which is a part of the second insulation layer, and is a region for closing the second through hole.

An aspect of the invention disclosed in this application is a nanopore device, comprising: a first Si layer having a first through hole; a first insulation layer having a second through hole, the second through hole having a pore diameter smaller than a pore diameter of the first through hole and communicating to the first through hole; and a second Si layer formed on an outer peripheral edge of the second through hole, wherein an inner peripheral surface of the second Si layer having the second through hole has a {111} plane exposed thereon, wherein a surface of the second Si layer on an opposite side of the first through hole has a {100} plane exposed thereon, and wherein the second Si layer has a pore formed of the second through hole on the surface.

According to the representative embodiments of this invention, it is possible to manufacture the membrane device and the nanopore device, which are capable of suppressing breakage of the membrane, and include the membrane having a low electrostatic capacitance.

DETAILED DESCRIPTION OF THE PREFERRED EMBODIMENTS

Figure 1:
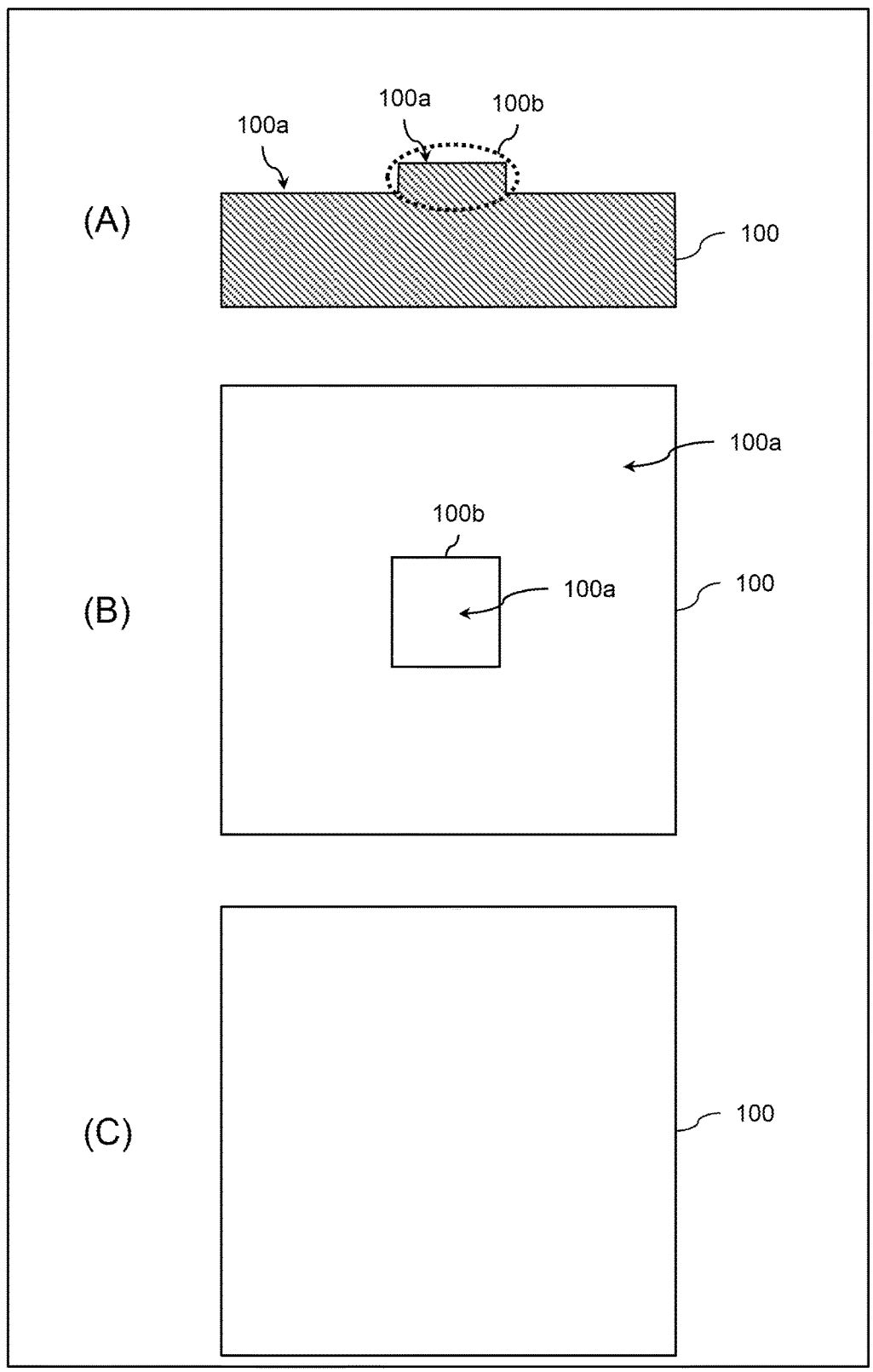
FIG. 1 is an explanatory view for illustrating a method (part 1) of manufacturing a membrane device according to the first embodiment.

Now, embodiments of this invention are described together with the following detailed manufacturing process. Structures of a membrane device and a nanopore device, and materials and manufacturing methods to be used, which are described in the following embodiments, are examples for implementing the concept of this invention, and do not strictly specify the materials and dimensions. Further, the manufacturing methods according to the following embodiments are performed specifically by, for example, a semiconductor manufacturing apparatus. In the drawings, part (A) in each figure is a sectional view of a device during manufacturing or after completion. Part (B) in each figure is a top view of the device during manufacturing or after completion. Part (C) in each figure is a bottom view of the device during manufacturing or after completion. Further, in the following embodiments, like configurations are denoted by like reference symbols. Further, the term "membrane" as used herein refers to a thin film region that is a part of an insulation layer in which a nanopore can be formed and in which both surfaces of the part of the insulation layer are not brought into contact with other layers.

First Embodiment

<Method of Manufacturing Membrane Device>

A method of manufacturing a membrane device according to a first embodiment of this invention is described with reference to FIG. 1 to FIG. 5.

FIG. 1 is an explanatory view for illustrating a method (part 1) of manufacturing a membrane device according to the first embodiment. In FIG. 1, a silicon (Si) substrate 100 having a surface 100*a* of a plane direction {100} is prepared. As illustrated in parts (A) and (B) of FIG. 1, the step of FIG. 1 includes forming a pillar structure called an island pattern 100*b* on a part of the surface 100*a* of the Si substrate 100 through use of a general semiconductor lithography technology and dry etching technology. The height of the island pattern 100*b* to be formed is set to, for example, 300 nanometers, and a vertical dimension and a horizontal dimension of a region of the surface 100*a* of the island pattern 100*b* are set to, for example, 500 nanometers and 500 nanometers, respectively. The shape of the region of the surface 100*a* of the island pattern 100*b* is not limited to a square, and may be another polygon.

Figure 2:
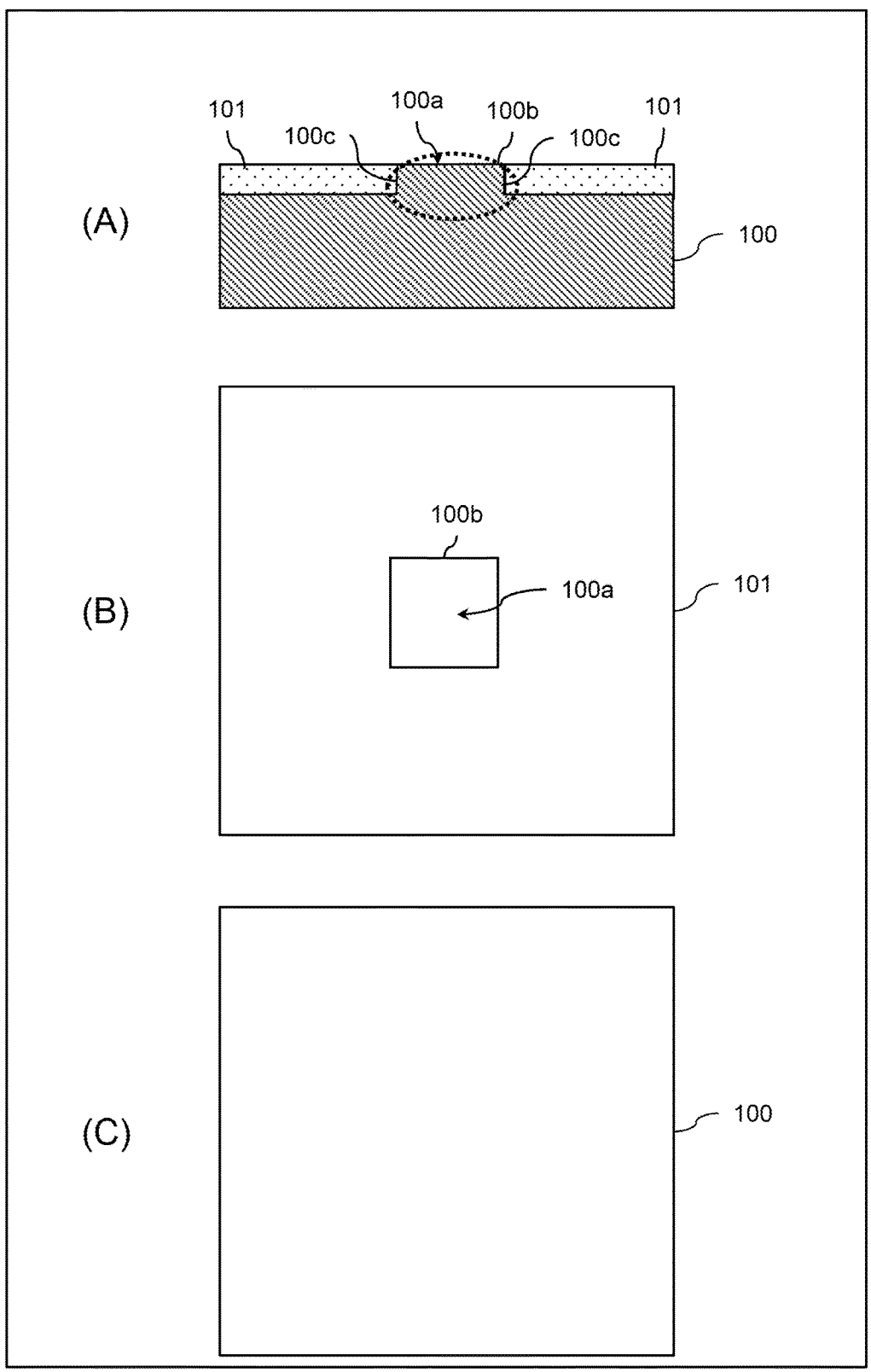
FIG. 2 is an explanatory view for illustrating a method (part 2) of manufacturing a membrane device according to the first embodiment.

FIG. 2 is an explanatory view for illustrating a method (part 2) of manufacturing a membrane device according to the first embodiment. The step of FIG. 2 includes depositing, for example, a SiO$_2$ layer as an insulation layer 101 on the surface 100*a* of the Si substrate 100 obtained in the step of FIG. 1 by a CVD method. The thickness of the SiO$_2$ layer is set to, for example, 500 nanometers. The step of FIG. 2 further includes flattening the surface 100*a* of the Si substrate 100 by a polishing method (chemical mechanical polishing (CMP)) based on a known semiconductor technology. With this, as illustrated in part (B) of FIG. 2, Si is exposed from the surface 100*a* of the island pattern 100*b* of the Si substrate 100, and a side wall 100*c* of the island pattern 100*b* is covered with the insulation layer 101.

Figure 3:
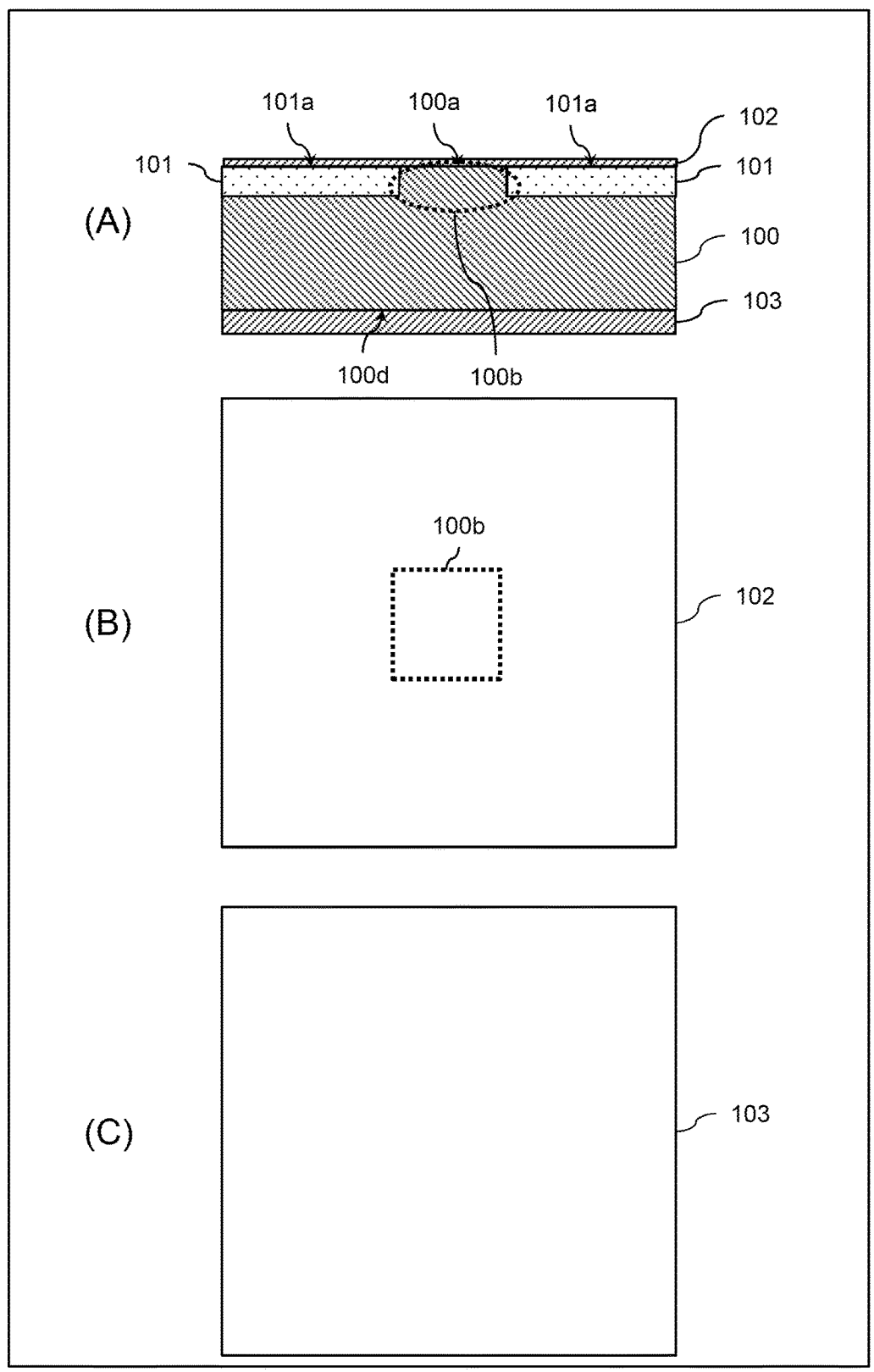
FIG. 3 is an explanatory view for illustrating a method (part 3) of manufacturing a membrane device according to the first embodiment.

FIG. 3 is an explanatory view for illustrating a method (part 3) of manufacturing a membrane device according to the first embodiment. The step of FIG. 3 includes depositing a SiN layer 102 as an insulation layer on the surface 100*a* of the island pattern 100*b* and a surface 101*a* of the insulation layer 101 obtained in the step of FIG. 2. The thickness of the SiN layer 102 is set to, for example, 3 nanometers. The step of FIG. 3 further includes depositing, for example, a SiN layer as an insulation layer 103 on a rear surface 100*d* side of the Si substrate 100 obtained in the step of FIG. 2. The thickness of the insulation layer 103 is set to, for example, 100 nanometers.

Figure 4:
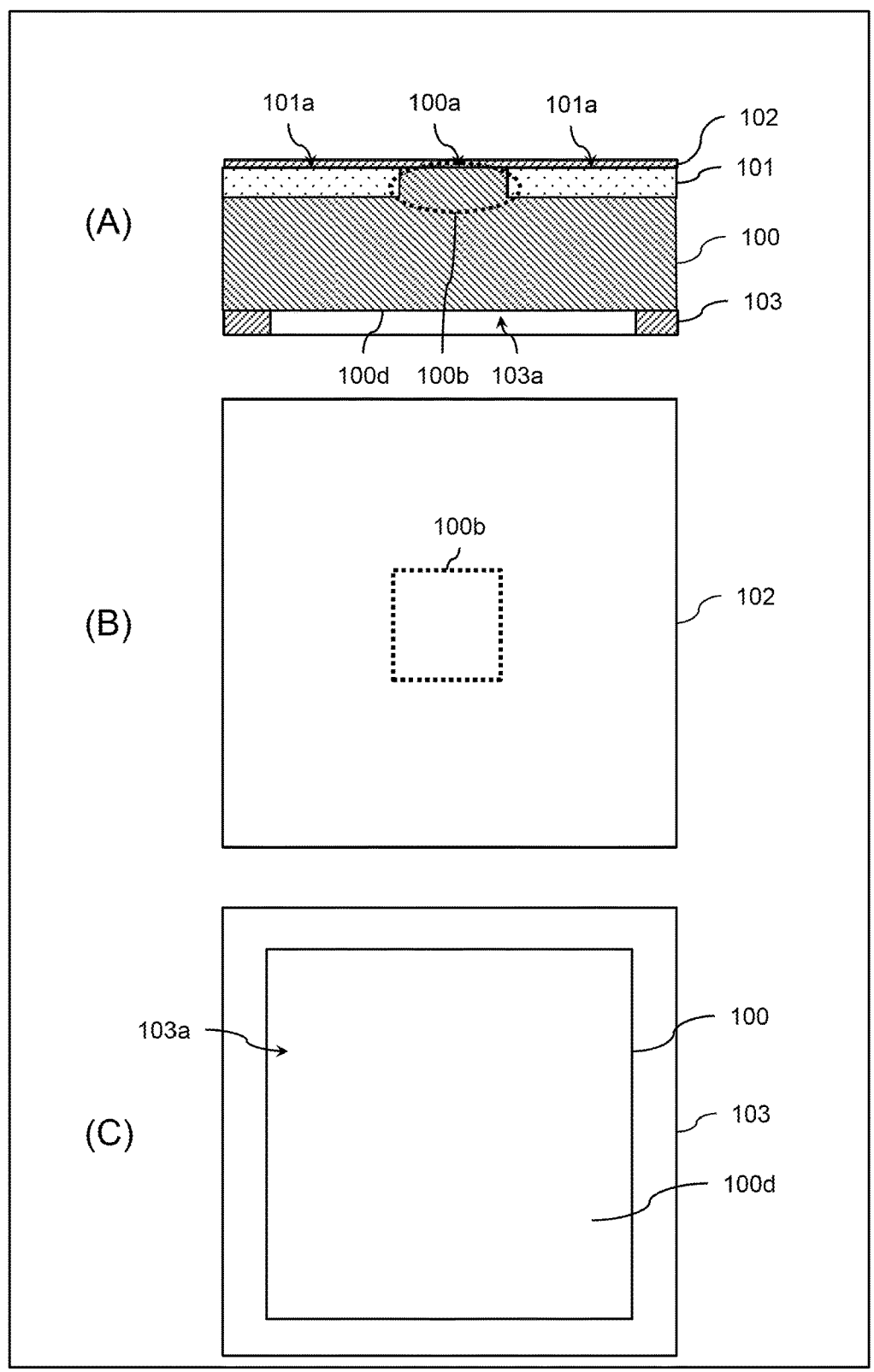
FIG. 4 is an explanatory view for illustrating a method (part 4) of manufacturing a membrane device according to the first embodiment.

FIG. 4 is an explanatory view for illustrating a method (part 4) of manufacturing a membrane device according to the first embodiment. The step of FIG. 4 includes patterning the insulation layer 103 on the rear surface 100*d* side of the Si substrate 100 obtained in the step of FIG. 3 through use of the general semiconductor lithography technology and dry etching technology as illustrated in parts (A) and (C) of FIG. 4. With this, Si is exposed from a partial region (patterned region 103*a*) of the rear surface 100*d* of the Si substrate 100. It is preferred that the size of the patterned region 103*a*, from which Si is exposed, be adjusted in accordance with the thickness of the Si substrate 100. For example, when the Si substrate 100 having a thickness of 725 micrometers is used, it is preferred that a region having, for example, a vertical dimension of 1,038 micrometers and a horizontal dimension of 1,038 micrometers be patterned as the patterned region 103*a*. The shape of the patterned region 103*a* is not limited to a square, and may be another polygon.

Figure 5:
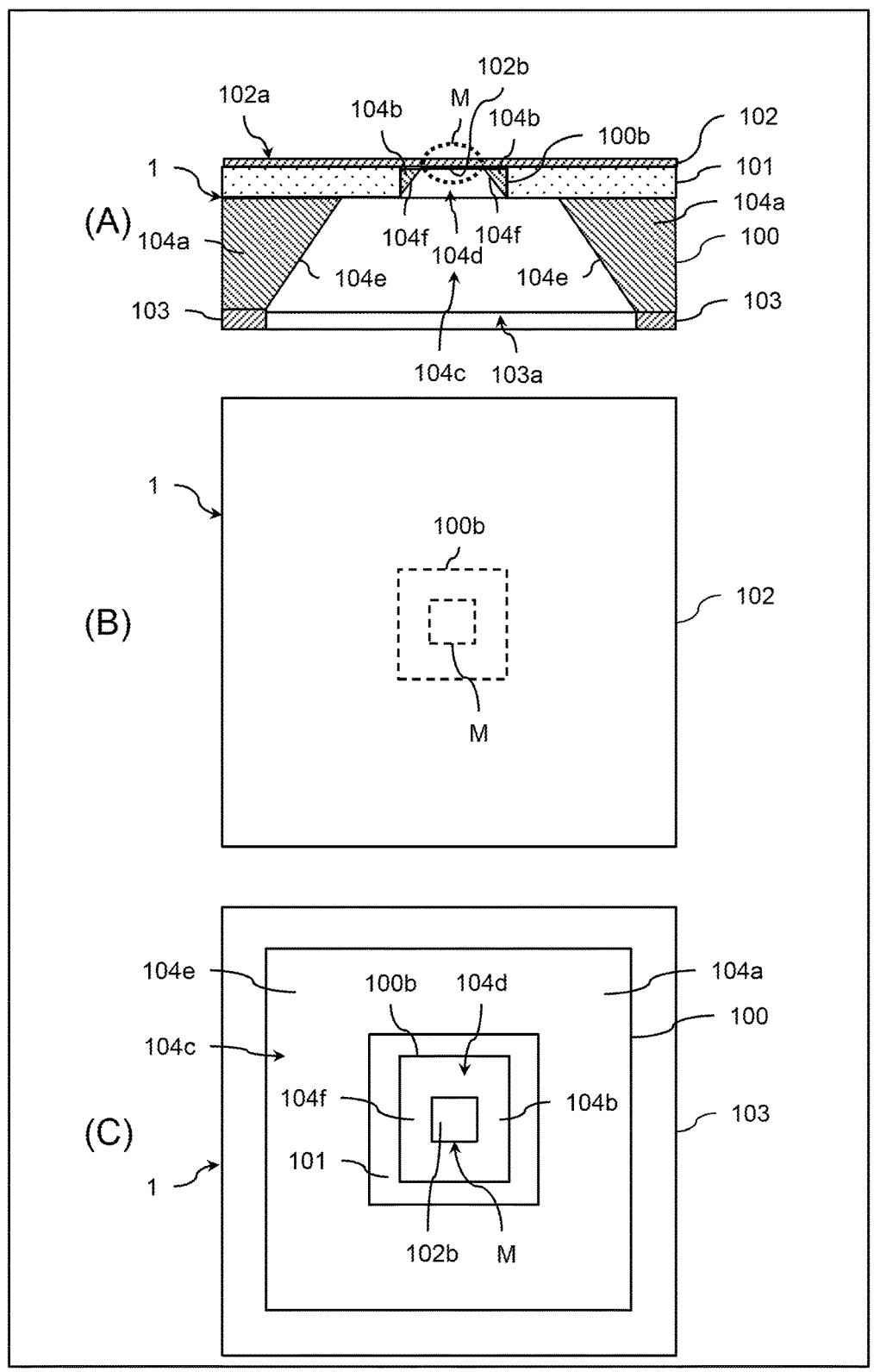
FIG. 5 is an explanatory view for illustrating a method (part 5) of manufacturing a membrane device according to the first embodiment.

FIG. 5 is an explanatory view for illustrating a method (part 5) of manufacturing a membrane device according to the first embodiment. The step of FIG. 5 includes applying an organic protective film (not shown) (for example, ProTEK B3 primer and ProTEK B3 manufactured by Brewer Science, Inc. are used) to a surface 102*a* of the SiN layer 102 obtained in the step of FIG. 4, and then etching the Si substrate 100 with a TMAH solution or a KOH aqueous solution from the rear surface 100*d* side.

Then, as illustrated in part (A) of FIG. 5, two-stage tapered openings 104*c* and 104*d*, in which inner peripheral surfaces 104*e* and 104*f* of the Si substrate 100 are exposed, are formed. In other words, through etching, the Si substrate 100 is formed of a Si region 104*a* having the opening 104*c* formed therein and a Si region 104*b* having the opening 104*d* formed therein. The inner peripheral surfaces 104*e* and 104*f* of the Si substrate 100 are each a {111} plane. The Si region 104*b* is positioned at an outer peripheral edge of the opening 104*d*. The patterned region 103*a* and the openings 104*c* and 104*d* serve as through holes communicating to each other.

The above-mentioned etching is wet etching. Therefore, an opening diameter becomes smaller along with corrosion in an etching direction (direction from the rear surface 100*d* to the surface 100*a* of the Si substrate 100). Then, the inner peripheral surface 104*e* of the Si region 104*a* becomes a tapered surface. Similarly, the inner peripheral surface 104*f* of the Si region 104*b* also becomes a tapered surface. This etching does not corrode the insulation layer 101 (SiO$_2$ layer). Therefore, an opening diameter of the opening 104c on a border of the insulation layer 101 is larger than that of the opening 104d. An opening diameter of the opening 104d on a border of a rear surface 102b of the SiN layer 102 becomes smallest.

In the SiN layer 102, a region (exposed region of the SiN layer 102 in which the island pattern 100b does not remain) defined by the opening diameter of the opening 104d on the border of the rear surface 102b serves as a membrane M. The step of FIG. 5 further includes removing the organic protective film applied to the surface 102a of the SiN layer 102 through use of a solution that does not damage the SiN layer 102, for example, acetone. With this, the membrane M is formed in a center region of the SiN layer 102 defined by the opening diameter of the opening 104d in the Si region 104b, and thus a membrane device 1 is completed.

In the rear surface Si etching process, when the Si substrate 100 is etched from the rear surface 100d side under a state in which the TMAH solution or the KOH aqueous solution is held in contact only with the wafer rear surface side, it is not required to apply the organic protective film to the surface 102a of the SiN layer 102, and the number of processes can thus be reduced.

<Example of Forming Nanopore>

Figure 6:
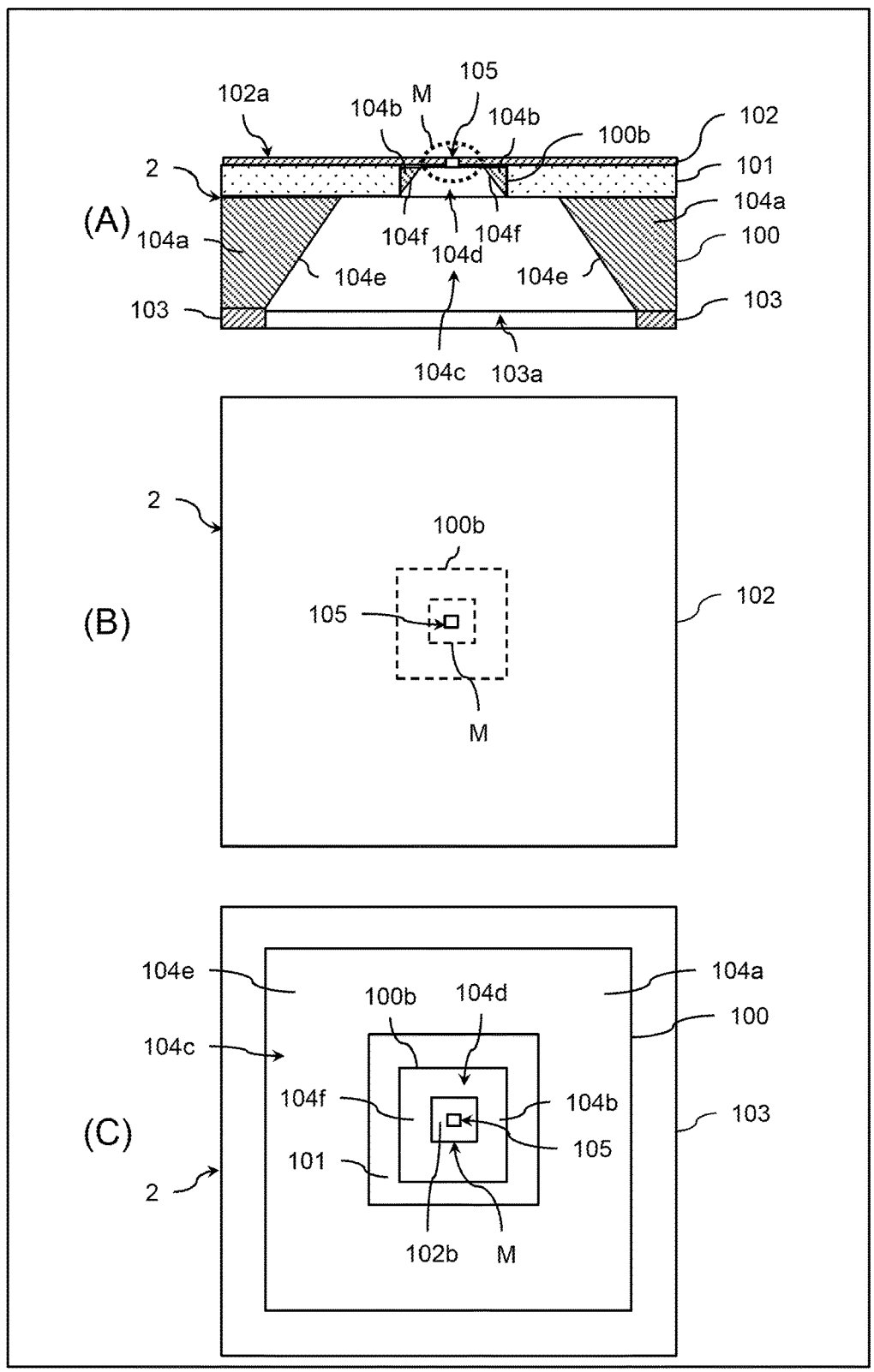
FIG. 6 is an explanatory view for illustrating an example of forming a nanopore in the membrane M in the first embodiment.

FIG. 6 is an explanatory view for illustrating an example of forming a nanopore in the membrane M in the first embodiment. The step of FIG. 6 includes forming a nanopore 105 in the membrane M through use of a known technology (electron beam irradiation process or puncture process) after forming the membrane M through the steps illustrated in FIG. 1 to FIG. 5. With this, the membrane device 1 becomes a nanopore device 2, and can measure an object to be measured that passes through the nanopore 105.

The opening 104d formed by the Si substrate 100 and the Si region 104b remaining on a side wall of the insulation layer 101 exhibits a tapered shape as illustrated in FIG. 6. Therefore, the membrane M formed by crystal anisotropic etching using the TMAH solution or the KOH aqueous solution becomes a region smaller than the island pattern 100b on the Si substrate 100 defined in the step of FIG. 1.

The forming method of Non Patent Literature 2 involves processing a part of a SiN layer in an uppermost portion on a Si substrate to open the SiN layer and etching a poly-Si film positioned under the SiN layer with a KOH aqueous solution, to thereby form a thin film SiN membrane region. In the case of using the forming method of Non Patent Literature 2, the thin film SiN membrane region larger than a partially opened region of the upper SiN layer is formed. An opening region is generally defined by subjecting a resist to drawing and light exposure through use of a lithography technology. For example, when drawing and light exposure are performed through use of i-ray lithography, which is currently relatively inexpensive and popular, a minimum dimension allowing stable drawing and light exposure is about 500 nanometers.

In view of the foregoing, in the forming method of Non Patent Literature 2, the thin film SiN membrane region becomes a region of 500 nanometers×500 nanometers or more. In contrast, the manufacturing method according to the first embodiment forms the membrane M smaller than the island pattern 100b on the Si substrate 100 defined in the step illustrated in FIG. 1. For example, when the island pattern 100b on the Si substrate 100 of a region of 500 nanometers×500 nanometers is formed similarly through use of the i-ray lithography, the membrane M finally becomes a region of smaller than 500 nanometers×500 nanometers.

For example, in the case of following the dimensions used in the first embodiment, the membrane M of about 100 nanometers×about 100 nanometers is formed. Therefore, the membrane M smaller than the thin film SiN membrane region of Non Patent Literature 2 is formed stably. In order to reduce the membrane M in thickness, needless to say, it is preferred that the area of the membrane M be as narrow as possible. This is because, as the region of the membrane M becomes narrower, there is a decreased probability that inevitable defects (a weak spot and a pinhole caused by, for example, a binding defect between atoms) occurring at a time of formation of the membrane M are present in the membrane M.

When it is intended to further reduce the membrane M in size, it is only required to further reduce the size of the island pattern 100b on the Si substrate 100, or to further increase the height of the island pattern 100b on the Si substrate 100 and form the insulation layer 101 having a height having the increased height. With this, the region of the membrane M can be reduced in size to a region of about 10 nanometers× about 10 nanometers.

Further, in the forming method of Non Patent Literature 2, at a time of formation of the thin film SiN membrane, a rear surface of the membrane is brought into contact with the TMAH solution, and a surface of the membrane is brought into contact with the KOH aqueous solution. Therefore, there are two processes that may damage the membrane. In contrast, in the manufacturing method according to the first embodiment, at a time of formation of the membrane M, the TMAH solution or the KOH aqueous solution is brought into contact with the membrane M from the rear surface 102b side only once. In other words, as compared to the forming method of Non Patent Literature 2, the number of the processes that may damage the membrane M is smaller by one. Thus, it is possible to form the membrane M more stably.

Further, in the measurement method of Non Patent Literature 2, an ion current flowing when the DNA passes through a nanopore is measured through use of a thin film membrane having the nanopore opened therein. In this case, noise at a time of current measurement increases. When noise at a time of current measurement is large, a current signal derived from an object to be measured becomes unclear, resulting in an increase in incorrect identification. As one of the reasons that noise at a time of current measurement is large, there is given a large electrostatic capacitance of a structure that is sandwiched between aqueous solutions of upper and lower chambers and is formed of a membrane, a Si substrate, and a laminated film on the Si substrate.

In general, as the ratio of an insulator having a low specific dielectric constant of the structure sandwiched between the aqueous solutions of the upper and lower chambers increases, the electrostatic capacitance of the structure sandwiched between the aqueous solutions of the upper and lower chambers decreases. As a result, noise at a time of measuring an ion current flowing when the DNA passes through the nanopore is reduced.

In Non Patent Literature 2, the poly-Si film is not an insulation film but a semiconductor. Therefore, only the ultrathin SiN membrane of about 3 nanometers, the upper SiN film of 100 nanometers, and the SiN film adhering to a part of the rear surface of the Si substrate are each formed of an insulation film. Under this condition, the electrostatic capacitance of the entire structure sandwiched between the aqueous solutions of the upper and lower chambers cannot be sufficiently decreased. As a result, noise at a time of measuring an ion current flowing when the DNA passes through the nanopore increases.

Meanwhile, in the manufacturing method according to the first embodiment, the insulation layer 101 ($SiO_2$ layer) having a dielectric constant lower than that of the SiN layer is formed so as to have a thickness of 300 nanometers, and further, the SiN film that is the insulation layer 103 is formed so as to have a thickness of 100 nanometers on the rear surface 100d of the Si substrate 100. Therefore, the electrostatic capacitance of the membrane device becomes lower than that in the structure of Non Patent Literature 2. Therefore, when an ion current flowing when the DNA passes through the nanopore 105 is measured after the nanopore 105 is opened, noise at a time of current measurement is reduced. Although the thickness of the insulation layer 101 is set to 300 nanometers in the first embodiment, when the thickness is increased, noise can be further reduced correspondingly.

In this case, it is only required that the island pattern 100b of the Si substrate 100 to be processed in the first step illustrated in FIG. 1 be processed more deeply in accordance with an increase in thickness of the insulation layer 101. Further, it is only required that the region of the island pattern 100b of the Si substrate 100 be adjusted in accordance with the depth thereof so that a desired membrane region is obtained. In order to form a small region of the membrane M while obtaining a noise reduction effect as in the first embodiment, it is preferred that the thickness of the insulation layer 101 (that is, the height of the Si region 104b) be 100 nanometers or more and smaller than 1 micrometer.

When the thickness of the insulation layer 101 is 100 nanometers or more, the noise reduction effect can be obtained. Further, when the height of the Si region 104b is smaller than 1 micrometer, the island pattern 100b having small variation in height within a wafer surface can be processed. When the island pattern 100b having small variation in height within a wafer surface can be formed, variation in size of the membrane M can also be reduced correspondingly. Thus, the membrane M of a small region can be formed with small variation in size within a wafer surface.

<Example of DNA Sequencing System Using Nanopore>

Figure 7:
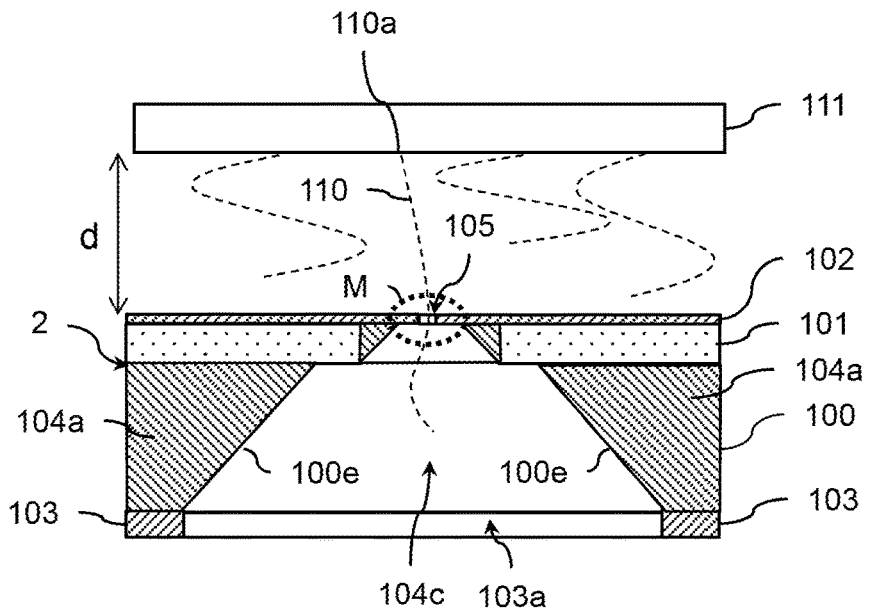
FIG. 7 is an explanatory view for illustrating an active drive system that is a DNA sequencing system using a nanopore.

FIG. 7 is an explanatory view for illustrating an active drive system that is a DNA sequencing system using a nanopore. The active drive system is a system involving bringing a probe substrate 111 having an end of a DNA 110 fixed thereto close to the nanopore 105 of the nanopore device 2, and precisely moving the probe substrate 111 after the DNA 110 is introduced into the nanopore 105, to thereby perform speed control and position control of the DNA 110 in the nanopore 105. In the active drive system, speed control and position control of the DNA 110 in the nanopore 105 are precisely performed. Thus, the accuracy of sequencing of the DNA 110 using the nanopore 105 can be enhanced.

The nanopore device 2 formed in the first embodiment has high affinity to the active drive system. This is because a distance d between the probe substrate 111 and the membrane M can be set to 0 at minimum, and hence DNA sequencing can be performed up to a portion of the DNA 110 fixed to the probe substrate 111, which is close to a fixed end 110a.

Figure 8:
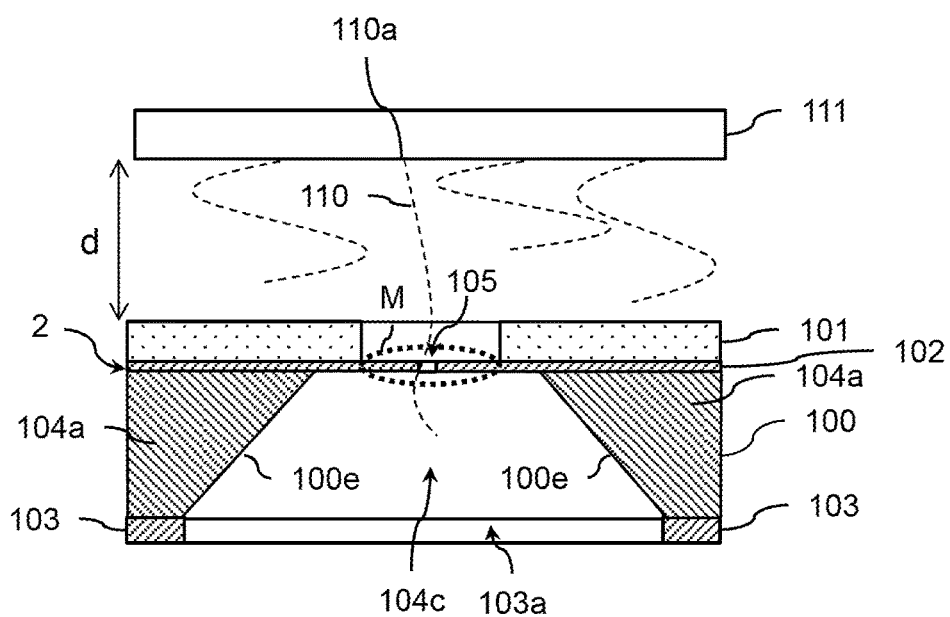
FIG. 8 is an explanatory view for illustrating another example of the active drive system.

FIG. 8 is an explanatory view for illustrating another example of the active drive system. The nanopore device 2 of FIG. 8 is a device in which the insulation layer 101 ($SiO_2$ layer) is formed on the SiN layer 102 in order to reduce noise in the nanopore device 2. A minimum value of the distance d between the probe substrate 111 and the SiN layer 102 cannot be set to be smaller than the thickness of the insulation layer 101. Therefore, DNA sequencing cannot be performed up to a portion of the DNA 110 fixed to the probe substrate 111, which is close to the fixed end 110a. As the thickness of the insulation layer 101 increases, the length that can be subjected to DNA sequencing decreases. For this reason, the membrane device 1 (nanopore device 2) formed in the first embodiment is suitable for being applied with the active drive system at a time of DNA sequencing.

The insulation layers 101 and 103 may be made of materials other than those described in the first embodiment as long as the materials are less liable to be scraped at a time of TMAH or KOH etching. For example, in the above-mentioned example, the insulation layer 101 is formed of the $SiO_2$ layer, but may be formed of a SiN layer. Further, the insulation layer 103 is formed of the SiN layer, but may be formed of a $SiO_2$ layer. In other words, it is only required that the insulation layers 101 and 103 be made of such materials that the etching rate thereof by TMAH or KOH etching is sufficiently low as compared to the etching rate of Si by TMAH or KOH etching. Further, it is only required that the SiN layer 102 be made of a material that is hardly damaged at a time of TMAH or KOH etching. For example, hafnium oxide ($HfO_2$) or hafnium aluminate (HfAlO) may be used instead of SiN described in the first embodiment.

At a time of etching of the Si substrate 100, an aqueous solution other than the TMAH solution or the KOH solution may be used. For example, it is only required that the aqueous solution be an alkaline aqueous solution that enables crystal anisotropic etching of Si as in the first embodiment, hardly damages the membrane M, and achieves an etching rate of the insulation layers 101 and 103 sufficiently lower than that of Si.

The membrane device 1 formed by the manufacturing method described in the first embodiment has a feature in its finished shape. Specifically, for example, the membrane device 1 includes the Si regions 104a and 104b, in which the inner peripheral surfaces 104e and 104f of the Si substrate 100, each being a {111} plane, are exposed, and the Si region 104b is positioned on the side wall of the insulation layer 101.

In the first embodiment, description is given of an example of the manufacturing method using the Si substrate 100 having the surface 100a of the plane direction {100}, but certain effects can also be obtained by other manufacturing methods. For example, when the Si substrate 100 having the surface 100a of a plane direction {110} is used, the Si substrate 100 is etched perpendicularly from the rear surface 100d by TMAH or KOH etching. Therefore, the openings 104c and 104d do not have such tapered shapes as illustrated in FIG. 6. As a result, the membrane M becomes larger as compared to the case in which the membrane M is formed through use of the Si substrate 100 having the surface 100a of the plane direction {100}. However, the membrane M does not become larger than the area of the island pattern 100b of the Si substrate 100 patterned first.

As described above, the membrane M can be formed stably with satisfactory yield through use of the manufacturing method according to the first embodiment. Further, after the nanopore 105 is formed in the membrane M, noise at a time of measurement of ion current flowing when the DNA 110 passes through the nanopore 105 can also be reduced. Further, the membrane device 1 (nanopore device 2), which is also suitable for being applied with the active drive system at a time of DNA sequencing, can be formed.

Second Embodiment

In a second embodiment of this invention, description is given of a suitable manufacturing method for the membrane device 1, which reduces noise at a time of measuring an ion current flowing when the DNA passes through a nanopore. Specifically, for example, the manufacturing method according to the second embodiment involves processing the island pattern 100b of Si in the first embodiment so as to be deep (for example, a height of 1 micrometer or more and 20 micrometers or less) and forming the insulation layer 101 of FIG. 2 so as to be thick (for example, 1 micrometer or more and 20 micrometers or less), to thereby significantly reduce the electrostatic capacitance of the membrane device 1. The height or the thickness of 20 micrometers or less of the island pattern 100b stabilizes processing of the Si pattern and formation of the insulation layer 101.

When the island pattern 100b of Si is processed deeply to have a height of about 1 micrometer or more and about 20 micrometers or less, there is a problem in that the region of the membrane M formed of the SiN layer 102 cannot be finally reduced in size stably. This is because, when the height of the island pattern 100b of Si is increased to about 1 micrometer or more and about 20 micrometers or less, variation in size of the membrane M having the region defined by the opening diameter of the opening 104d in the Si region 104b after TMAH or KOH etching of FIG. 5 is also increased.

The reason for the foregoing is as follows. The amount of etching to the island pattern 100b of the Si substrate 100 increases along with an increase in thickness of the island pattern 100b of the Si substrate 100 that is required to be etched, and as a result, variation in finished shape caused by instability of etching itself with a TMAH or KOH aqueous solution is increased. Further, when the height of the island pattern 100b is increased to about 1 micrometer or more and about 20 micrometers or less, variation in height of the island pattern 100b is also increased due to variation in etching at a time of processing of the island pattern 100b. Therefore, variation in size of the membrane M formed of the SiN layer 102 is also increased as a result.

When the height of the island pattern 100b is set to 10 micrometers, variation in region of the membrane M after TMAH or KOH etching is 1 micrometer or more. Therefore, it is impossible to stably form the membrane M of a small region of at least 1 micrometer×1 micrometer or less.

<Method of Manufacturing Membrane Device 1>

A method of manufacturing the membrane device 1 according to the second embodiment is described with reference to FIG. 9 to FIG. 15.

Figure 9:
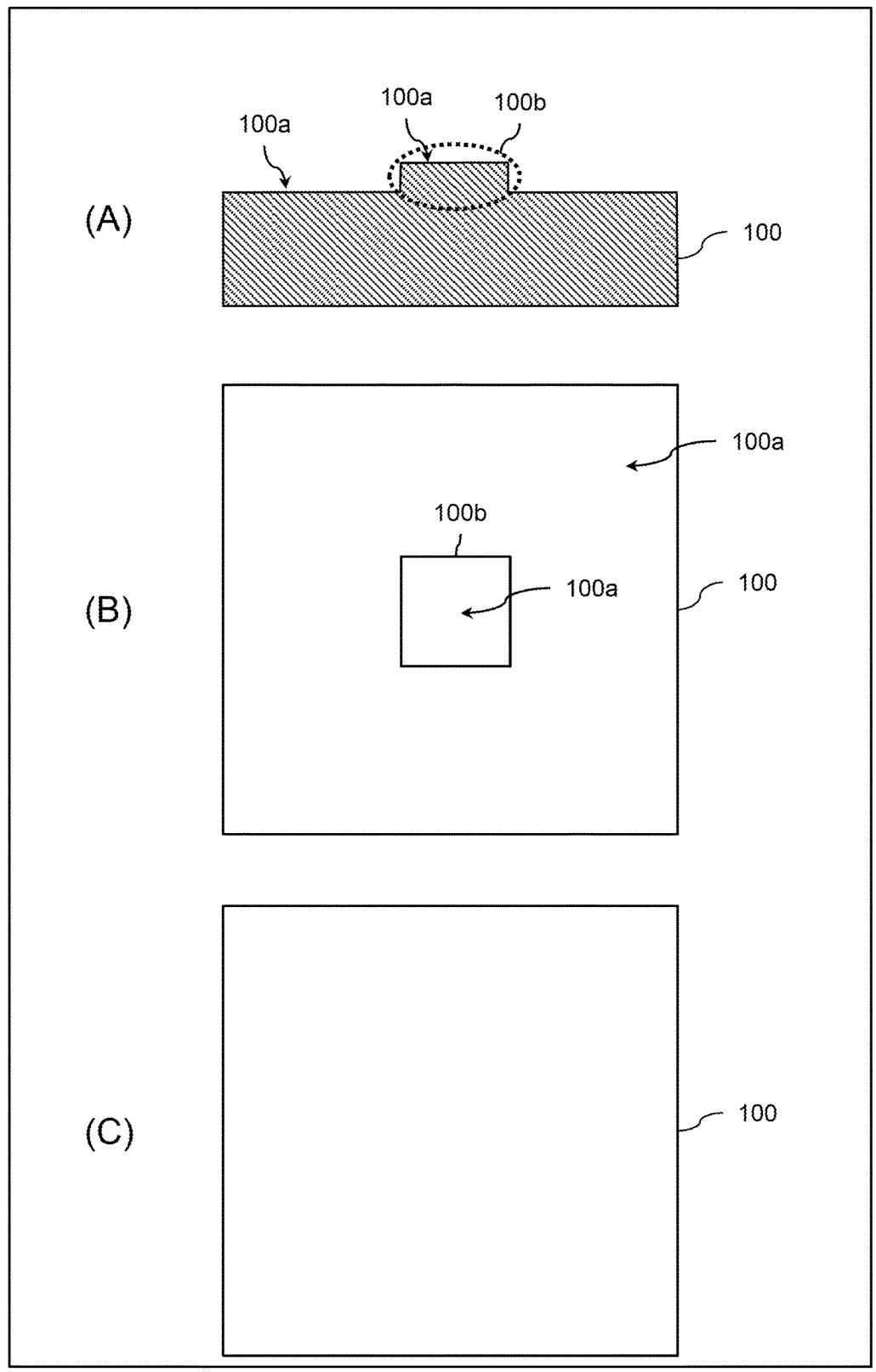
FIG. 9 is an explanatory view for illustrating a method (part 1) of manufacturing a membrane device according to the second embodiment.

FIG. 9 is an explanatory view for illustrating a method (part 1) of manufacturing a membrane device according to the second embodiment. In FIG. 9, a Si substrate 100 having a surface 100a of a plane direction {100} is prepared. As illustrated in parts (A) and (B) of FIG. 9, the step of FIG. 9 includes forming a pillar structure called an island pattern 100b on a part of the surface 100a of the Si substrate 100 through use of a general semiconductor lithography technology and dry etching technology. The height of the island pattern 100b to be formed is set to, for example, 20 micrometers. Further, a vertical dimension and a horizontal dimension of a region of the surface 100a of the island pattern 100b are set to, for example, 35 micrometers and 35 micrometers, respectively. The shape of the region of the surface 100a of the island pattern 100b is not limited to a square, and may be another polygon.

Figure 10:
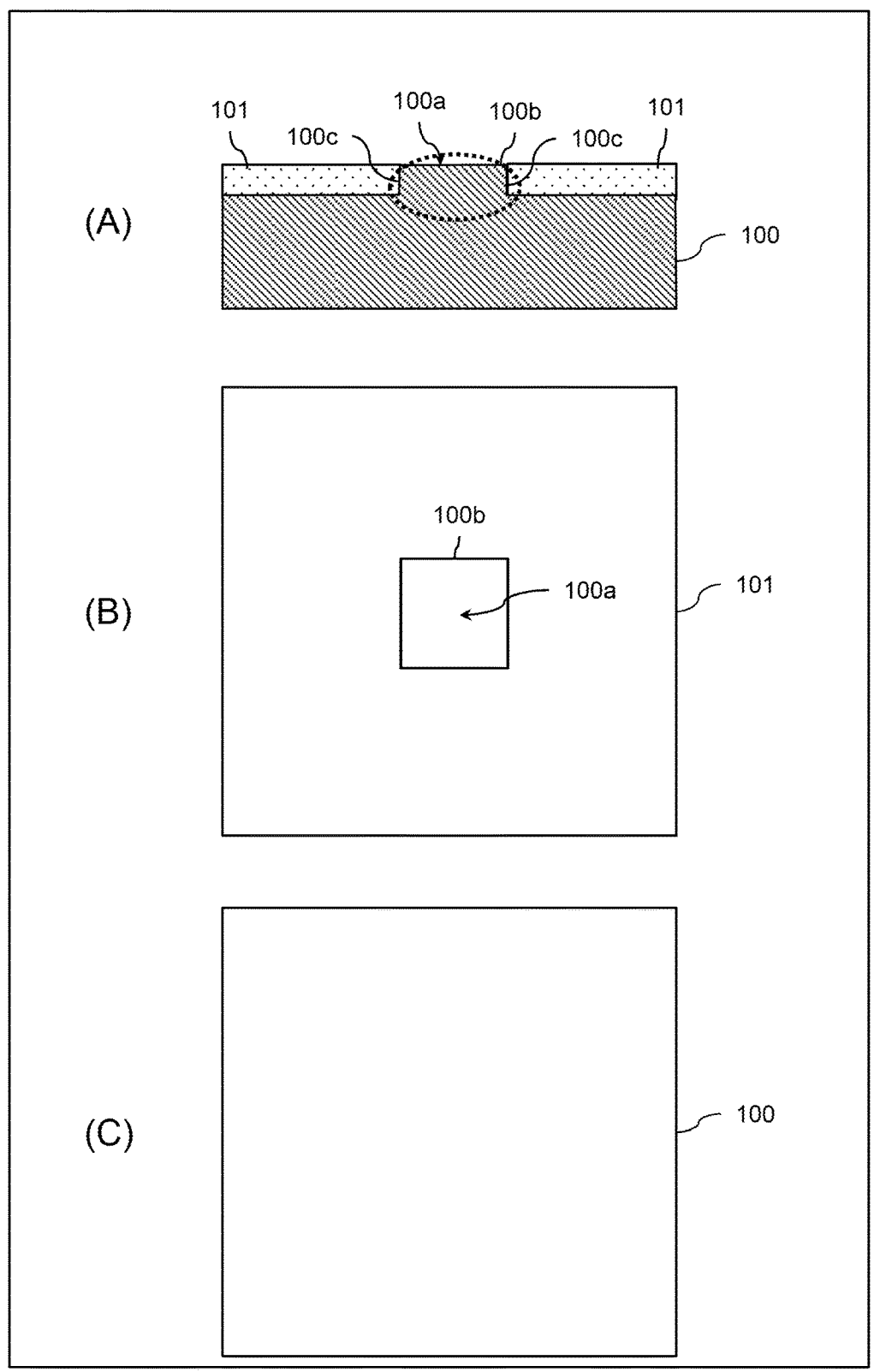
FIG. 10 is an explanatory view for illustrating a method (part 2) of manufacturing a membrane device according to the second embodiment.

FIG. 10 is an explanatory view for illustrating a method (part 2) of manufacturing a membrane device according to the second embodiment. The step of FIG. 10 includes depositing a $SiO_2$ layer as an insulation layer 101 on the surface 100a of the Si substrate 100 obtained in the step of FIG. 9 by a CVD method. The thickness of the insulation layer 101 is set to, for example, 30 micrometers. The step of FIG. 10 further includes flattening the surface by a polishing method (CMP) based on a known semiconductor technology. With this, as illustrated in part (B) of FIG. 10, Si is exposed from the surface 100a of the island pattern 100b of the Si substrate 100, and a side wall 100c of the island pattern 100b is covered with the insulation layer 101.

Figure 11:
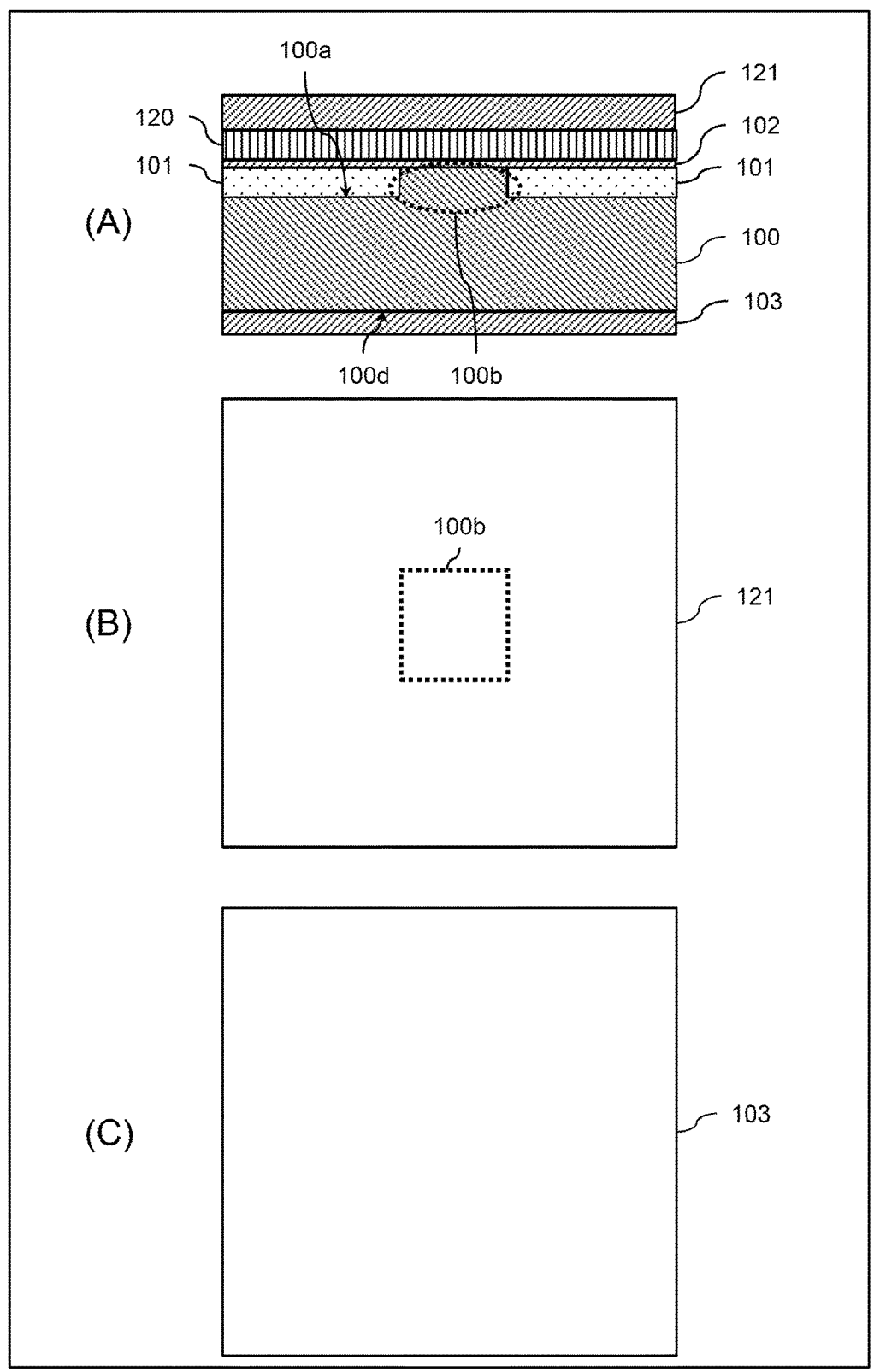
FIG. 11 is an explanatory view for illustrating a method (part 3) of manufacturing a membrane device according to the second embodiment.

FIG. 11 is an explanatory view for illustrating a method (part 3) of manufacturing a membrane device according to the second embodiment. The step of FIG. 11 includes depositing a SiN layer 102 as an insulation layer on the surface 100a side of the Si substrate 100 obtained in the step of FIG. 9. The thickness of the SiN layer 102 is set to, for example, 3 nanometers. The step of FIG. 11 further includes depositing a poly-Si layer 120, which is a conductive layer, on the SiN layer 102. The thickness of the poly-Si layer 120 is set to, for example, 150 nanometers. The step of FIG. 11 further includes depositing a SiN layer 121, which is an insulation layer, on the poly-Si layer 120. The thickness of the SiN layer 121 to be deposited is set to, for example, 100 nanometers. The step of FIG. 11 further includes depositing a SiN layer as an insulation layer 103 on the rear surface 100d side of the Si substrate 100. The thickness of the insulation layer 103 is set to, for example, 100 nanometers.

Figure 12:
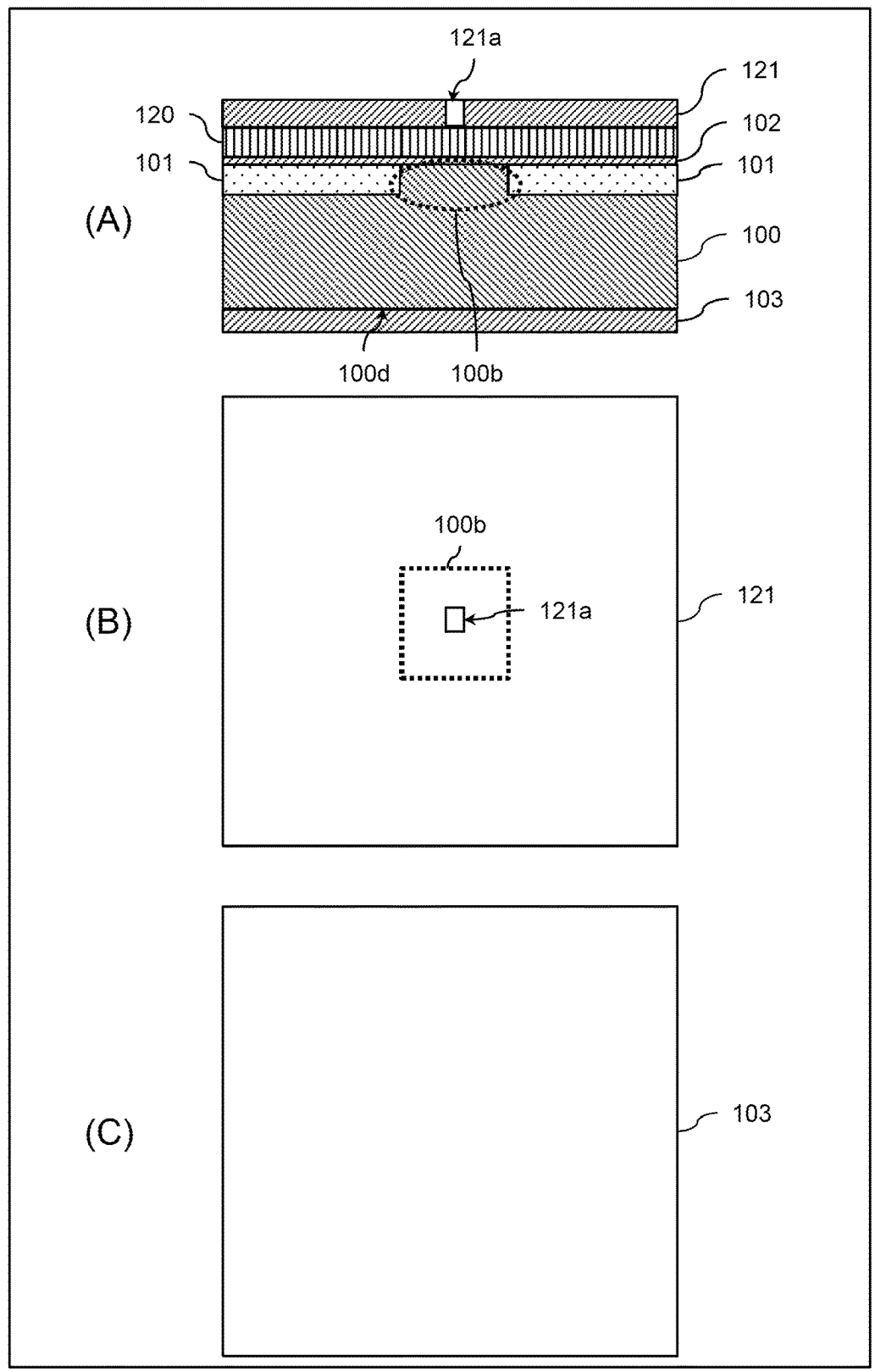
FIG. 12 is an explanatory view for illustrating a method (part 4) of manufacturing a membrane device according to the second embodiment.

FIG. 12 is an explanatory view for illustrating a method (part 4) of manufacturing a membrane device according to the second embodiment. The step of FIG. 12 includes opening a part of the SiN layer 121 of the Si substrate 100 obtained in the step of FIG. 11 through use of a lithography technology and a dry etching technology. An opening 121a is a rectangular region having an area of, for example, 100 nanometers×100 nanometers.

Figure 13:
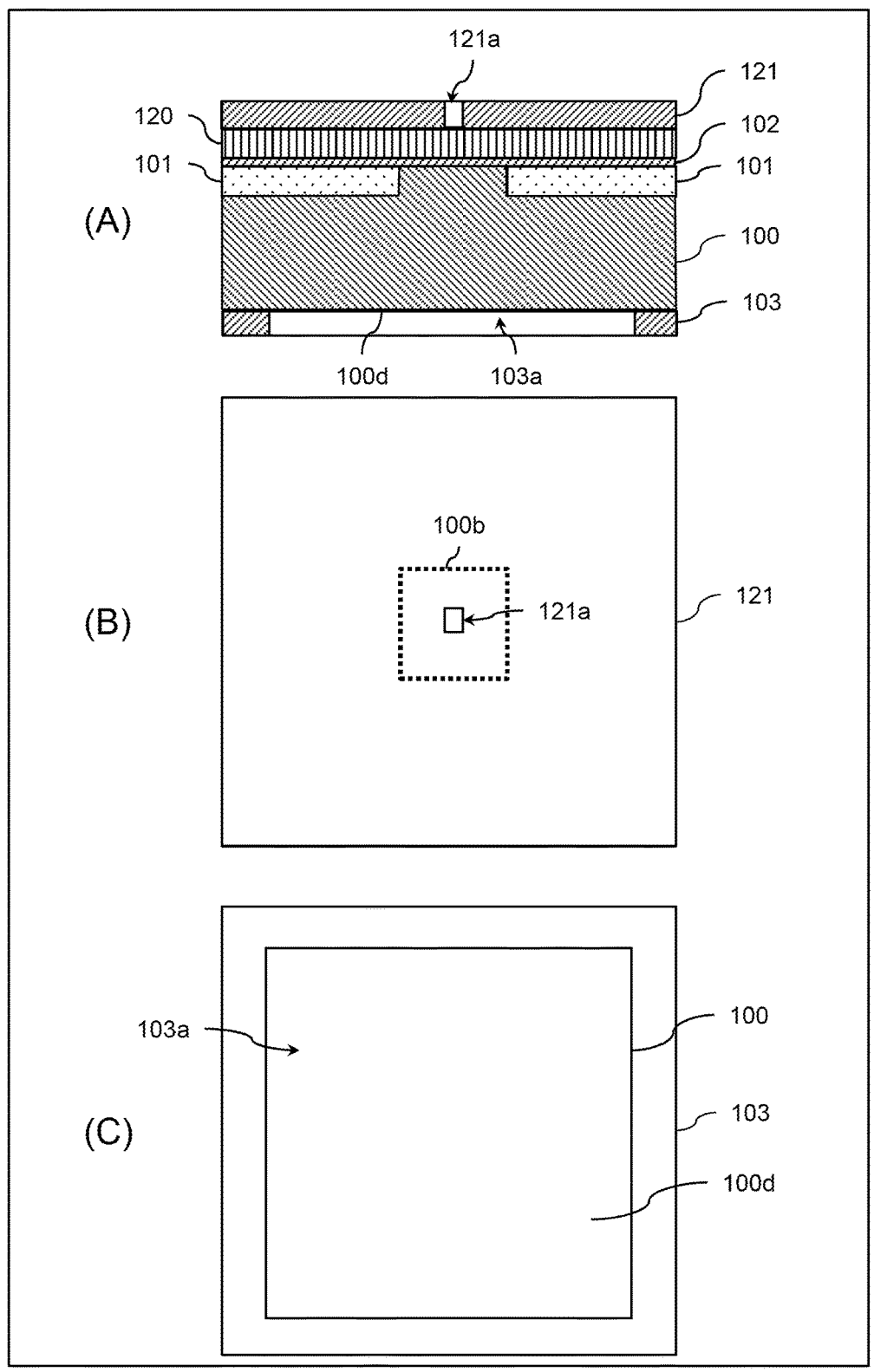
FIG. 13 is an explanatory view for illustrating a method (part 5) of manufacturing a membrane device according to the second embodiment.

FIG. 13 is an explanatory view for illustrating a method (part 5) of manufacturing a membrane device according to the second embodiment. The step of FIG. 13 includes patterning the insulation layer 103 on the rear surface 100d side of the Si substrate 100 obtained in the step of FIG. 12 through use of the general semiconductor lithography technology and dry etching technology as illustrated in parts (A) and (C) of FIG. 13. With this, Si is exposed from a partial region of the rear surface 100d of the Si substrate 100. It is preferred that the size of the patterned region 103a, from which Si is exposed, be adjusted in accordance with the thickness of the Si substrate 100. For example, when the Si substrate 100 having a thickness of 725 micrometers is used, it is preferred that a region having, for example, a vertical dimension of 1,038 micrometers and a horizontal dimension of 1,038 micrometers be patterned as the patterned region 103a. The shape of the patterned region 103a is not limited to a square, and may be another polygon.

Figure 14:
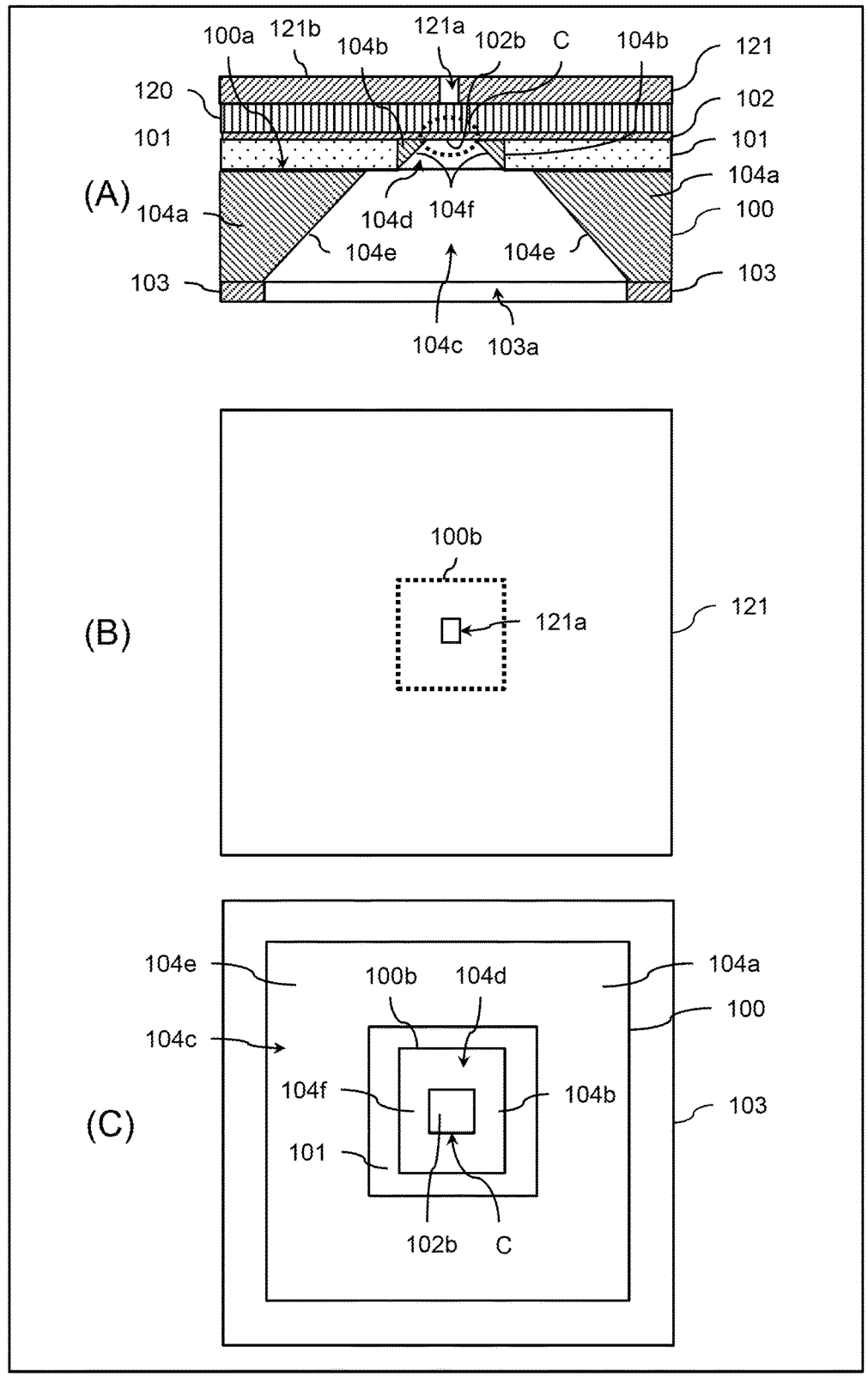
FIG. 14 is an explanatory view for illustrating a method (part 6) of manufacturing a membrane device according to the second embodiment.

FIG. 14 is an explanatory view for illustrating a method (part 6) of manufacturing a membrane device according to the second embodiment. The step of FIG. 14 includes applying an organic protective film (not shown) (for example, ProTEK B3 primer and ProTEK B3 manufactured by Brewer Science, Inc. are used) to a surface 121b of the SiN layer 121 of the Si substrate 100 obtained in the step of FIG. 13, and then etching the Si substrate 100 with a TMAH solution or a KOH aqueous solution from the rear surface 100d side.

Then, as illustrated in part (A) of FIG. 14, two-stage tapered openings 104c and 104d, in which inner peripheral surfaces 104e and 104f of the Si substrate 100 are exposed, are formed. In other words, through etching, the Si substrate 100 is formed of a Si region 104a having the opening 104c formed therein and a Si region 104b having the opening 104d formed therein. The inner peripheral surfaces 104e and 104f of the Si substrate 100 are each a {111} plane. The Si region 104b is positioned at an outer peripheral edge of the opening 104d. The patterned region 103a and the openings 104c and 104d serve as through holes communicating to each other.

The above-mentioned etching is wet etching. Therefore, an opening diameter becomes smaller along with corrosion in an etching direction (direction from the rear surface 100d to the surface 100a of the Si substrate 100). Then, the inner peripheral surface 104e of the Si region 104a becomes a tapered surface. Similarly, the inner peripheral surface 104f of the Si region 104b also becomes a tapered surface. This etching does not corrode the insulation layer 101 ($SiO_2$ layer). Therefore, an opening diameter of the opening 104c on a border of the insulation layer 101 is larger than that of the opening 104d. An opening diameter of the opening 104d on a border of a rear surface 102b of the SiN layer 102 becomes smallest.

In the SiN layer 102, a region defined by the opening diameter of the opening 104d on the border of the rear surface 102b serves as a center region C, which becomes a membrane M of the SiN layer 102 in the next step. The step of FIG. 14 further includes removing the organic protective film applied to the surface 121b of the SiN layer 121 through use of a solution that does not damage the SiN layer 121, for example, acetone. With this, the center region C is formed. Through manufacturing of the center region C with the dimensions used in the second embodiment, the center region C becomes a region of about 10 micrometers square.

In the rear surface Si etching process, when the Si substrate 100 is etched from the rear surface 100d side under a state in which the TMAH solution or the KOH aqueous solution is held in contact only with the wafer rear surface side, it is not required to apply the organic protective film to the surface 121b of the SiN layer 121, and the number of processes can thus be reduced.

Figure 15:
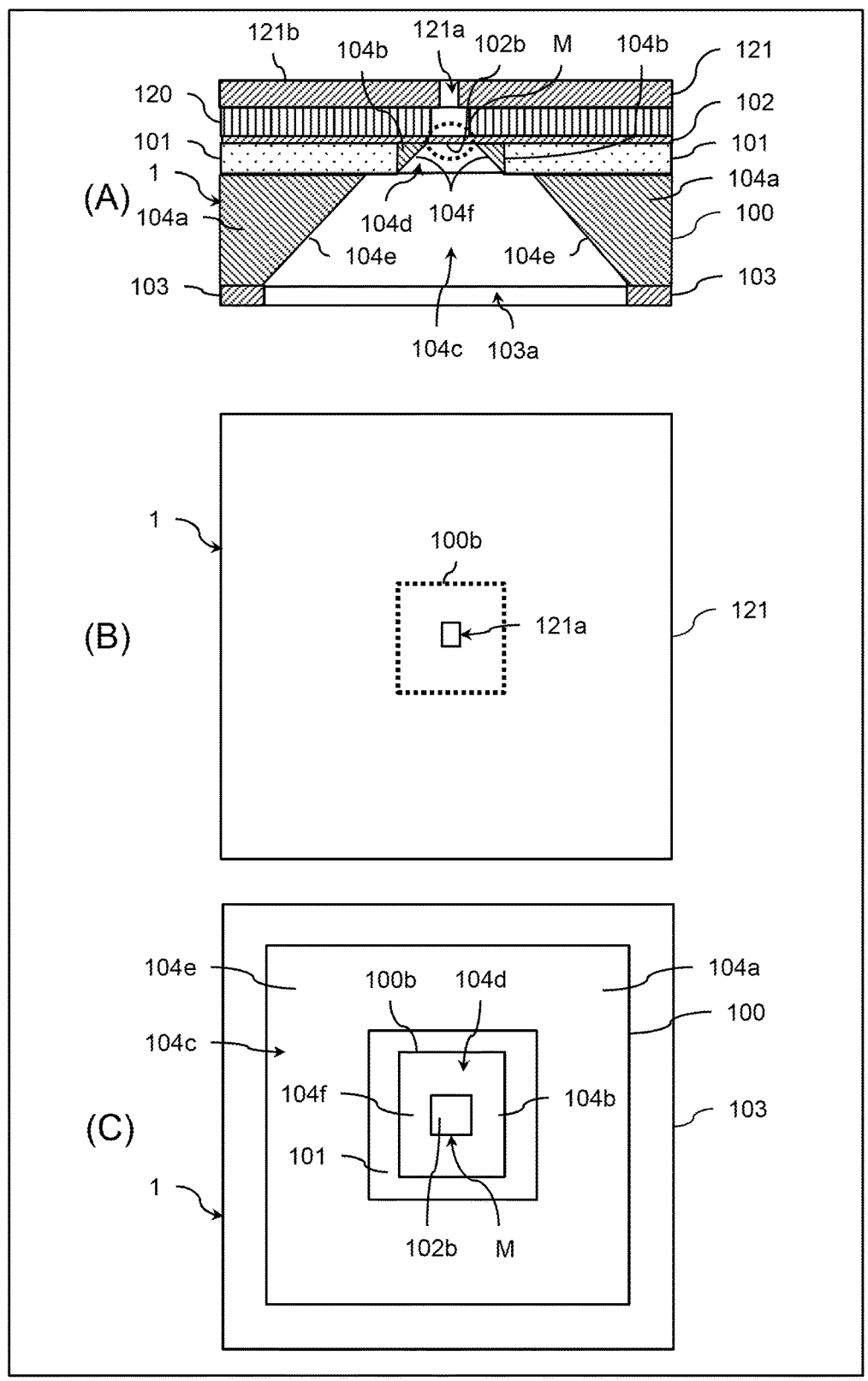
FIG. 15 is an explanatory view for illustrating a method (part 7) of manufacturing a membrane device according to the second embodiment.

FIG. 15 is an explanatory view for illustrating a method (part 7) of manufacturing a membrane device according to the second embodiment. The step of FIG. 15 includes etching a part of the poly-Si layer 120 of the Si substrate 100 obtained in the step of FIG. 14 with the SiN layer 121 being a mask through use of the KOH aqueous solution or the TMAH solution. With this, the membrane M having a region defined by the poly-Si layer 120 is formed to complete the membrane device 1. In consideration of variation in thickness of the poly-Si layer 120 and variation in etching rate by the TMAH solution or the KOH aqueous solution, it is preferred that etching in the step of FIG. 15 be performed for a long time period (that is, overetching be performed) as compared to a time period required for etching of the poly-Si layer 120 to a designed thickness. For example, it is preferred that overetching be performed so that the size of the membrane M having the region defined by the poly-Si layer 120 extends to about a region of 500 nanometers×500 nanometers.

<Example of Forming Nanopore>

Figure 16:
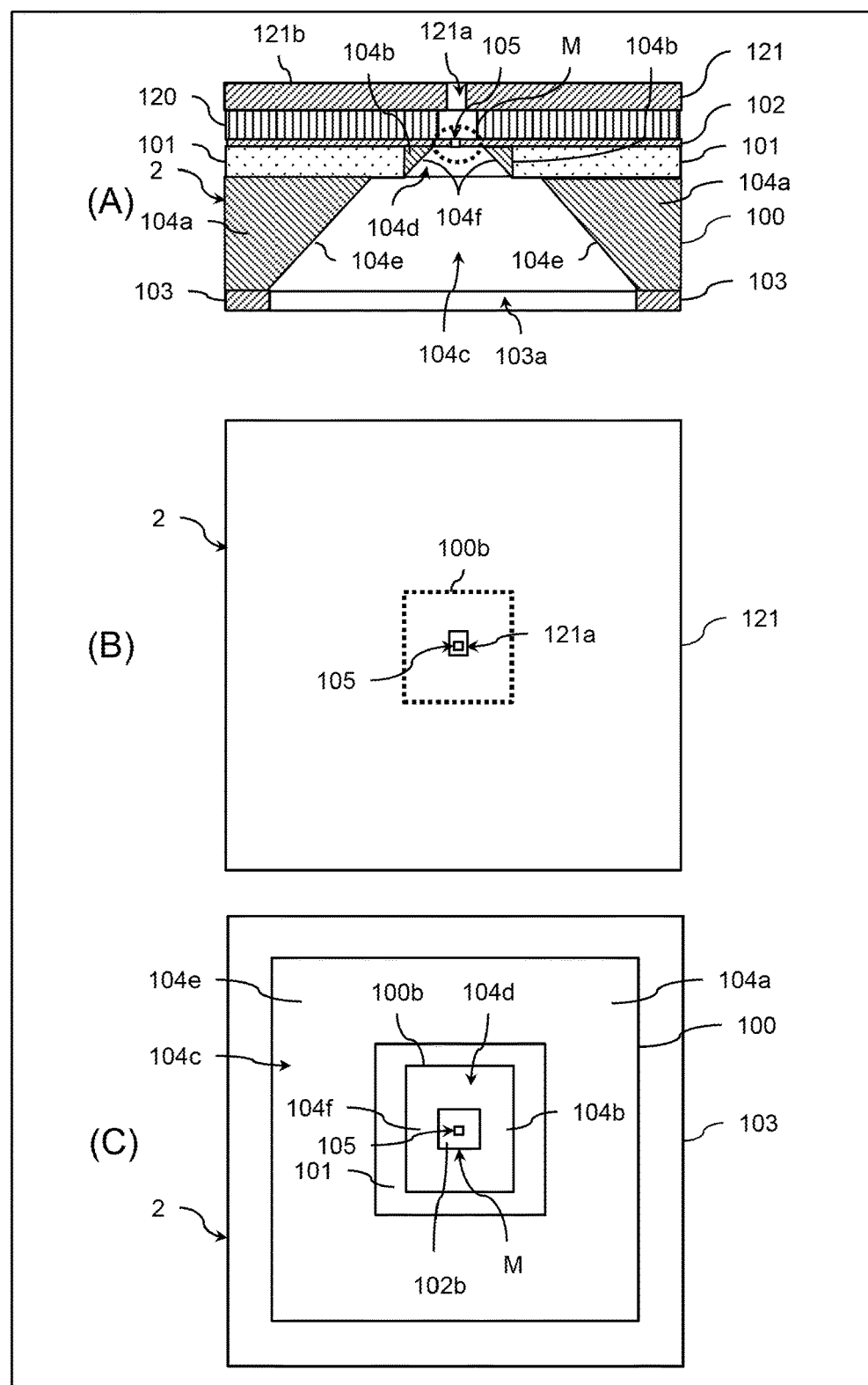
FIG. 16 is an explanatory view for illustrating an example of forming a nanopore 105 in the membrane M in the second embodiment.

FIG. 16 is an explanatory view for illustrating an example of forming a nanopore 105 in the membrane M in the second embodiment. The step of FIG. 16 includes forming the nanopore 105 in the membrane M through use of a known technology (electron beam irradiation process or puncture process) after forming the membrane M in the SiN layer 102 through the steps illustrated in FIG. 9 to FIG. 15. With this, the membrane device 1 becomes a nanopore device 2, and can measure an object to be measured that passes through the nanopore 105.

The manufacturing method according to the second embodiment enables formation of the membrane device 1 (nanopore device 2), in which the thickness of the insulation layer 101 is large, that is, the electrostatic capacitance of the entire device is extremely small, and which has the small membrane M of a region of about 500 nanometers×about 500 nanometers. When the electrostatic capacitance of the entire device becomes low, noise at a time of measurement of ion current flowing when the DNA 110 passes through the nanopore 105 can also be reduced. Further, when the membrane M is reduced in size, there is a decreased probability that inevitable defects (a weak spot and a pinhole caused by, for example, a binding defect between atoms) occurring at a time of formation of the membrane M are present in the membrane M. Thus, the yield of the membrane M is improved.

Further, the nanopore device 2 manufactured by the manufacturing method according to the second embodiment can also be applied with the active drive system illustrated in FIG. 7 or FIG. 8. The poly-Si layer 120 and the SiN layer 121 are formed above the membrane M, but the total thickness of those layers is 250 nanometers in the second embodiment, which is not so large. Therefore, DNA sequencing can be performed under a state in which the DNA 110 is introduced into the nanopore 105 up to a portion of the DNA 110 fixed to the probe substrate 111, which is close to the fixed end 110a.

When the insulation layer 101 having a thickness of 20 micrometers in the second embodiment is formed on the membrane M, a region having a length of at least 20 micrometers from the fixed end 110a of the DNA 110 fixed to the probe substrate 111 cannot be subjected to DNA sequencing by the active drive system. The nanopore device 2 according to the second embodiment has a structure in which the insulation layer 101 having a thickness of 20 micrometers is formed below the membrane M, and only a laminated structure (poly-Si layer 120 and SiN layer 121) required for narrowing the region of the membrane M is formed above the membrane M. This structure is useful for reducing noise of a measurement current at a time of DNA sequencing by the active drive system.

The poly-Si layer 120 may be a $SiO_2$ layer. The thickness of the $SiO_2$ layer is set to, for example, 150 nanometers. The $SiO_2$ layer can be etched with the KOH aqueous solution at a high temperature (from 50° C. to 100° C.). Meanwhile, the SiN layer 102 is hardly damaged by the KOH aqueous solution at a high temperature (from 50° C. to 100° C.), and hence the membrane M can be formed stably. Thus, through use of the $SiO_2$ layer instead of the poly-Si layer 120, the electrostatic capacitance of the nanopore device 2 sandwiched between the aqueous solutions of the upper and lower chambers further decreases at a time of measurement. This can further reduce noise at a time of measurement.

The insulation layers 101 and 103 may be made of materials other than those described in the second embodiment as long as the materials are less liable to be scraped at a time of TMAH or KOH etching. For example, in the above-mentioned example, the insulation layer 101 is formed of the SiO$_2$ layer, but may be formed of a SiN layer. Further, the insulation layer 103 is formed of the SiN layer, but may be formed of a SiO$_2$ layer. In other words, it is only required that the insulation layers 101 and 103 be made of such materials that the etching rate thereof by TMAH or KOH etching is sufficiently low as compared to the etching rate of Si by TMAH or KOH etching. Further, it is only required that the SiN layer 102 be made of a material that is hardly damaged at a time of TMAH or KOH etching, and hafnium oxide (HfO$_2$) or hafnium aluminate (HfAlO) may be used instead of SiN described in the second embodiment.

At a time of etching of the Si substrate 100, an aqueous solution other than the TMAH solution or the KOH solution may be used. For example, it is only required that the aqueous solution be an alkaline aqueous solution that enables crystal anisotropic etching of Si as in the first embodiment, hardly damages the membrane M, and achieves an etching rate of the insulation layers 101 and 103 sufficiently lower than that of Si.

The membrane device 1 formed by the manufacturing method described in the second embodiment has a feature in its finished shape. Specifically, for example, the membrane device 1 includes the Si regions 104a and 104b, in which the inner peripheral surfaces 104e and 104f of the Si substrate 100, each being a {111} plane, are exposed, and the Si region 104b is positioned on the side wall of the insulation layer 101.

In the second embodiment, description is given of an example of the manufacturing method using the Si substrate 100 having the surface 100a of the plane direction {100}, but certain effects can also be obtained by other manufacturing methods. For example, when the Si substrate 100 having the surface 100a of a plane direction {110} is used, the Si substrate 100 is etched perpendicularly from the rear surface 100d by TMAH or KOH etching. Therefore, the openings 104c and 104d do not have such tapered shapes as illustrated in FIG. 16. As a result, the membrane M becomes larger as compared to the case in which the membrane M is formed through use of the Si substrate 100 having the surface 100a of the plane direction {100}. However, the membrane M does not become larger than the area of the island pattern 100b of the Si substrate 100 patterned first.

As described above, the membrane M can be formed stably with satisfactory yield through use of the manufacturing method according to the second embodiment. Further, after the nanopore 105 is formed in the membrane M, noise at a time of measurement of ion current flowing when the DNA 110 passes through the nanopore 105 can also be reduced. Further, the membrane device 1 (nanopore device 2), which is also suitable for being applied with the active drive system at a time of DNA sequencing, can be formed.

Third Embodiment

In a third embodiment of this invention, description is given of a suitable manufacturing method for the membrane device 1, in particular, for reducing noise at a time of measuring an ion current flowing when the DNA passes through a nanopore.

Figure 17:
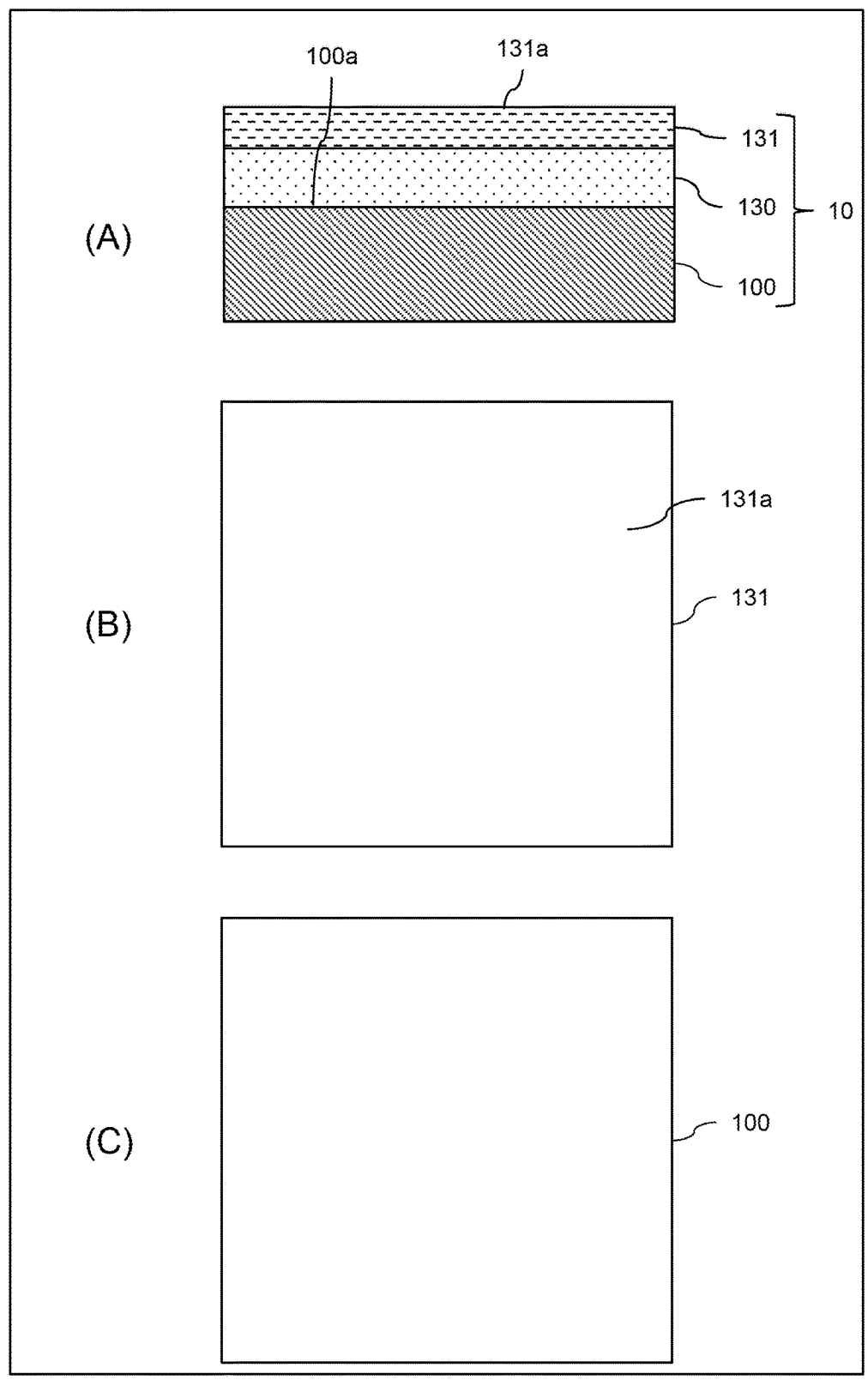
FIG. 17 is an explanatory view for illustrating a method (part 1) of manufacturing a membrane device according to the third embodiment.

FIG. 17 is an explanatory view for illustrating a method (part 1) of manufacturing a membrane device according to the third embodiment. In FIG. 17, in the third embodiment, a silicon-on-insulator (SOI) substrate 10 is prepared. The SOI substrate 10 is a laminated substrate including the Si substrate 100, which is a Si single crystal layer, a SiO$_2$ layer 130, which is an insulation layer formed on the Si substrate 100, and a Si single crystal layer 131, which is formed on the SiO$_2$ layer 130. The thickness of the SiO$_2$ layer 130 is set to, for example, from 1 micrometer to 20 micrometers. The thickness of the SiO$_2$ layer 130 falls within a range that enables reduction of noise at a time of device measurement as described in the second embodiment. The thickness of the Si single crystal layer 131 is set to, for example, 300 nanometers. The thickness of the Si substrate 100 is set to, for example, 725 micrometers (standard thickness of an eight-inch wafer). As the thickness of the SiO$_2$ layer 130 becomes larger, electric noise at a time of current measurement at which the DNA 110 passes through a nanopore can be reduced. The surface 100a of the Si substrate 100 and a surface 131a of the Si single crystal layer 131 each have a plane direction of, for example, {100}.

Figure 18:
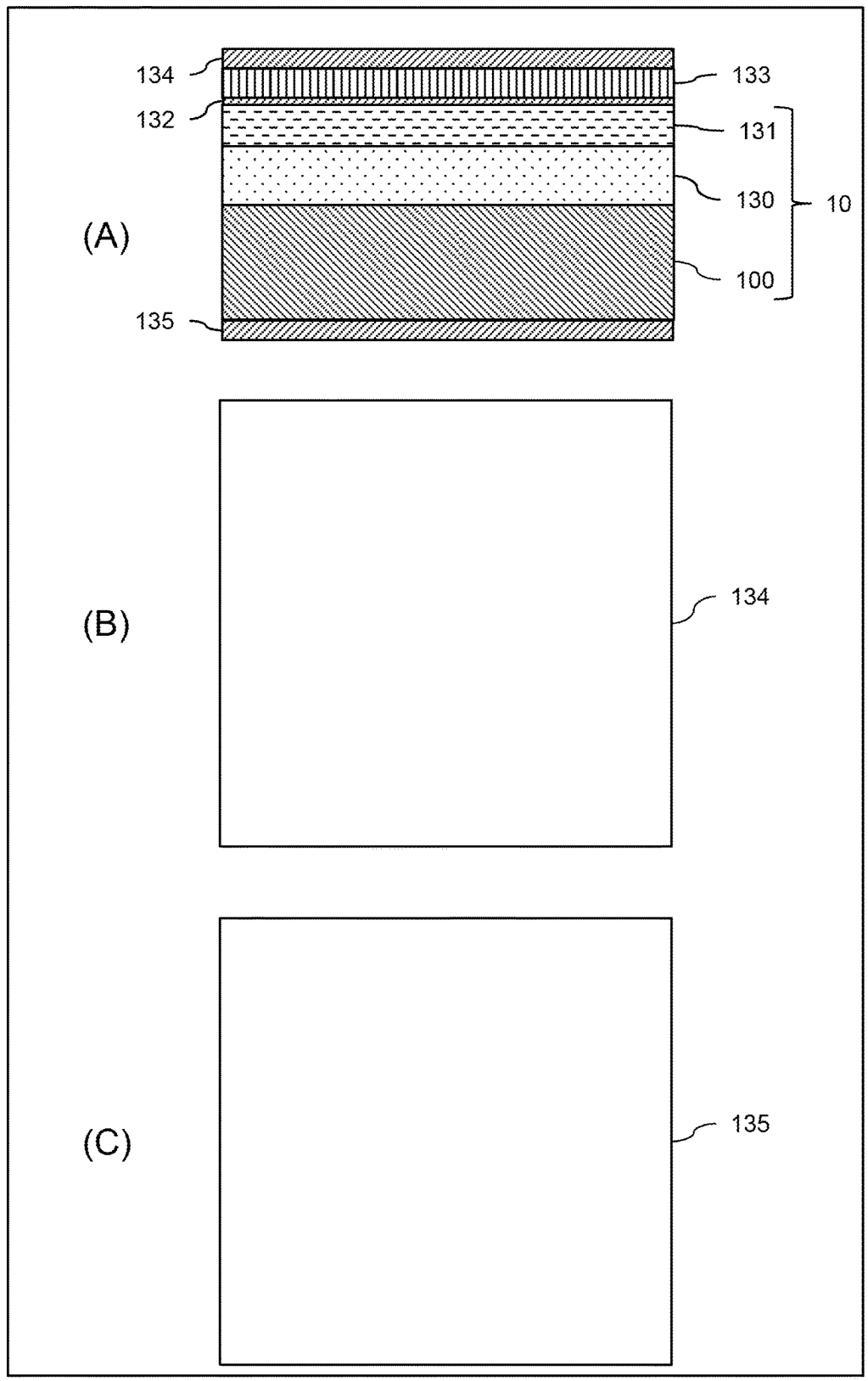
FIG. 18 is an explanatory view for illustrating a method (part 2) of manufacturing a membrane device according to the third embodiment.

FIG. 18 is an explanatory view for illustrating a method (part 2) of manufacturing a membrane device according to the third embodiment. The step of FIG. 18 includes depositing a SiN layer 132 on the Si single crystal layer 131 formed on the SOI substrate 10 prepared in the step of FIG. 17. The thickness of the SiN layer 132 is set to, for example, 3 nanometers. A poly-Si layer 133 and a SiN layer 134 are deposited on the SiN layer 132. The thickness of the poly-Si layer 133 is set to, for example, 150 nanometers, and the thickness of the SiN layer 134 is set to, for example, 100 nanometers. Further, a SiN layer is deposited as an insulation layer 135 on the rear surface 100d of the Si substrate 100. The thickness of the insulation layer 135 is set to, for example, 100 nanometers. The Si single crystal layer 131 has surface flatness more suitable than that of amorphous Si. Thus, when the SiN layer 132 is formed on the Si single crystal layer 131, the membrane M, which has excellent flatness and in which defects can be even more reduced, can be obtained.

Figure 19:
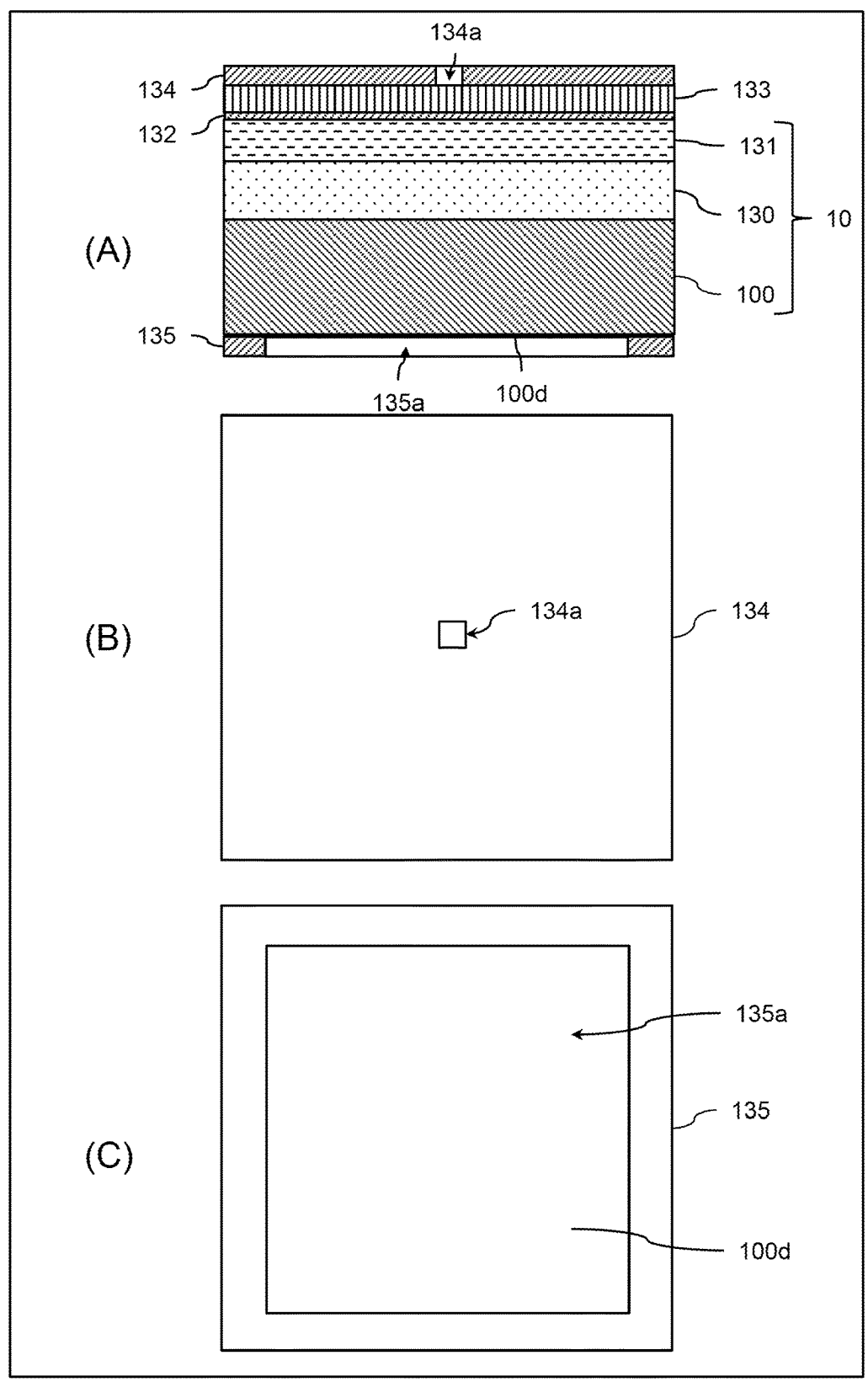
FIG. 19 is an explanatory view for illustrating a method (part 3) of manufacturing a membrane device according to the third embodiment.

FIG. 19 is an explanatory view for illustrating a method (part 3) of manufacturing a membrane device according to the third embodiment. The step of FIG. 19 includes opening a part of the SiN layer 134 obtained in the step of FIG. 18 through use of a lithography technology and a dry etching technology. An opening 134a is a rectangular region having an area of, for example, 100 nanometers×100 nanometers.

Further, the step of FIG. 19 includes patterning the insulation layer 135 on the rear surface 100d side of the Si substrate 100 through use of the general semiconductor lithography technology and dry etching technology as illustrated in parts (A) and (C) of FIG. 19. With this, Si is exposed from a partial region (patterned region 135a) of the rear surface 100d of the Si substrate 100. It is preferred that the size of the patterned region 135a, from which Si is exposed, be adjusted in accordance with the thickness of the Si substrate 100. For example, when the Si substrate 100 having a thickness of 725 micrometers is used, it is preferred that a region having, for example, a vertical dimension of 1,038 micrometers and a horizontal dimension of 1,038 micrometers be patterned as the patterned region 135a. The shape of the patterned region 135a is not limited to a square, and may be another polygon.

Figure 20:
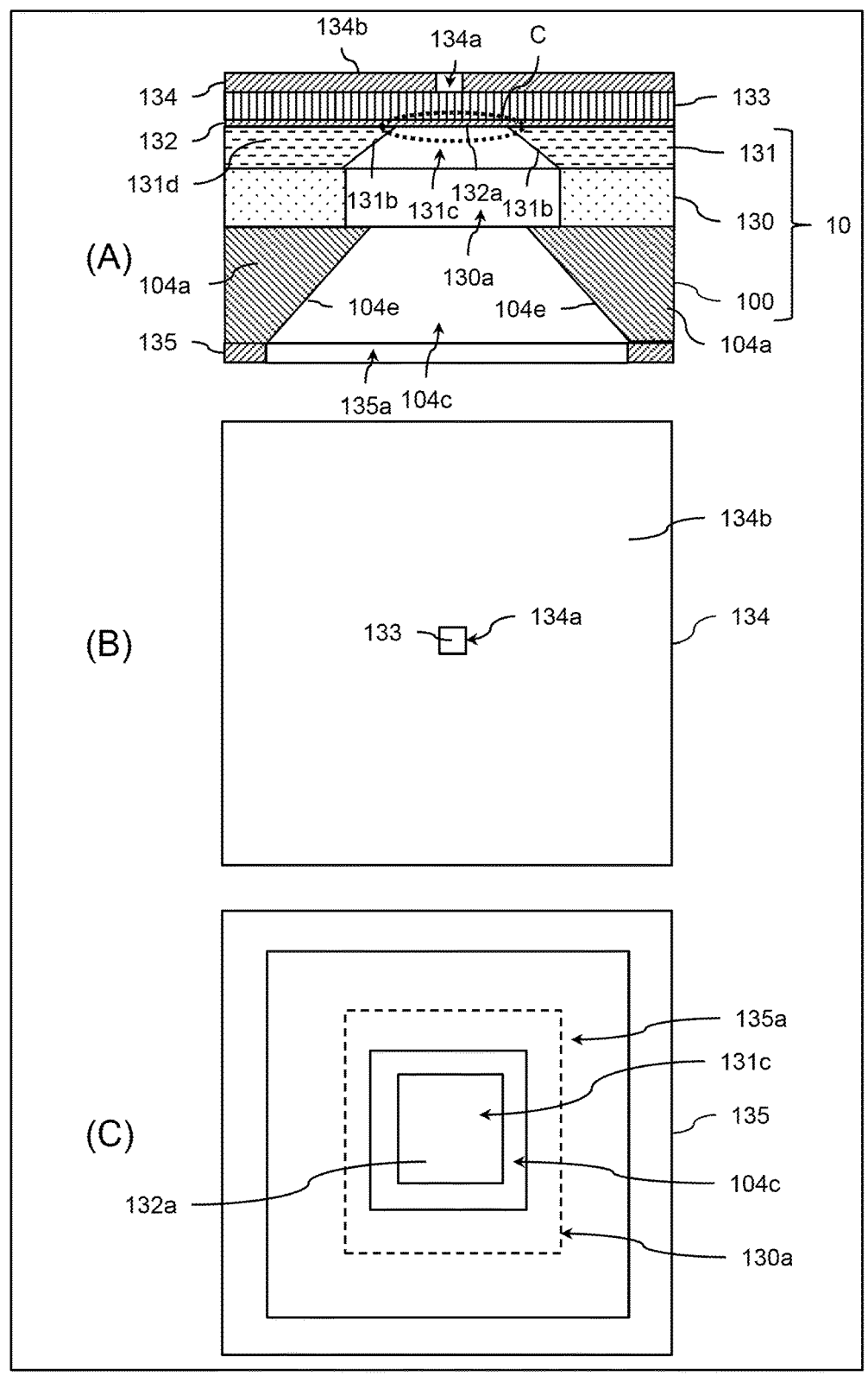
FIG. 20 is an explanatory view for illustrating a method (part 4) of manufacturing a membrane device according to the third embodiment.

FIG. 20 is an explanatory view for illustrating a method (part 4) of manufacturing a membrane device according to the third embodiment. The step of FIG. 20 includes applying an organic protective film (not shown) (for example, Pro-TEK B3 primer and ProTEK B3 manufactured by Brewer Science, Inc. are used) to a surface 134b of the SOI substrate 10 obtained in the step of FIG. 19, and then etching the Si substrate 100 in the SOI substrate 10 with a TMAH solution or a KOH aqueous solution from the rear surface 100d side.

After the Si substrate 100 is etched, the SiO$_2$ layer 130 is etched through use of, for example, hydrofluoric acid (HF) or buffered hydrofluoric acid (BHF). After the SiO$_2$ layer 130 is etched, the Si single crystal layer 131 is etched with the TMAH solution or the KOH aqueous solution. Then, as illustrated in part (A) of FIG. 20, two-stage tapered openings 104c and 131c, in which the inner peripheral surface 104e of the Si substrate 100 and an inner peripheral surface 131b of the Si single crystal layer 131 are exposed, are formed. In other words, through etching, the Si substrate 100 becomes the Si region 104a having the opening 104c formed therein. Through etching, the Si single crystal layer 131 becomes a Si single crystal region 131d having the opening 131c formed therein. The inner peripheral surfaces 104e and 131b are each a {111} plane. Further, through etching, an opening 130a communicating to the openings 104c and 131c is formed in the SiO$_2$ layer 130.

The above-mentioned etching is wet etching. Therefore, an opening diameter becomes smaller along with corrosion in an etching direction (direction from the rear surface 100d to the surface 100a of the Si substrate 100). Then, the inner peripheral surface 104e of the Si region 104a becomes a tapered surface. Similarly, the inner peripheral surface 131b of the Si single crystal region 131d also becomes a tapered surface. In the SiN layer 132, a region defined by the opening diameter of the Si single crystal region 131d on the border of the rear surface 132a serves as a center region C, which becomes a membrane M of the SiN layer 132 in the next step. Then, the organic protective film applied to the surface 134b of the SiN layer 134 is removed through use of a solution that does not damage the SiN layer 134, for example, acetone.

This forms the center region C having a region defined by the Si single crystal region 131d. Through manufacturing of the center region C with the dimensions used in the third embodiment, the center region C becomes a region of from about 50 micrometers to about 100 micrometers square. In the rear surface Si etching process, when the Si substrate 100 is etched from the rear surface 100d side under a state in which the etchant is held in contact only with the wafer rear surface side, it is not required to apply the organic protective film to the surface 134b of the SiN layer 134, and the number of processes can thus be reduced.

Figure 21:
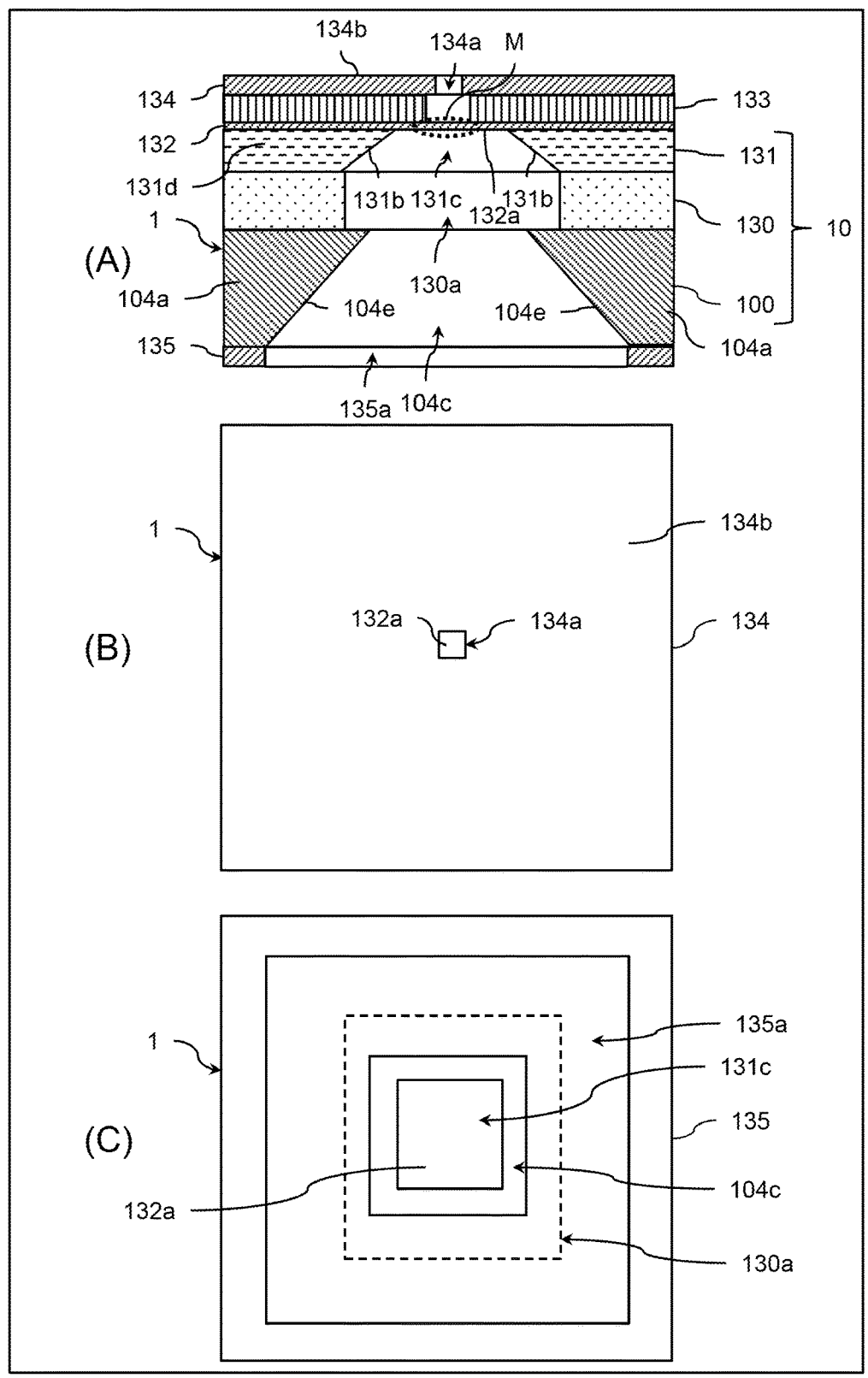
FIG. 21 is an explanatory view for illustrating a method (part 5) of manufacturing a membrane device according to the third embodiment.

FIG. 21 is an explanatory view for illustrating a method (part 5) of manufacturing a membrane device according to the third embodiment. The step of FIG. 21 includes etching a part of the poly-Si layer 133 obtained in the step of FIG. 20 with the SiN layer 134 being a mask through use of the KOH aqueous solution or the TMAH solution. With this, the membrane M having a region defined by the poly-Si layer 133 is formed to complete the membrane device 1. In consideration of variation in thickness of the poly-Si layer 133 and variation in etching rate by the TMAH solution or the KOH aqueous solution, it is preferred that etching in the step of FIG. 20 be performed for a long time period (that is, overetching be performed) as compared to a time period required for etching of the poly-Si layer 133 to a designed thickness. For example, it is preferred that overetching be performed so that the size of the membrane M extends to about a region of 500 nanometers×500 nanometers.

<Example of Forming Nanopore>

Figure 22:
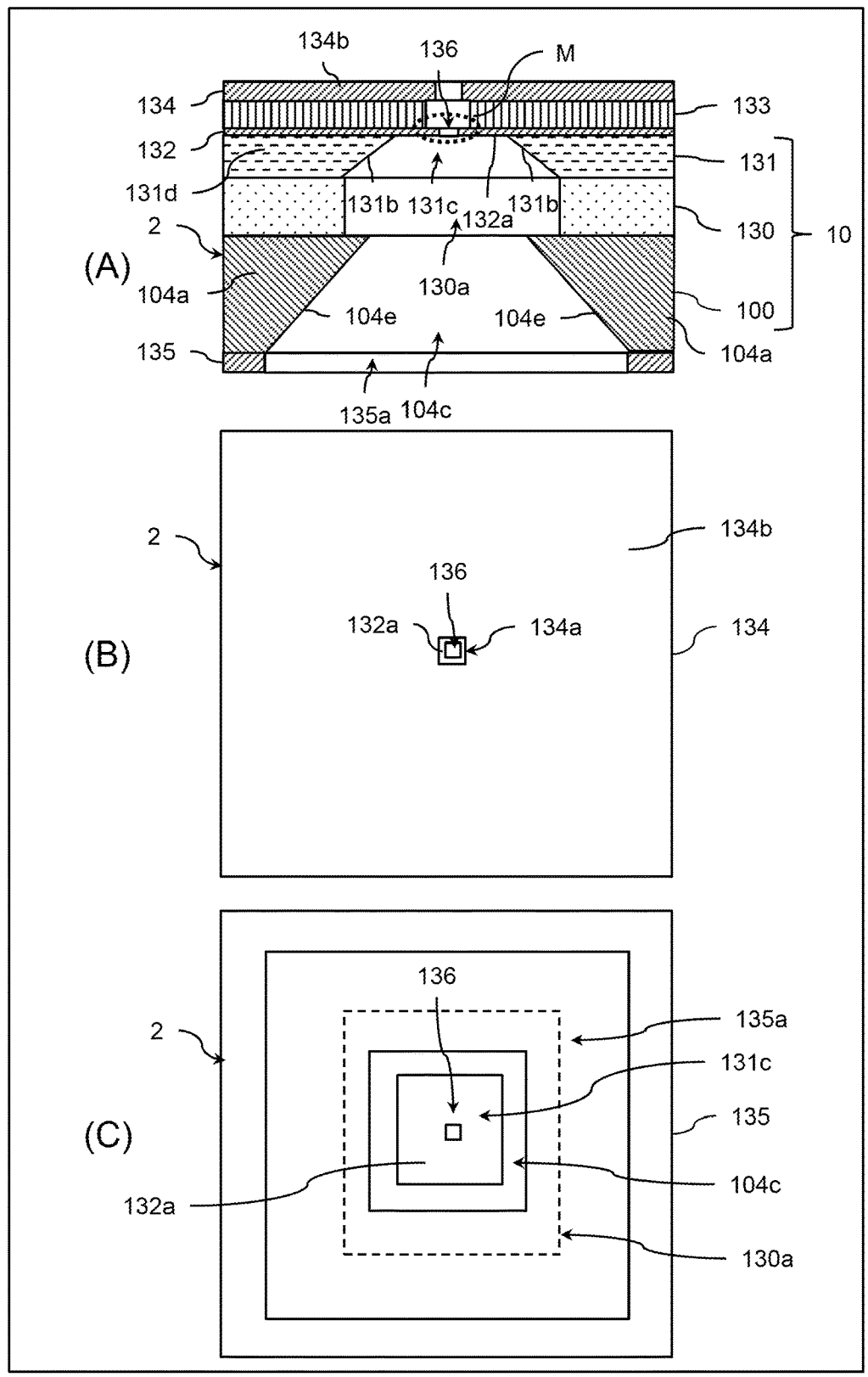
FIG. 22 is an explanatory view for illustrating an example of forming a nanopore in the membrane M in the third embodiment.

FIG. 22 is an explanatory view for illustrating an example of forming a nanopore in the membrane M in the third embodiment. The step of FIG. 22 includes forming a nanopore 136 in the membrane M through use of a known technology (electron beam irradiation process or puncture process) after forming the membrane M through the steps illustrated in FIG. 17 to FIG. 21. With this, the membrane device 1 becomes a nanopore device 2, and can measure an object to be measured that passes through the nanopore 136.

The manufacturing method according to the third embodiment enables formation of the membrane device 1 (nanopore device 2), in which the thickness of the SiO$_2$ layer 130 is large, that is, the electrostatic capacitance of the entire device is extremely small, and which has the small membrane M of a region of about 500 nanometers×about 500 nanometers. When the electrostatic capacitance of the entire device becomes low, noise at a time of measurement of ion current flowing when the DNA 110 passes through the nanopore 136 can also be reduced. Further, when the membrane M is reduced in size, there is a decreased probability that inevitable defects (a weak spot and a pinhole caused by, for example, a binding defect between atoms) occurring at a time of formation of the membrane M are present in the membrane M. Thus, the yield of the membrane M is improved.

Further, the nanopore device 2 manufactured by the manufacturing method according to the third embodiment can also be applied with the active drive system illustrated in FIG. 7 or FIG. 8. The poly-Si layer 133 and the SiN layer 134 are formed on the membrane M, but the total thickness of those layers is 250 nanometers in the third embodiment, which is not so large. Therefore, DNA sequencing can be performed under a state in which the DNA 110 is introduced into the nanopore 136 up to a portion of the DNA 110 fixed to the probe substrate 111, which is close to the fixed end 110a.

When the SiO$_2$ layer 130 having a thickness of from 1 micrometer to 20 micrometers in the third embodiment is formed on the membrane M, a region having a length of from at least 1 micrometer to at least 20 micrometers from the fixed end 110a of the DNA 110 fixed to the probe substrate 111 cannot be subjected to DNA sequencing by the active drive system. The membrane device 1 according to the third embodiment has a structure in which the SiO$_2$ layer 130 having a thickness of from 1 micrometer to 20 micrometers is formed below the membrane M, and only a laminated structure (poly-Si layer 133 and SiN layer 134) required for narrowing the region of the membrane M is formed above the membrane M. This structure is useful for reducing noise of a measurement current at a time of DNA sequencing in the active drive system.

Advantageous points of the manufacturing method according to the third embodiment are described below. In the manufacturing method according to the third embodiment, the etching rate of the SiO$_2$ layer 130 by the KOH or TMAH solution is lower than that of the Si substrate 100. Therefore, when the Si substrate 100 is etched with the KOH or TMAH solution, the thick SiO$_2$ layer 130 serves as an etching stopper. Further, the etching rate of the Si single crystal layer 131 by hydrofluoric acid (HF) or buffered hydrofluoric acid (BHF) is lower than that of the SiO$_2$ layer 130. Thus, when the SiO$_2$ layer 130 is etched with hydrofluoric acid (HF) or buffered hydrofluoric acid (BHF), the Si single crystal layer 131 serves as an etching stopper.

Therefore, when the Si single crystal layer 131 (with a thickness of 300 nanometers in the third embodiment), which is thinner than the Si substrate 100 (with a thickness of 725 micrometers in the third embodiment), is etched after the SiO$_2$ layer 130 is etched, one surface of the membrane M can be exposed from the opening 131c of the Si single crystal layer 131. The Si single crystal layer 131 is thinner than the Si substrate 100, and hence the overetching amount at a time of etching of the Si single crystal layer 131 can also be reduced.

It is assumed that the thickness of the Si single crystal layer 131 is set to 300 nanometers as in the third embodiment. In consideration of variation in etching speed within a wafer surface and variation in thickness of the Si single crystal layer 131, etching is performed under a condition that enables the Si single crystal layer 131 having a thickness of about 450 nanometers to be normally etched. With this, the Si single crystal layer 131 (with a thickness of 300 nanometers) can be etched stably with less etching residue within a wafer surface. In other words, etching can be performed stably by overetching corresponding to 50% of the designed thickness of the Si single crystal layer 131.

Meanwhile, in the method of the first embodiment, the second embodiment, Non Patent Literature 1, or Non Patent Literature 2, the Si substrate is etched without an etching stopper being formed along the path, to thereby expose a one-side portion of a thin film membrane. In this case, the overetching amount for performing etching stably without Si etching residue is required to be larger than that in the third embodiment. This is because the thickness of the Si substrate is, for example, normally 725 micrometers in an eight-inch wafer, and both variation in thickness within one wafer surface and variation in thickness between different wafers are as large as about several micrometers. Therefore, unless the overetching amount at a time of etching of the Si substrate is set to be larger than that in the third embodiment, etching cannot be stably performed without Si etching residue.

Further, in order to etch the Si substrate having a thickness of 725 micrometers, long-time etching (from about 8 hours to about 9 hours at 85° C. with the TMAH solution or the KOH aqueous solution) is required. Therefore, variation in Si etching completion time within a wafer surface, which is caused by variation in etching speed within a wafer surface, is also large. For this reason, unless the overetching amount is set to be larger than that in the third embodiment, etching cannot be performed stably without Si etching residue within the wafer surface.

From the foregoing, when the Si substrate is etched without an etching stopper being formed along the path as in the related-art examples (Non Patent Literature 1 and Non Patent Literature 2), unless at least overetching of from about 50 micrometers to about 100 micrometers is performed, etching cannot be performed stably without Si etching residue. The damage of the SiN film caused by the TMAH solution or the KOH aqueous solution is small, but is not zero. Therefore, as the overetching amount at a time of etching of the Si substrate increases, the probability that the SiN film to be a membrane is damaged increases. As a result, the foregoing causes an initial defect or the like of the membrane, and is a factor for decreasing the yield of the membrane to be manufactured.

In contrast, in the third embodiment, the $SiO_2$ layer 130 serving as an etching stopper is sandwiched between the Si substrate 100 and the Si single crystal layer 131. Therefore, the overetching amount required at a time of final Si etching can be reduced to 1 micrometer or less. Thus, the probability that the membrane M is damaged can be reduced. As a result, the initial defect of the membrane M is reduced, and the yield of the membrane M to be manufactured can be improved.

Further, unlike Non Patent Literature 3, in the third embodiment, the membrane M is formed on the Si single crystal layer 131 by film formation instead of the fishing method. Therefore, the membrane M has excellent flatness and less defects. Further, the process is simple, and a standard semiconductor process using the SOI substrate 10 is used as the process. Therefore, the third embodiment is excellent in mass productivity. Further, in the third embodiment, the exposed surface of the $SiO_2$ layer 130 is smaller than that in Non Patent Literature 3. It is known that the DNA 110 is well adsorbed to $SiO_2$. However, in the third embodiment, the exposed surface of the $SiO_2$ layer 130 is small, and hence the amount of the DNA 110 to be measured that is adsorbed to the $SiO_2$ layer 130 is also small. A phenomenon in which the DNA 110 is adsorbed to the surface of the $SiO_2$ layer 130 and peels therefrom causes noise at a time of measurement of ion current flowing when the DNA 110 passes through the nanopore 136. Thus, the structure in which the exposed surface of the $SiO_2$ layer 130 is small as in the third embodiment is advantageous from the viewpoint of reducing noise at a time of current measurement.

A $SiO_2$ layer can also be used instead of the poly-Si layer 133. The thickness of the $SiO_2$ layer is set to, for example, 150 nanometers. The $SiO_2$ layer can be etched with the KOH aqueous solution at a high temperature (from 50° C. to 100° C.). Meanwhile, the SiN layer 132 is hardly damaged even by the KOH aqueous solution at a high temperature (from 50° C. to 100° C.). Therefore, the membrane M can be formed stably. Thus, through use of the $SiO_2$ layer instead of the poly-Si layer 133, the electrostatic capacitance of the membrane device 1 sandwiched between the aqueous solutions of the upper and lower chambers is further decreased at a time of measurement. Accordingly, noise at a time of measurement can be further reduced.

The insulation layer 135 may be made of a material other than that described in the third embodiment as long as the material is less liable to be scraped at a time of TMAH or KOH etching. For example, in the above-mentioned example, the insulation layer 135 is formed of the SiN layer, but may be formed of a $SiO_2$ layer. In other words, it is only required that the insulation layer 135 be made of such a material that the etching rate of the insulation layer 135 by TMAH or KOH etching is sufficiently low as compared to the etching rate of Si by TMAH or KOH etching. Further, it is only required that the membrane M be made of a material that is hardly damaged at a time of TMAH or KOH etching. For example, $HfO_2$ or HfAlO may be used instead of SiN.

When the Si substrate 100 or the Si single crystal layer 131 is etched, an aqueous solution other than the TMAH solution or the KOH aqueous solution may be used. For example, it is only required that the aqueous solution be an alkaline aqueous solution that enables crystal anisotropy etching of Si, hardly damages the membrane M, and achieves an etching rate of the $SiO_2$ layer 130 and the insulation layer 135 sufficiently lower than that of Si.

The membrane device 1 formed by the manufacturing method described in the third embodiment has a feature in its finished shape. Specifically, for example, the inner peripheral surface 104e of the Si substrate 100 and the inner peripheral surface 131b of the Si single crystal layer 131, each being a {111} plane, are exposed, and the $SiO_2$ layer 130 is sandwiched between the Si substrate 100 and the Si single crystal layer 131.

In the third embodiment, description is given of an example of the manufacturing method using the Si substrate 100 and the Si single crystal layer 131 having the surfaces 100a and 131a of the plane direction {100}, respectively, but certain effects can also be obtained by other manufacturing methods. For example, when the Si substrate 100 having the surface 100a of a plane direction {110} is used, the Si substrate 100 is etched perpendicularly from the surface 100a by TMAH or KOH etching. Therefore, the opening 104c having a tapered shape as illustrated in FIG. 22 is not formed in the Si substrate 100. However, the above-mentioned effects are hardly lost.

As described above, through use of the manufacturing method according to the third embodiment, the membrane M can be formed stably with satisfactory yield. Further, after the nanopore 136 is formed in the membrane M, noise at a time of measurement of ion current flowing when the DNA 110 passes through the nanopore 136 can also be reduced. Further, the membrane device 1 (nanopore device 2), which is also suitable for being applied with the active drive system at a time of DNA sequencing, can be formed.

Fourth Embodiment

In a fourth embodiment of this invention, description is given of a manufacturing method and a structure of a membrane device in which the electrostatic capacitance is lower than that of the membrane device 1 described in the third embodiment and noise at a time of ion current measurement can be further reduced.

Figure 23:
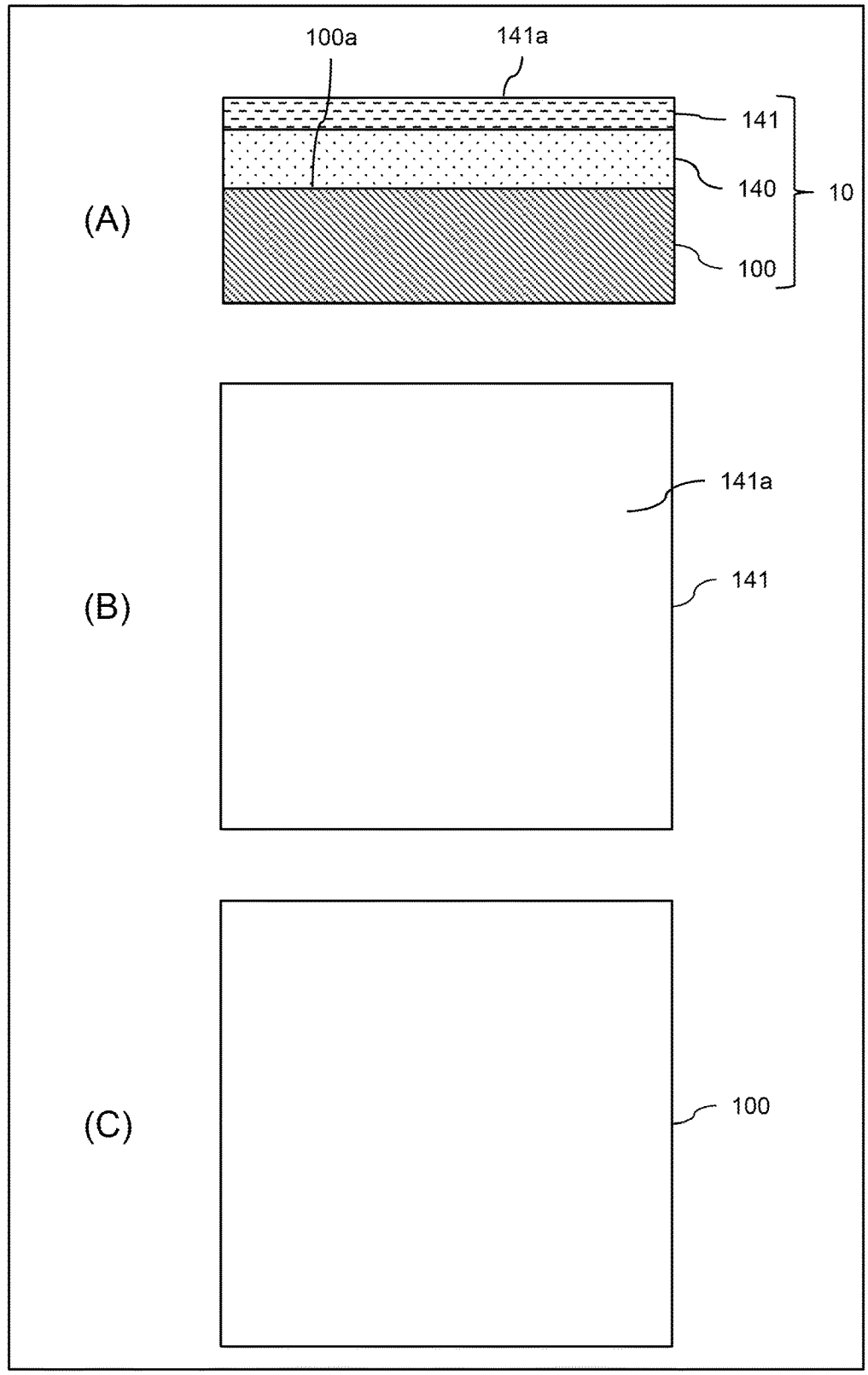
FIG. 23 is an explanatory view for illustrating a method (part 1) of manufacturing a membrane device according to the fourth embodiment.

FIG. 23 is an explanatory view for illustrating a method (part 1) of manufacturing a membrane device according to the fourth embodiment. In FIG. 23, in the fourth embodiment, a SOI substrate 10 is prepared. The SOI substrate 10 is a laminated substrate including the Si substrate 100, which is a Si single crystal layer, a $SiO_2$ layer 140, which is an insulation layer formed on the Si substrate 100, and a Si single crystal layer 141, which is formed on the $SiO_2$ layer 140. The thickness of the $SiO_2$ layer 140 is set to, for example, from 1 micrometer to 20 micrometers. The thickness of the Si single crystal layer 141 is set to, for example, 300 nanometers. The thickness of the Si substrate 100 is set to, for example, 725 micrometers (standard thickness of an eight-inch wafer). As the thickness of the $SiO_2$ layer becomes larger, electric noise at a time of current measurement at which the DNA 110 passes through a nanopore can be reduced. The surface 100a of the Si substrate 100 and a surface 141a of the Si single crystal layer 141 each have a plane direction of, for example, {100}.

Figure 24:
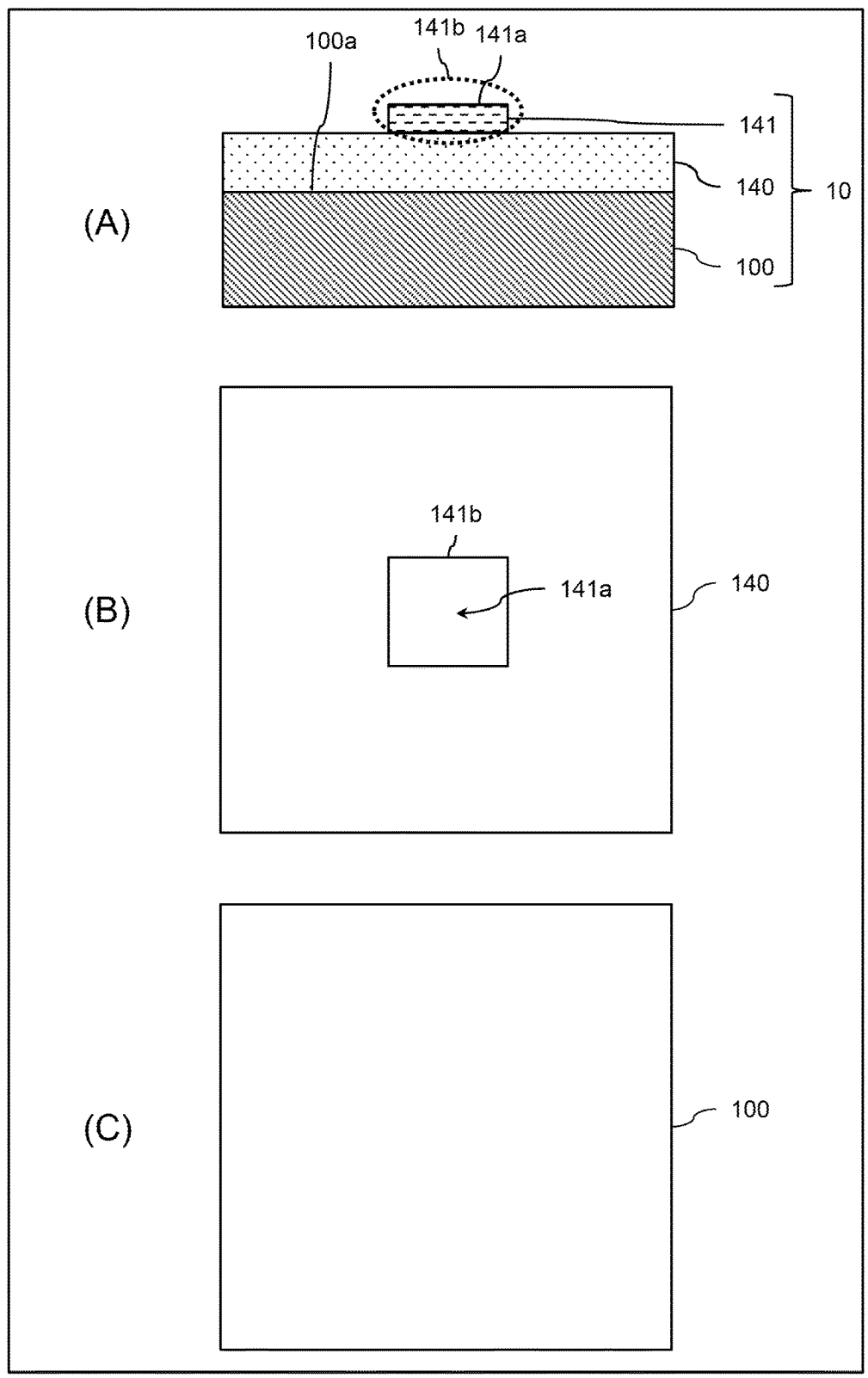
FIG. 24 is an explanatory view for illustrating a method (part 2) of manufacturing the membrane device according to the fourth embodiment.

FIG. 24 is an explanatory view for illustrating a method (part 2) of manufacturing the membrane device according to the fourth embodiment. The step of FIG. 24 includes patterning the Si single crystal layer 141 formed on the SOI substrate 10 obtained in FIG. 23 by dry etching, to thereby form an island pattern 141b of Si. It is assumed that a region of the island pattern 141b of Si has, for example, a vertical dimension of 3 micrometers and a horizontal dimension of 3 micrometers. In other words, through this patterning, the island pattern 141b of Si becomes a remaining portion that remains on the $SiO_2$ layer 140.

Figure 25:
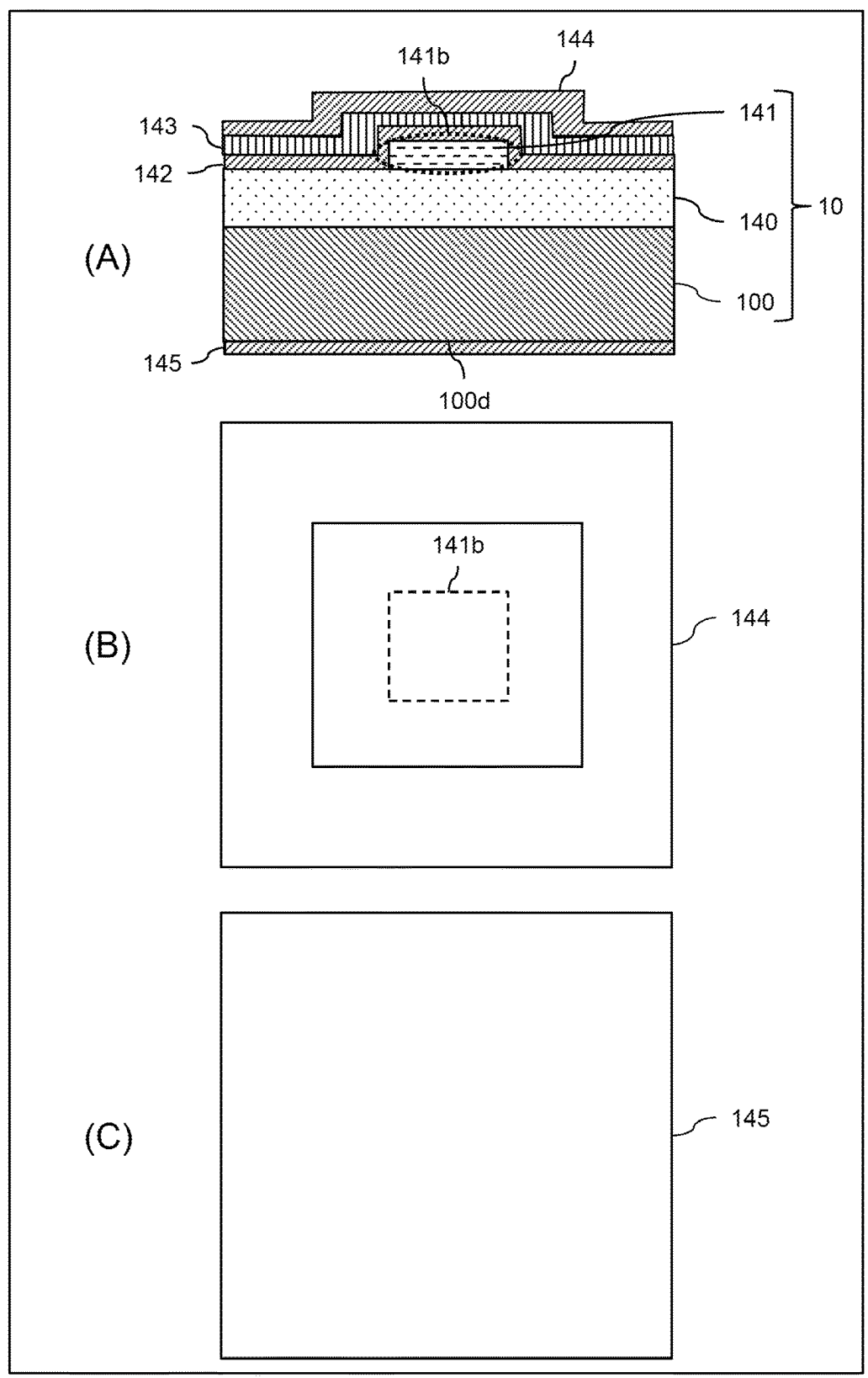
FIG. 25 is an explanatory view for illustrating a method (part 3) of manufacturing a membrane device according to the fourth embodiment.

FIG. 25 is an explanatory view for illustrating a method (part 3) of manufacturing a membrane device according to the fourth embodiment. The step of FIG. 25 includes depositing a SiN layer 142 on the Si single crystal layer 141 and the $SiO_2$ layer 140 formed on the SOI substrate 10 obtained in the step of FIG. 24. The thickness of the SiN layer 142 is set to, for example, 3 nanometers. A poly-Si layer 143 and a SiN layer 144 are deposited on the SiN layer 142. The thickness of the poly-Si layer 143 is set to, for example, 150 nanometers, and the thickness of the SiN layer 144 is set to, for example, 100 nanometers. Further, a SiN layer is deposited as an insulation layer 145 on the rear surface 100d of the Si substrate 100. The thickness of the insulation layer 145 is set to, for example, 100 nanometers. The Si single crystal layer 141 has surface flatness more suitable than that of amorphous Si. Thus, when the SiN layer 142 is formed on the Si single crystal layer 141, the membrane M, which has excellent flatness and in which defects can be even more reduced, can be obtained.

Figure 26:
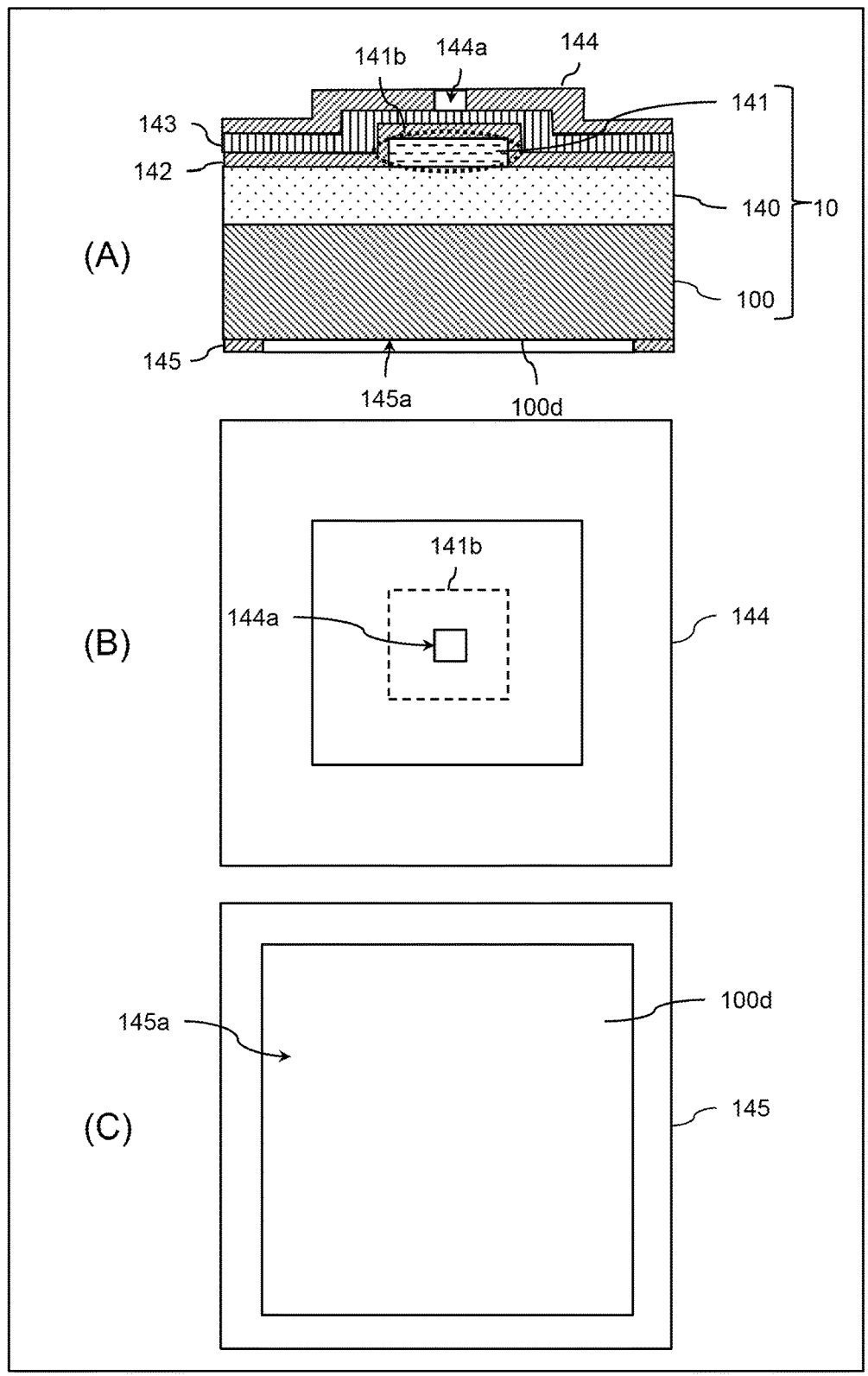
FIG. 26 is an explanatory view for illustrating a method (part 4) of manufacturing a membrane device according to the fourth embodiment.

FIG. 26 is an explanatory view for illustrating a method (part 4) of manufacturing a membrane device according to the fourth embodiment. The step of FIG. 26 includes opening a part of the SiN layer 144 obtained in the step of FIG. 25 through use of a lithography technology and a dry etching technology. An opening 144a is a rectangular region having an area of, for example, 100 nanometers×100 nanometers.

Further, the step of FIG. 26 includes patterning the insulation layer 145 on the rear surface 100d side of the Si substrate 100 through use of the general semiconductor lithography technology and dry etching technology as illustrated in parts (A) and (C) of FIG. 26. With this, Si is exposed from a partial region (patterned region 145a) of the rear surface 100d of the Si substrate 100. It is preferred that the size of the patterned region 145a, from which Si is exposed, be adjusted in accordance with the thickness of the Si substrate 100. For example, when the Si substrate 100 having a thickness of 725 micrometers is used, it is preferred that a region having, for example, a vertical dimension of 1,038 micrometers and a horizontal dimension of 1,038 micrometers be patterned as the patterned region 145a. The shape of the patterned region 145a is not limited to a square, and may be another polygon.

Figure 27:
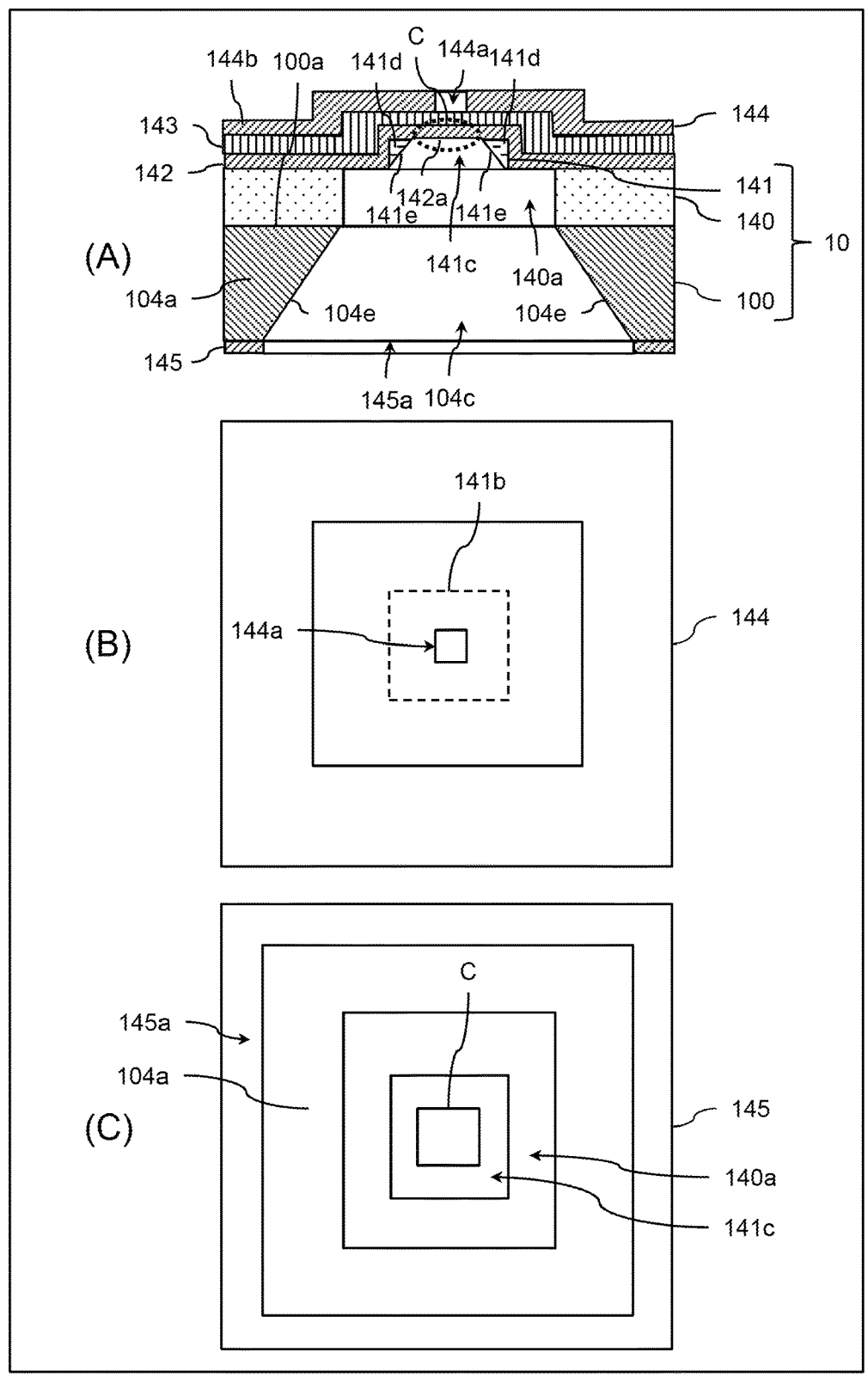
FIG. 27 is an explanatory view for illustrating a method (part 5) of manufacturing a membrane device according to the fourth embodiment.

FIG. 27 is an explanatory view for illustrating a method (part 5) of manufacturing a membrane device according to the fourth embodiment. The step of FIG. 27 includes applying an organic protective film (not shown) (for example, ProTEK B3 primer and ProTEK B3 manufactured by Brewer Science, Inc. are used) to a surface 144b of the SiN layer 144 obtained in the step of FIG. 26, and then etching the Si substrate 100 with a TMAH solution or a KOH aqueous solution from the rear surface 100d side.

After the Si substrate 100 is etched, the $SiO_2$ layer 140 is etched through use of, for example, hydrofluoric acid (HF) or buffered hydrofluoric acid (BHF). After the $SiO_2$ layer 140 is etched, the Si single crystal layer 141 is etched with the TMAH solution or the KOH aqueous solution. Then, as illustrated in part (A) of FIG. 27, two-stage tapered openings 104c and 141c, in which the inner peripheral surface 104e of the Si substrate 100 and an inner peripheral surface 141e of the Si single crystal layer 141 are exposed, are formed. In other words, through etching, the Si substrate 100 becomes the Si region 104a having the opening 104c formed therein. Through etching, the Si single crystal layer 141 becomes a Si single crystal region 141d having the opening 141c formed therein. The inner peripheral surfaces 104e and 141e are each a {111} plane. Further, through etching, an opening 140a communicating to the openings 104c and 141c is formed in the $SiO_2$ layer 140.

The above-mentioned etching is wet etching. Therefore, an opening diameter becomes smaller along with corrosion in an etching direction (direction from the rear surface 100d to the surface 100a of the Si substrate 100). Then, the inner peripheral surface 104e of the Si region 104a becomes a tapered surface. Similarly, the inner peripheral surface 141e of the Si single crystal region 141d also becomes a tapered surface. An opening diameter of the opening 104c on the border of the $SiO_2$ layer 140 is larger than that of the opening 141c on the border of the SiN layer 142. In the SiN layer 142, a region defined by the opening diameter of the opening 141c on the border of the rear surface 142a serves as a center region C, which becomes a membrane M of the SiN layer 142 in the next step. The organic protective film applied to the surface 144b of the SiN layer 144 is removed through use of a solution that does not damage the SiN layer 142, for example, acetone.

With this, the center region C having a region defined by the Si single crystal region 141d is formed. Through manufacturing of the center region C with the dimensions used in the fourth embodiment, the center region C becomes a region of from about 2 micrometers to about 3 micrometers square. In the rear surface Si etching process, when the Si substrate 100 is etched from the rear surface 100d side under a state in which the etchant is held in contact only with the wafer rear surface side, it is not required to apply the organic protective film to the surface 144b of the SiN layer 144, and the number of processes can thus be reduced.

Figure 28:
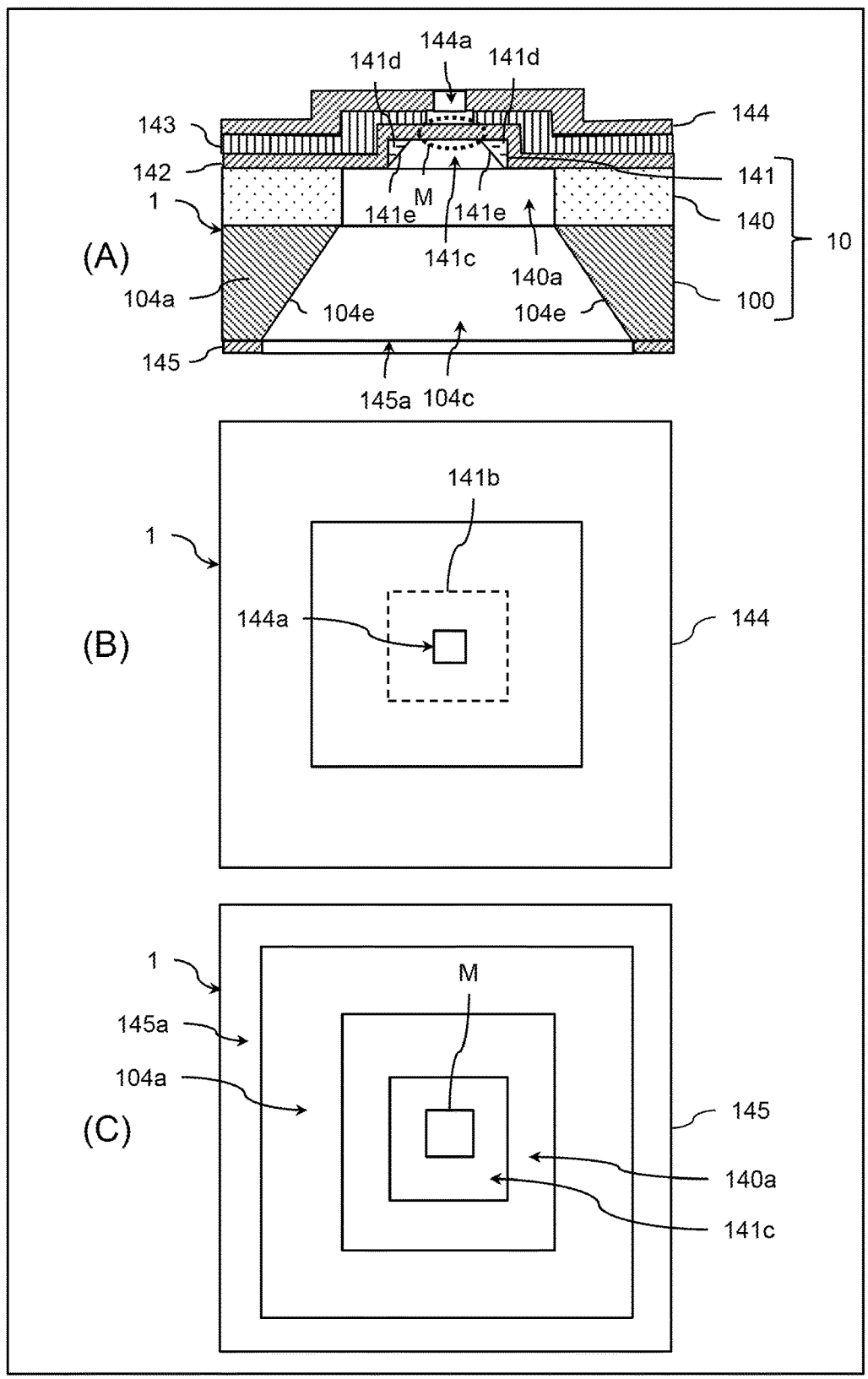
FIG. 28 is an explanatory view for illustrating a method (part 6) of manufacturing a membrane device according to the fourth embodiment.

FIG. 28 is an explanatory view for illustrating a method (part 6) of manufacturing a membrane device according to the fourth embodiment. The step of FIG. 28 includes etching a part of the poly-Si layer 143 obtained in the step of FIG. 27 with the SiN layer 144 being a mask through use of the KOH aqueous solution. With this, the membrane M having a region defined by the poly-Si layer 143 is formed to complete the membrane device 1. In consideration of variation in thickness of the poly-Si layer 143 and variation in etching rate by the KOH aqueous solution, it is preferred that etching in the step of FIG. 28 be performed for a long time period (that is, overetching be performed) as compared to a time period required for etching of the poly-Si layer 143 to a designed thickness. For example, it is preferred that overetching be performed so that the size of the membrane M extends to about a region of 500 nanometers×500 nanometers.

<Example of Forming Nanopore>

Figure 29:
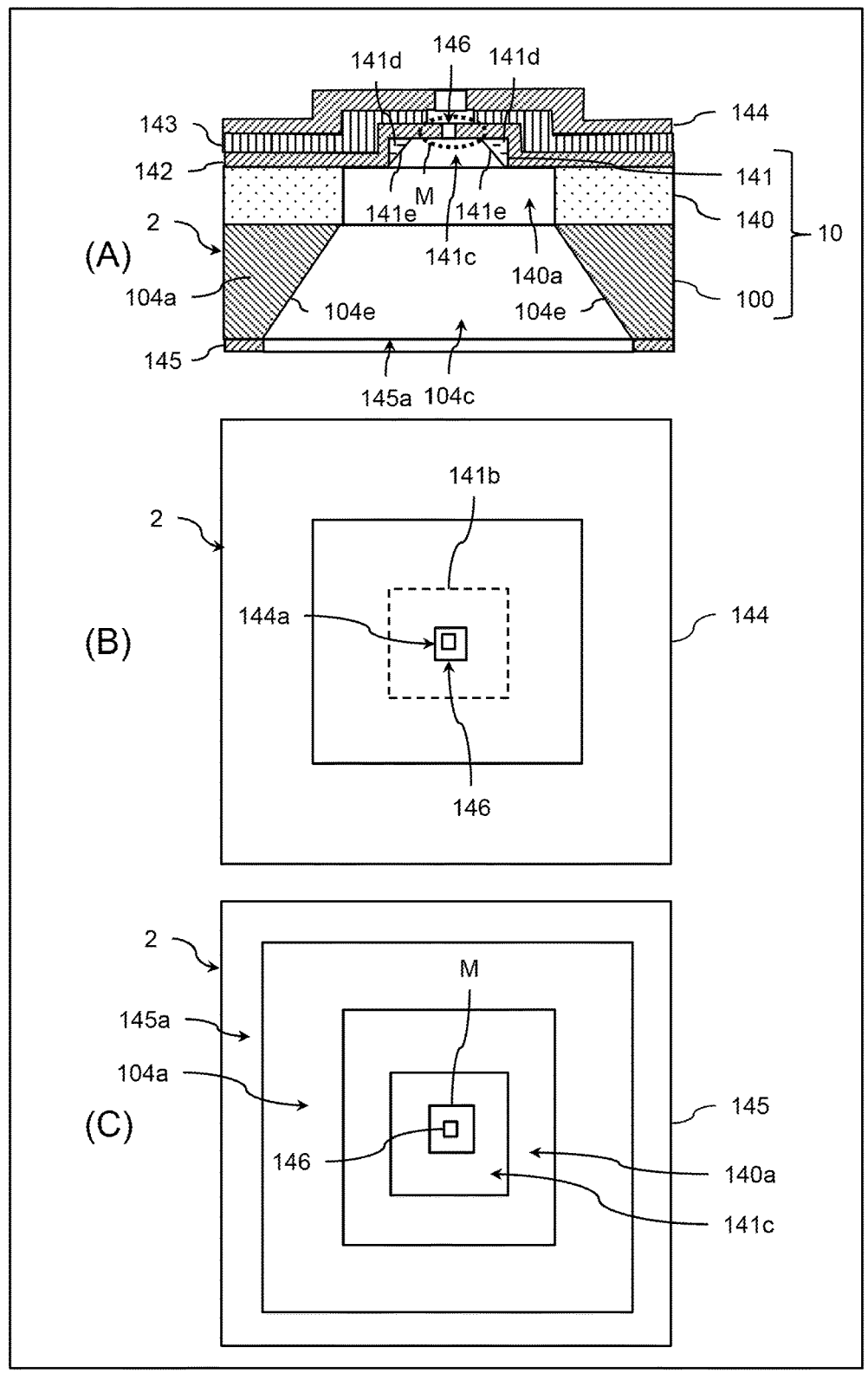
FIG. 29 is an explanatory view for illustrating an example of forming a nanopore in the membrane M in the fourth embodiment.

FIG. 29 is an explanatory view for illustrating an example of forming a nanopore in the membrane M in the fourth embodiment. The step of FIG. 29 includes forming a nanopore 146 in the membrane M through use of a known technology (electron beam irradiation process or puncture process) after forming the membrane M through the steps illustrated in FIG. 23 to FIG. 28. With this, the membrane device 1 becomes a nanopore device 2, and can measure an object to be measured that passes through the nanopore 146.

The manufacturing method according to the fourth embodiment enables formation of the membrane device 1 (nanopore device 2), in which the thickness of the $SiO_2$ layer 140 is large, that is, the electrostatic capacitance of the entire device is extremely small, and which has the small membrane M of a region of about 500 nanometers×about 500 nanometers. When the electrostatic capacitance of the entire device becomes low, noise at a time of measurement of ion current flowing when the DNA 110 passes through the nanopore 146 can also be reduced. Further, when the membrane M is reduced in size, there is a decreased probability that inevitable defects (a weak spot and a pinhole caused by, for example, a binding defect between atoms) occurring at a time of formation of the membrane M are present in the membrane M. Thus, the yield of the membrane M is improved.

Further, the nanopore device 2 manufactured by the manufacturing method according to the fourth embodiment can also be applied with the active drive system illustrated in FIG. 7 or FIG. 8. The poly-Si layer 143 and the SiN layer 144 are formed on the membrane M, but the total thickness of those layers is 250 nanometers in the fourth embodiment, which is not so large. Therefore, DNA sequencing can be performed under a state in which the DNA 110 is introduced into the nanopore 146 up to a portion of the DNA 110 fixed to the probe substrate 111, which is close to the fixed end 110a.

When the $SiO_2$ layer 140 having a thickness of from 1 micrometer to 20 micrometers in the fourth embodiment is formed on the membrane M, a region having a length of from at least 1 micrometer to at least 20 micrometers from the fixed end 110a of the DNA 110 fixed to the probe substrate 111 cannot be subjected to DNA sequencing by the active drive system. The membrane device 1 according to the fourth embodiment has a structure in which the $SiO_2$ layer 140 having a thickness of from 1 micrometer to 20 micrometers is formed below the membrane M, and only a laminated structure (poly-Si layer 143 and SiN layer 144) required for narrowing the region of the membrane M is formed above the membrane M. This structure is useful for reducing noise of a measurement current at a time of DNA sequencing in the active drive system.

Further, as compared to the nanopore device 2 illustrated in FIG. 22, which is described in the third embodiment, the Si single crystal layer 141 accounts for a smaller area in the nanopore device 2 manufactured by the manufacturing method according to the fourth embodiment. Therefore, the electrostatic capacitance between the aqueous solutions filled into both sides of the nanopore device 2 (that is, the electrostatic capacitance of the nanopore device 2) becomes lower than that of the device described in the third embodiment. As a result, noise at a time of measurement of ion current flowing when the DNA 110 passes through the nanopore 146 also further decreases.

Advantageous points of the manufacturing method according to the fourth embodiment are described below. As in the third embodiment, in the manufacturing method according to the fourth embodiment, the etching rate of the $SiO_2$ layer 140 by the KOH or TMAH solution is lower than that of the Si substrate 100. Therefore, when the Si substrate 100 is etched with the KOH or TMAH solution, the thick $SiO_2$ layer 140 serves as an etching stopper. Further, the etching rate of the Si single crystal layer 141 by hydrofluoric acid (HF) or buffered hydrofluoric acid (BHF) is lower than that of the $SiO_2$ layer 140. Thus, when the $SiO_2$ layer 140 is etched with hydrofluoric acid (HF) or buffered hydrofluoric acid (BHF), the Si single crystal layer 141 serves as an etching stopper.

Therefore, when the Si single crystal layer 141 (with a thickness of 300 nanometers in the fourth embodiment), which is thinner than the Si substrate 100 (with a thickness of 725 micrometers in the fourth embodiment), is etched after the $SiO_2$ layer 140 is etched, one surface of the membrane M can be exposed. The Si single crystal layer 141 is thinner than the Si substrate 100, and hence the overetching amount at a time of etching of the Si single crystal layer 141 can also be reduced.

It is assumed that the thickness of the Si single crystal layer 141 is set to 300 nanometers as in the fourth embodiment. In consideration of variation in etching speed within a wafer surface and variation in thickness of the Si single crystal layer 141, etching is performed under a condition that enables the Si single crystal layer 141 having a thickness of about 450 nanometers to be normally etched. With this, the Si single crystal layer 141 (with a thickness of 300 nanometers) can be etched stably with less etching residue within a wafer surface. In other words, etching can be performed stably by overetching corresponding to 50% of the designed thickness of the Si single crystal layer 141.

Meanwhile, in the method of the first embodiment, the second embodiment, Non Patent Literature 1, or Non Patent Literature 2, the Si substrate is etched without an etching stopper being formed along the path, to thereby expose a one-side portion of a thin film membrane. In this case, the overetching amount for performing etching stably without Si etching residue is required to be larger than that in the fourth embodiment. This is because the thickness of the Si substrate is, for example, normally 725 micrometers in an eight-inch wafer, and both variation in thickness within one wafer surface and variation in thickness between different wafers are as large as about several micrometers. Therefore, unless the overetching amount at a time of etching of the Si substrate is set to be larger than that in the fourth embodiment, etching cannot be stably performed without Si etching residue.

Further, in order to etch the Si substrate having a thickness of 725 micrometers, long-time etching (from about 8 hours to about 9 hours at 85° C. with the TMAH solution or the KOH aqueous solution) is required. Therefore, variation in Si etching completion time within a wafer surface, which is caused by variation in etching speed within a wafer surface, is also large. For this reason, unless the overetching amount is set to be larger than that in the fourth embodiment, etching cannot be performed stably without Si etching residue within the wafer surface.

From the foregoing, when the Si substrate is etched without an etching stopper being formed along the path as in the related-art examples (Non Patent Literature 1 and Non Patent Literature 2), unless at least overetching of from about 50 micrometers to about 100 micrometers is performed, etching cannot be performed stably without Si etching residue. The damage of the SiN film caused by the TMAH solution or the KOH aqueous solution is small, but is not zero. Therefore, as the overetching amount at a time of etching of the Si substrate increases, the probability that the SiN film to be a membrane is damaged increases. As a result, the foregoing causes an initial defect or the like of the membrane, and is a factor for decreasing the yield of the membrane to be manufactured.

In contrast, in the fourth embodiment, the $SiO_2$ layer 140 serving as an etching stopper is sandwiched between the Si substrate 100 and the Si single crystal layer 141. Therefore, the overetching amount required at a time of final Si etching can be reduced to 1 micrometer or less. Thus, the probability that the membrane M is damaged can be reduced. As a result, the initial defect of the membrane M is reduced, and the yield of the membrane M to be manufactured can be improved.

Further, unlike Non Patent Literature 3, in the fourth embodiment, the membrane M is formed on the Si single crystal layer 141 by film formation instead of the fishing method. Therefore, the membrane M has excellent flatness and less defects. Further, the process is simple, and a standard semiconductor process using the SOI substrate 10 is used as the process. Therefore, the fourth embodiment is excellent in mass productivity. Further, in the fourth embodiment, the exposed surface of the $SiO_2$ layer 140 is smaller than that in Non Patent Literature 3. It is known that the DNA 110 is well adsorbed to $SiO_2$. However, in the fourth embodiment, the exposed surface of the $SiO_2$ layer 140 is small, and hence the amount of the DNA 110 to be measured that is adsorbed to the $SiO_2$ layer 140, is also small. A phenomenon in which the DNA 110 is adsorbed to the surface of the $SiO_2$ layer 140 and peels therefrom causes noise at a time of measurement of ion current flowing when the DNA 110 passes through the nanopore 146. Thus, the structure in which the exposed surface of the $SiO_2$ layer 140 is small as in the fourth embodiment is advantageous from the viewpoint of reducing noise at a time of current measurement.

A $SiO_2$ layer can also be used instead of the poly-Si layer 143. The thickness of the $SiO_2$ layer is set to, for example, 150 nanometers. The $SiO_2$ layer can be etched with the KOH aqueous solution at a high temperature (from 50° C. to 100° C.). Meanwhile, the SiN layer 142 is hardly damaged even by the KOH aqueous solution at a high temperature (from 50° C. to 100° C.). Therefore, the membrane M can be formed stably. Thus, through use of the $SiO_2$ layer instead of the poly-Si layer 143, the electrostatic capacitance of the membrane device 1 sandwiched between the aqueous solutions of the upper and lower chambers is further decreased at a time of measurement. Accordingly, noise at a time of measurement can be further reduced.

The insulation layer 145 may be made of a material other than that described in the fourth embodiment as long as the material is less liable to be scraped at a time of TMAH or KOH etching. For example, in the above-mentioned example, the insulation layer 145 is formed of the SiN layer, but may be formed of a $SiO_2$ layer. In other words, it is only required that the insulation layer 145 be made of such a material that the etching rate of the insulation layer 145 by TMAH or KOH etching is sufficiently low as compared to the etching rate of Si by TMAH or KOH etching. Further, it is only required that the membrane M be made of a material that is hardly damaged at a time of TMAH or KOH etching. For example, $HfO_2$ or HfAlO may be used instead of SiN.

When the Si substrate 100 or the Si single crystal layer 141 is etched, an aqueous solution other than the TMAH solution or the KOH aqueous solution may be used. For example, it is only required that the aqueous solution be an alkaline aqueous solution that enables crystal anisotropy etching of Si, hardly damages the membrane M, and achieves an etching rate of the $SiO_2$ layer 140 and the insulation layer 145 sufficiently lower than that of Si.

The membrane device 1 formed by the manufacturing method described in the fourth embodiment has a feature in its finished shape. Specifically, for example, the inner peripheral surface 104e of the Si substrate 100 and the inner peripheral surface 141e of the Si single crystal layer 141, each being a {111} plane, are exposed, and the $SiO_2$ layer 140 is sandwiched between the Si substrate 100 and the Si single crystal layer 141.

Further, the Si single crystal layer 141 is present so as to form a side wall in a level difference portion of the SiN layer 142.

In the fourth embodiment, description is given of an example of the manufacturing method using the Si substrate 100 and the Si single crystal layer 141 having the surfaces 100a and 141a of the plane direction {100}, respectively, but certain effects can also be obtained by other manufacturing methods. For example, when the Si substrate 100 having the surface 100a of a plane direction {110} is used, the Si substrate 100 is etched perpendicularly from the surface 100a by TMAH or KOH etching. Therefore, the opening 104c having a tapered shape as illustrated in FIG. 29 is not formed in the Si substrate 100. Accordingly, the opening 104c of the Si substrate 100 is not formed to have a tapered shape. However, the above-mentioned effects are hardly lost.

As described above, through use of the manufacturing method according to the fourth embodiment, the membrane M can be formed stably with satisfactory yield. Further, after the nanopore 146 is formed in the membrane M, noise at a time of measurement of ion current flowing when the DNA 110 passes through the nanopore 146 can also be reduced. Further, the membrane device 1 (nanopore device 2), which is also suitable for being applied with the active drive system at a time of DNA sequencing, can be formed.

Fifth Embodiment

In a fifth embodiment of this invention, description is given of another manufacturing method exhibiting effects substantially equal to those of the third embodiment. In the third embodiment, the SOI substrate 10 is used, but in the fifth embodiment, the manufacturing method using the Si substrate 100 is described. The Si substrate 100 is more inexpensive than the SOI substrate 10, and hence cost of the membrane device 1 can be reduced.

Figure 30:
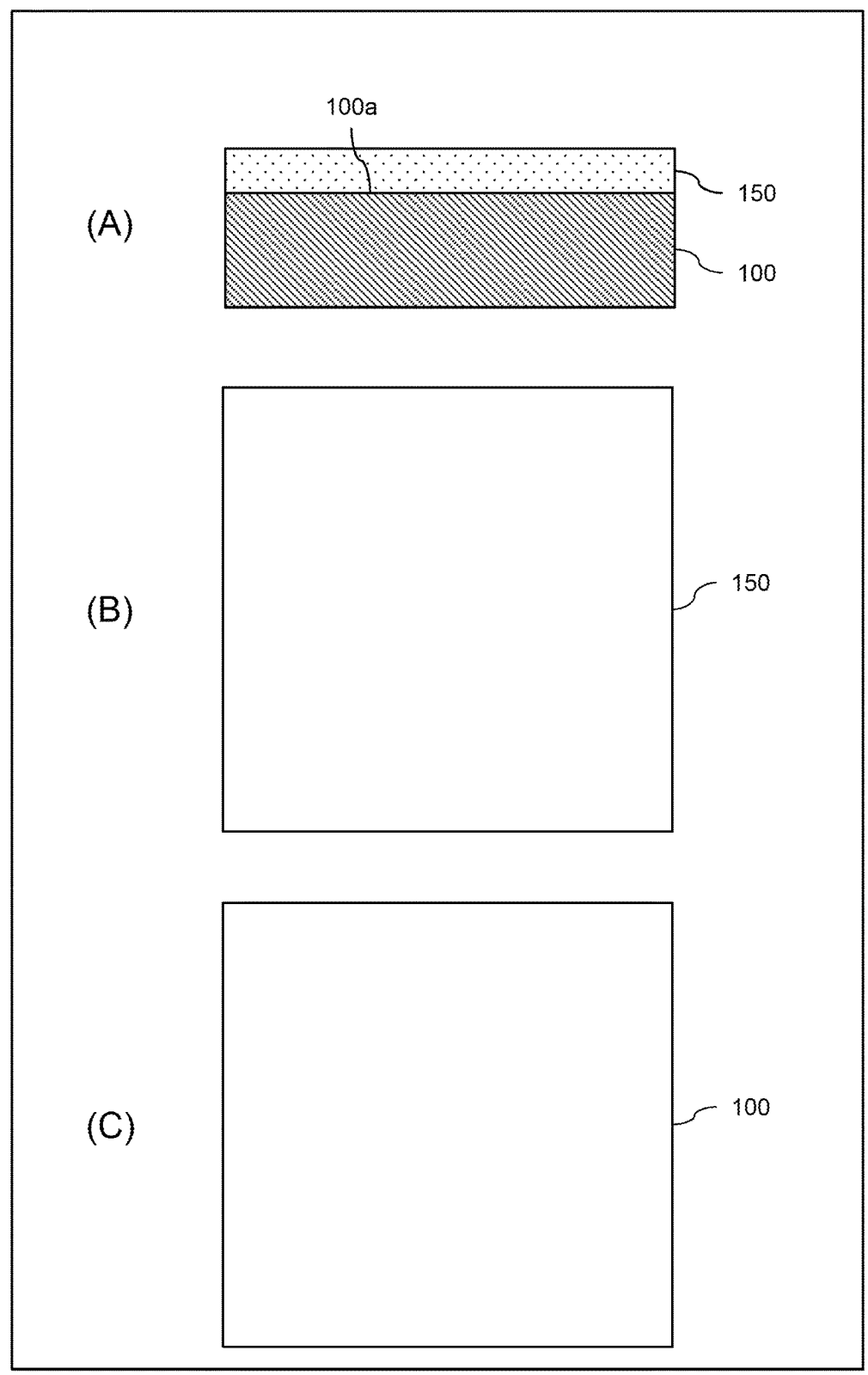
FIG. 30 is an explanatory view for illustrating a method (part 1) of manufacturing a membrane device according to the fifth embodiment.

FIG. 30 is an explanatory view for illustrating a method (part 1) of manufacturing a membrane device according to the fifth embodiment. In FIG. 30, the Si substrate 100 having a surface 100a of a plane direction {100} is prepared. A SiO$_2$ layer 150, which is an insulation layer, is deposited so as to have a thickness of from 1 micrometer to 20 micrometers on the Si substrate 100.

Figure 31:
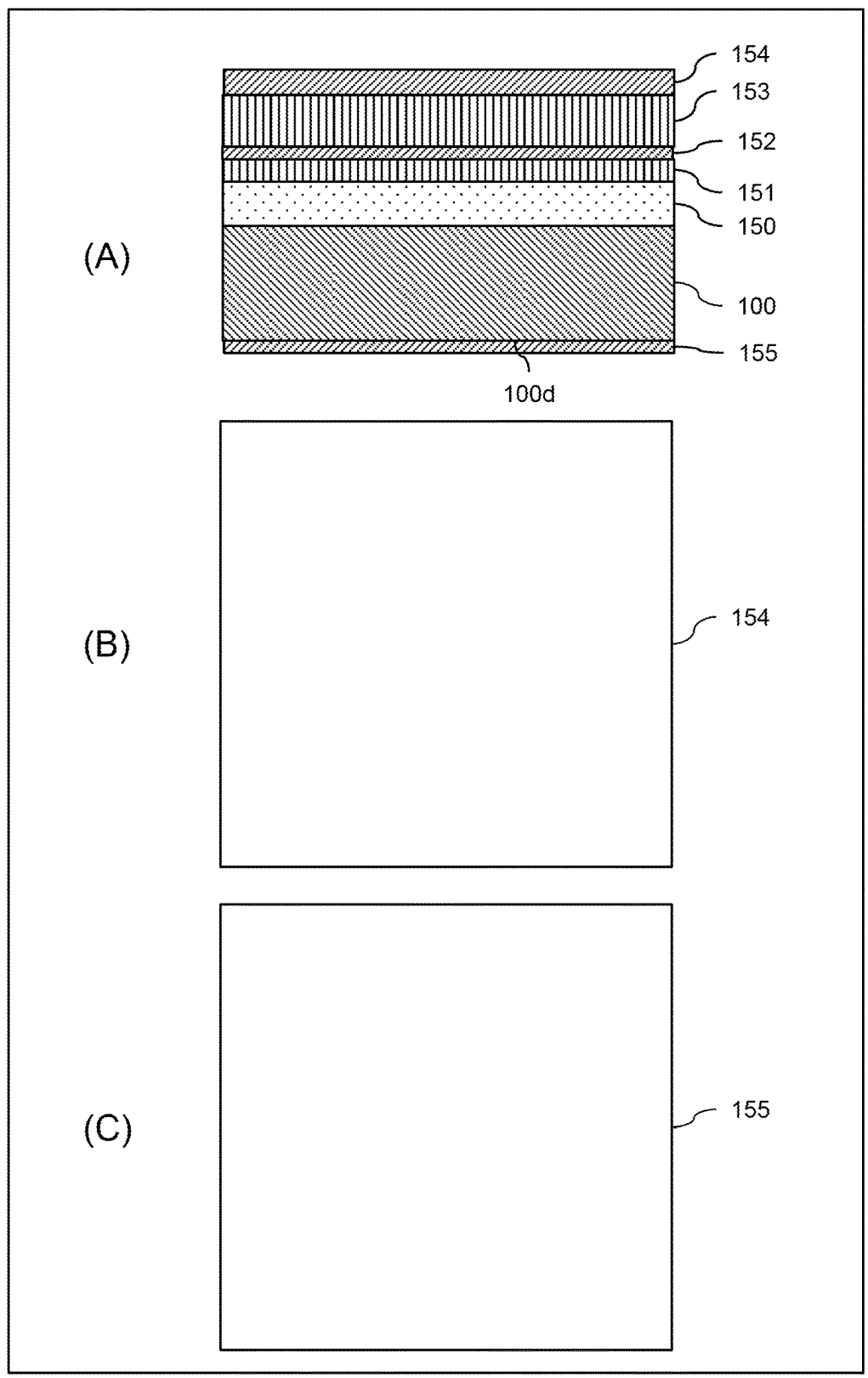
FIG. 31 is an explanatory view for illustrating a method (part 2) of manufacturing a membrane device according to the fifth embodiment.

FIG. 31 is an explanatory view for illustrating a method (part 2) of manufacturing a membrane device according to the fifth embodiment. The step of FIG. 31 includes depositing a poly-Si layer 151, a SiN layer 152, a poly-Si layer 153, and a SiN layer 154 on the SiO$_2$ layer 150 formed on the Si substrate 100 illustrated in FIG. 30. The thickness of the poly-Si layer 151 is set to, for example, 100 nanometers, the thickness of the SiN layer 152 is set to, for example, 3 nanometers, the thickness of the poly-Si layer 153 is set to, for example, 150 nanometers, and the thickness of the SiN layer 154 is set to, for example, 100 nanometers. Further, a SiN layer is deposited as an insulation layer 155 on the rear surface 100d of the Si substrate 100. The thickness of the insulation layer 155 is set to, for example, 100 nanometers.

Figure 32:
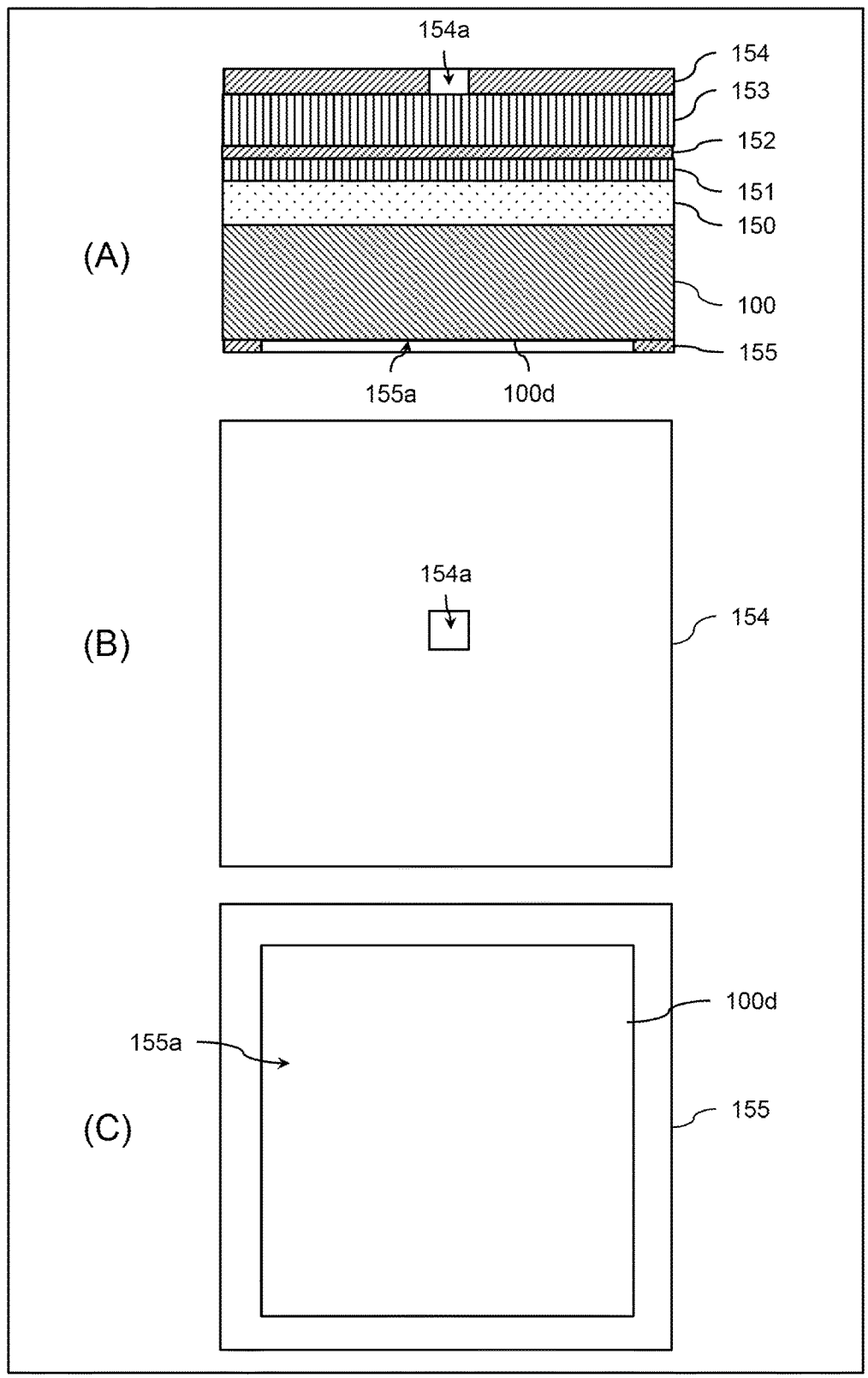
FIG. 32 is an explanatory view for illustrating a method (part 3) of manufacturing a membrane device according to the fifth embodiment.

FIG. 32 is an explanatory view for illustrating a method (part 3) of manufacturing a membrane device according to the fifth embodiment. The step of FIG. 32 includes opening a part of the SiN layer 154 obtained in the step of FIG. 31 through use of a lithography technology and a dry etching technology. An opening 154a is a rectangular region having an area of, for example, 100 nanometers×100 nanometers.

Further, the step of FIG. 32 includes patterning the insulation layer 155 on the rear surface 100d side of the Si substrate 100 through use of the general semiconductor lithography technology and dry etching technology as illustrated in parts (A) and (C) of FIG. 32. With this, Si is exposed from a partial region (patterned region 155a) of the rear surface 100d of the Si substrate 100. It is preferred that the size of the patterned region 155a, from which Si is exposed, be adjusted in accordance with the thickness of the Si substrate 100. For example, when the Si substrate 100 having a thickness of 725 micrometers is used, it is preferred that a region having, for example, a vertical dimension of 1,038 micrometers and a horizontal dimension of 1,038 micrometers be patterned as the patterned region 155a. The shape of the patterned region 155a is not limited to a square, and may be another polygon.

Figure 33:
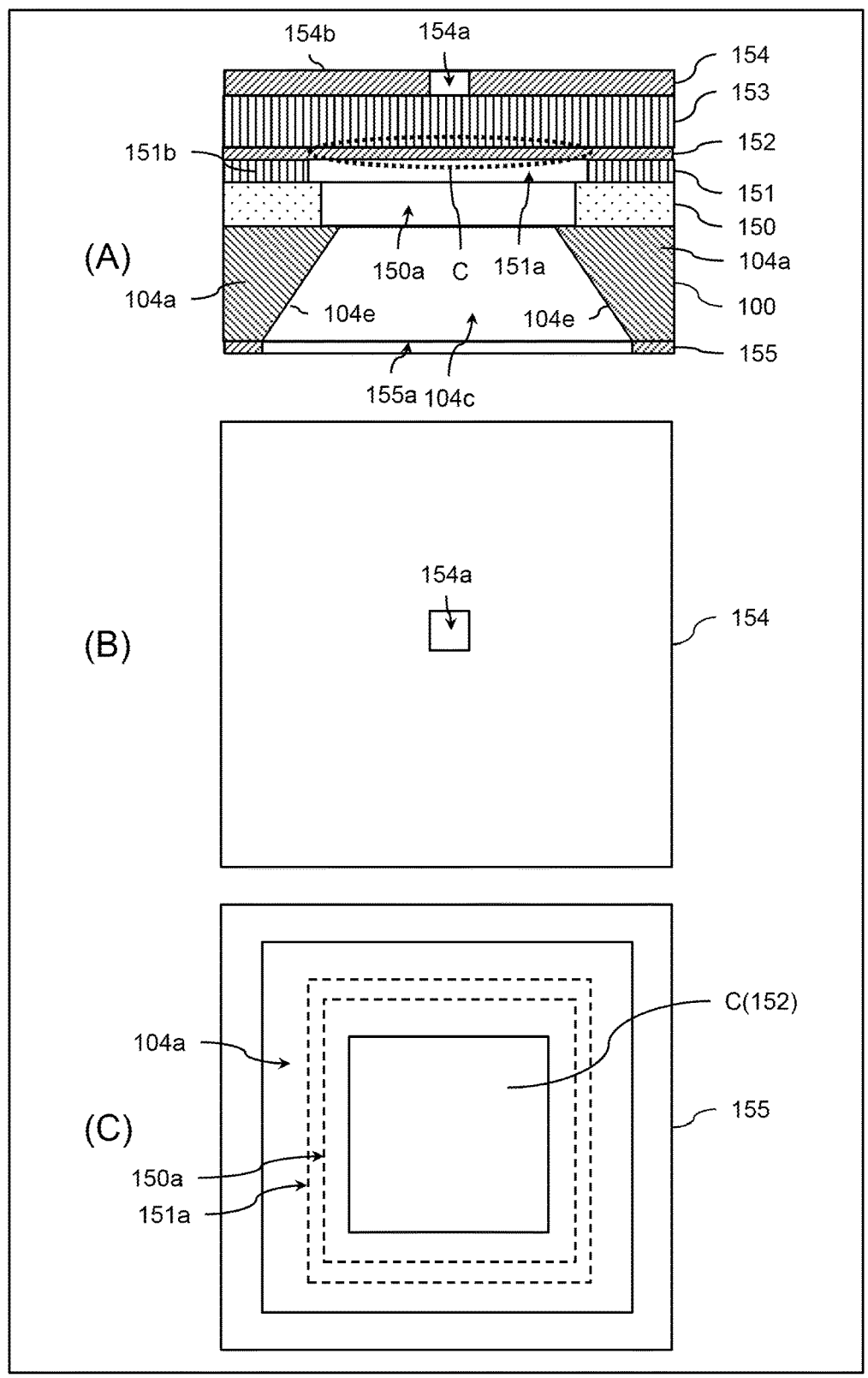
FIG. 33 is an explanatory view for illustrating a method (part 4) of manufacturing a membrane device according to the fifth embodiment.

FIG. 33 is an explanatory view for illustrating a method (part 4) of manufacturing a membrane device according to the fifth embodiment. The step of FIG. 33 includes applying an organic protective film (not shown) (for example, Pro-TEK B3 primer and ProTEK B3 manufactured by Brewer Science, Inc. are used) to a surface 154b of the SiN layer 154 obtained in the step of FIG. 32, and then etching the Si substrate 100 with a TMAH solution or a KOH aqueous solution from the rear surface 100d side.

After the Si substrate 100 is etched, the SiO$_2$ layer 150 is etched through use of, for example, hydrofluoric acid (HF) or buffered hydrofluoric acid (BHF). After the SiO$_2$ layer 150 is etched, the poly-Si layer 151 is etched with the TMAH solution or the KOH aqueous solution. Then, as illustrated in part (A) of FIG. 33, a tapered opening 104c, in which the inner peripheral surface 104e of the Si substrate 100 is exposed, is formed. In other words, through etching, the Si substrate 100 becomes the Si region 104a having the opening 104c formed therein. The inner peripheral surface 104e is a {111} plane. Through etching, openings 150a and 151a are formed in the SiO$_2$ layer 150 and the poly-Si layer 151. In other words, through etching, the Si substrate 100 becomes the Si region 104a having the opening 104c formed therein. Through etching, the poly-Si layer 151 becomes a poly-Si region 151b having the opening 151a formed therein. Further, through etching, the opening 150a communicating to the openings 104c and 151c is formed in the SiO$_2$ layer 150. Then, the organic protective film applied to the surface 154b of the SiN layer 154 is removed through use of a solution that does not damage the SiN layer 152, for example, acetone.

With this, the center region C having a region defined by the poly-Si region 151b is formed. Through manufacturing of the center region C with the dimensions used in the fifth embodiment, the center region C becomes a region of from about 50 micrometers to about 100 micrometers square. In the rear surface Si etching process, when the Si substrate 100 is etched from the rear surface 100d side under a state in which the etchant is held in contact only with the wafer rear surface side, it is not required to apply the organic protective film to the surface 154b of the SiN layer 154, and the number of processes can thus be reduced.

Figure 34:
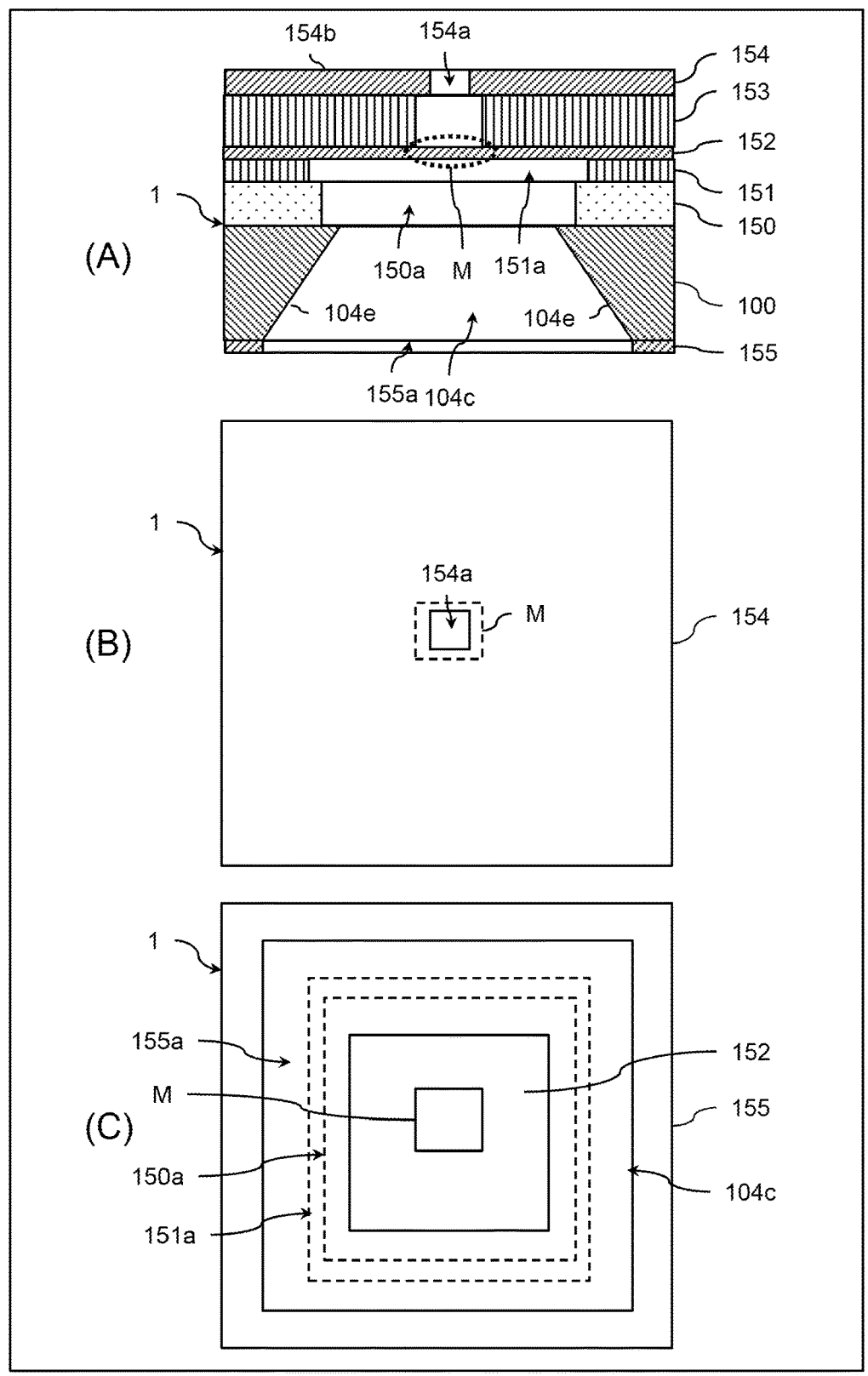
FIG. 34 is an explanatory view for illustrating a method (part 5) of manufacturing a membrane device according to the fifth embodiment.

FIG. 34 is an explanatory view for illustrating a method (part 5) of manufacturing a membrane device according to the fifth embodiment. The step of FIG. 34 includes etching a part of the poly-Si layer 153 obtained in the step of FIG. 33 with the SiN layer 154 being a mask through use of the KOH aqueous solution. With this, the membrane M having a region defined by the poly-Si layer 153 is formed to complete the membrane device 1. In consideration of variation in thickness of the poly-Si layer 153 and variation in etching rate by the KOH aqueous solution, it is preferred that etching in the step of FIG. 33 be performed for a long time period (that is, overetching be performed) as compared to a time period required for etching of the poly-Si layer 153 to a designed thickness. For example, it is preferred that overetching be performed so that the size of the membrane M extends to about a region of 500 nanometers×500 nanometers.

<Example of Forming Nanopore>

Figure 35:
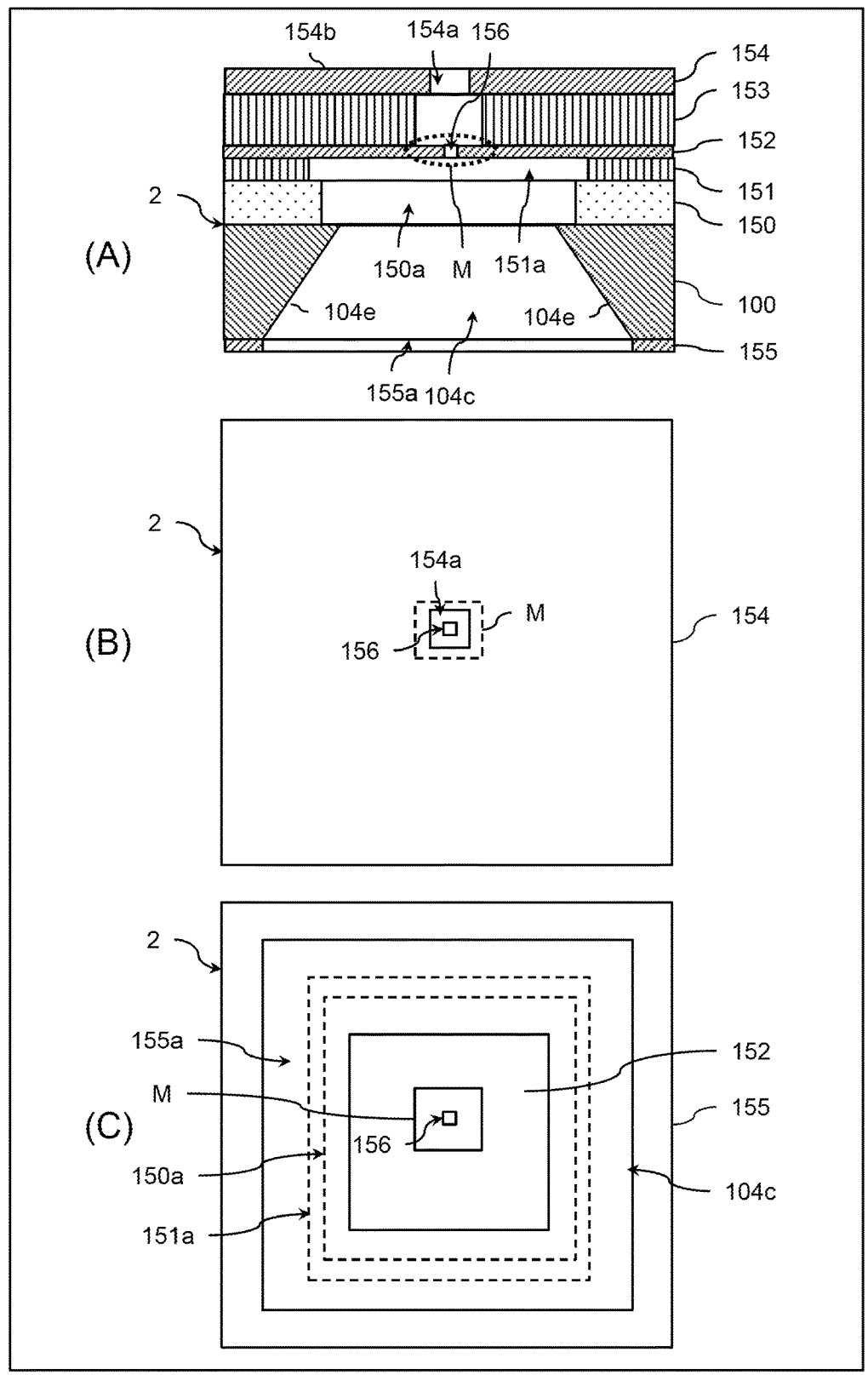
FIG. 35 is an explanatory view for illustrating an example of forming a nanopore in the membrane M in the fifth embodiment.

FIG. 35 is an explanatory view for illustrating an example of forming a nanopore in the membrane M in the fifth embodiment. The step of FIG. 35 includes forming a nanopore 156 in the membrane M through use of a known technology (electron beam irradiation process or puncture process) after forming the membrane M through the steps illustrated in FIG. 30 to FIG. 34. With this, the membrane device 1 becomes a nanopore device 2, and can measure an object to be measured that passes through the nanopore 156.

The manufacturing method according to the fifth embodiment enables formation of the membrane device 1 (nanopore device 2), in which the thickness of the SiO$_2$ layer 150 is large, that is, the electrostatic capacitance of the entire device is extremely small, and which has the small membrane M of a region of about 500 nanometers×about 500 nanometers. When the electrostatic capacitance of the entire device becomes low, noise at a time of measurement of ion current flowing when the DNA 110 passes through the nanopore 156 can also be reduced. Further, when the membrane M is reduced in size, there is a decreased probability that inevitable defects (a weak spot and a pinhole caused by, for example, a binding defect between atoms) occurring at a time of formation of the membrane M are present in the membrane M. Thus, the yield of the membrane M is improved.

Further, the nanopore device 2 manufactured by the manufacturing method according to the fifth embodiment can also be applied with the active drive system illustrated in FIG. 7 or FIG. 8. The poly-Si layer 153 and the SiN layer 154 are formed on the membrane M, but the total thickness of those layers is 250 nanometers in the fifth embodiment, which is not so large. Therefore, DNA sequencing can be performed under a state in which the DNA 110 is introduced into the nanopore 156 up to a portion of the DNA 110 fixed to the probe substrate 111, which is close to the fixed end 110a.

When the $SiO_2$ layer 150 having a thickness of from 1 micrometer to 20 micrometers in the fifth embodiment is formed on the membrane M, a region having a length of from at least 1 micrometer to at least 20 micrometers from the fixed end 110a of the DNA 110 fixed to the probe substrate 111 cannot be subjected to DNA sequencing by the active drive system. The membrane device 1 according to the fifth embodiment has a structure in which the $SiO_2$ layer 150 having a thickness of from 1 micrometer to 20 micrometers is formed below the membrane M, and only a laminated structure (poly-Si layer 153 and SiN layer 154) required for narrowing the region of the membrane M is formed above the membrane M. This structure is useful for reducing noise of a measurement current at a time of DNA sequencing in the active drive system.

Advantageous points of the manufacturing method according to the fifth embodiment are described below. In the manufacturing method according to the fifth embodiment, the etching rate of the $SiO_2$ layer 150 by the KOH or TMAH solution is lower than that of the Si substrate 100. Therefore, when the Si substrate 100 is etched with the KOH or TMAH solution, the thick $SiO_2$ layer 150 serves as an etching stopper. Further, the etching rate of the poly-Si layer 151 by hydrofluoric acid (HF) or buffered hydrofluoric acid (BHF) is lower than that of the $SiO_2$ layer 150. Thus, when the $SiO_2$ layer 150 is etched with hydrofluoric acid (HF) or buffered hydrofluoric acid (BHF), the poly-Si layer 151 serves as an etching stopper.

Therefore, when the poly-Si layer 151 (with a thickness of 100 nanometers in the fifth embodiment), which is thinner than the Si substrate 100 (with a thickness of 725 micrometers in the fifth embodiment), is etched after the $SiO_2$ layer 150 is etched, one surface of the membrane M having a region defined by the poly-Si layer 151 can be exposed. The poly-Si layer 151 is thinner than the Si substrate 100, and hence the overetching amount at a time of etching of the poly-Si layer 151 can also be reduced.

It is assumed that the thickness of the poly-Si layer 151 is set to 100 nanometers as in the fifth embodiment. In consideration of variation in etching speed within a wafer surface and variation in thickness of the poly-Si layer 151, etching is performed under a condition that enables the poly-Si layer 151 having a thickness of about 150 nanometers to be normally etched. With this, the poly-Si layer 151 (with a thickness of 100 nanometers) can be etched stably with less etching residue within a wafer surface. In other words, etching can be performed stably by overetching corresponding to 50% of the designed thickness of the poly-Si layer 151.

Meanwhile, in the method of the first embodiment, the second embodiment, Non Patent Literature 1, or Non Patent Literature 2, the Si substrate is etched without an etching stopper being formed along the path, to thereby expose a one-side portion of a thin film membrane. In this case, the overetching amount for performing etching stably without Si etching residue is required to be larger than that in the fifth embodiment. This is because the thickness of the Si substrate is, for example, normally 725 micrometers in an eight-inch wafer, and both variation in thickness within one wafer surface and variation in thickness between different wafers are as large as about several micrometers. Therefore, unless the overetching amount at a time of etching of the Si substrate is set to be larger than that in the fifth embodiment, etching cannot be stably performed without Si etching residue.

Further, in order to etch the Si substrate having a thickness of 725 micrometers, long-time etching (from about 8 hours to about 9 hours at 85° C. with the TMAH solution or the KOH aqueous solution) is required. Therefore, variation in Si etching completion time within a wafer surface, which is caused by variation in etching speed within a wafer surface, is also large. For this reason, unless the overetching amount is set to be larger than that in the fifth embodiment, etching cannot be performed stably without Si etching residue within the wafer surface.

From the foregoing, when the Si substrate is etched without an etching stopper being formed along the path as in the related-art examples (Non Patent Literature 1 and Non Patent Literature 2), unless at least overetching of from about 50 micrometers to about 100 micrometers is performed, etching cannot be performed stably without Si etching residue. The damage of the SiN film caused by the TMAH solution or the KOH aqueous solution is small, but is not zero. Therefore, as the overetching amount at a time of etching of the Si substrate increases, the probability that the SiN film to be a membrane is damaged increases. As a result, the foregoing causes an initial defect or the like of the membrane, and is a factor for decreasing the yield of the membrane to be manufactured.

In contrast, in the fifth embodiment, the $SiO_2$ layer 150 serving as an etching stopper is sandwiched between the Si substrate 100 and the poly-Si layer 151. Therefore, the overetching amount required at a time of final Si etching can be reduced to 1 micrometer or less. Thus, the probability that the membrane M is damaged can be reduced. As a result, the initial defect of the membrane M is reduced, and the yield of the membrane M to be manufactured can be improved.

Further, unlike Non Patent Literature 3, in the fifth embodiment, the membrane M is formed on the poly-Si layer 151 by film formation instead of the fishing method. Therefore, the membrane M has excellent flatness and less defects. Further, the process is simple, and a standard semiconductor process using the Si substrate 100 is used as the process. Therefore, the fifth embodiment is excellent in mass productivity. Further, in the fifth embodiment, the exposed surface of the $SiO_2$ layer 150 is smaller than that in Non Patent Literature 3. It is known that the DNA 110 is well adsorbed to $SiO_2$. However, in the fifth embodiment, the exposed surface of the $SiO_2$ layer 150 is small, and hence the amount of the DNA 110 to be measured that is adsorbed to the $SiO_2$ layer 150, is also small. A phenomenon in which the DNA 110 is adsorbed to the surface of the $SiO_2$ layer 150 and peels therefrom causes noise at a time of measurement of ion current flowing when the DNA 110 passes through the nanopore 156. Thus, the structure in which the exposed surface of the SiO$_2$ layer 150 is small as in the fifth embodiment is advantageous from the viewpoint of reducing noise at a time of current measurement.

A SiO$_2$ layer can also be used instead of the poly-Si layer 153. The thickness of the SiO$_2$ layer is set to, for example, 150 nanometers. The SiO$_2$ layer can be etched with the KOH aqueous solution at a high temperature (from 50° C. to 100° C.). Meanwhile, the SiN layer 152 is hardly damaged even by the KOH aqueous solution at a high temperature (from 50° C. to 100° C.). Therefore, the membrane M can be formed stably. Thus, through use of the SiO$_2$ layer instead of the poly-Si layer 153, the electrostatic capacitance of the membrane device 1 sandwiched between the aqueous solutions of the upper and lower chambers is further decreased at a time of measurement. Accordingly, noise at a time of measurement can be further reduced.

The insulation layer 155 may be made of a material other than that described in the fifth embodiment as long as the material is less liable to be scraped at a time of TMAH or KOH etching. For example, in the above-mentioned example, the insulation layer 155 is formed of the SiN layer, but may be formed of a SiO$_2$ layer. In other words, it is only required that the insulation layer 155 be made of such a material that the etching rate of the insulation layer 155 by TMAH or KOH etching is sufficiently low as compared to the etching rate of Si by TMAH or KOH etching. Further, it is only required that the membrane M be made of a material that is hardly damaged at a time of TMAH or KOH etching. For example, HfO$_2$ or HfAlO may be used instead of SiN.

When the Si substrate 100 or the poly-Si layer 151 is etched, an aqueous solution other than the TMAH solution or the KOH aqueous solution may be used. For example, it is only required that the aqueous solution be an alkaline aqueous solution that enables crystal anisotropy etching of Si, hardly damages the membrane M, and achieves an etching rate of the SiO$_2$ layer 150 and the insulation layer 155 sufficiently lower than that of Si.

The membrane device 1 formed by the manufacturing method described in the fifth embodiment has a feature in its finished shape. Specifically, for example, the inner peripheral surface 104e of the Si substrate 100 being a {111} plane is exposed, and the SiO$_2$ layer 150 is sandwiched between the Si substrate 100 and the poly-Si layer 151. Further, for example, the opening 151a of the poly-Si layer 151 is larger than the opening 150a of the SiO$_2$ layer 150.

As described above, through use of the manufacturing method according to the fifth embodiment, the membrane M can be formed stably with satisfactory yield. Further, after the nanopore 156 is formed in the membrane M, noise at a time of measurement of ion current flowing when the DNA 110 passes through the nanopore 156 can also be reduced. Further, the membrane device 1 (nanopore device 2), which is also suitable for being applied with the active drive system at a time of DNA sequencing, can be formed.

Sixth Embodiment

In a sixth embodiment of this invention, description is given of another manufacturing method exhibiting effects substantially equal to those of the fourth embodiment. In the fourth embodiment, the SOI substrate 10 is used, but in the sixth embodiment, the manufacturing method using the Si substrate 100 is described. The Si substrate 100 is more inexpensive than the SOI substrate 10, and hence cost of the membrane device 1 can be reduced.

Figure 36:
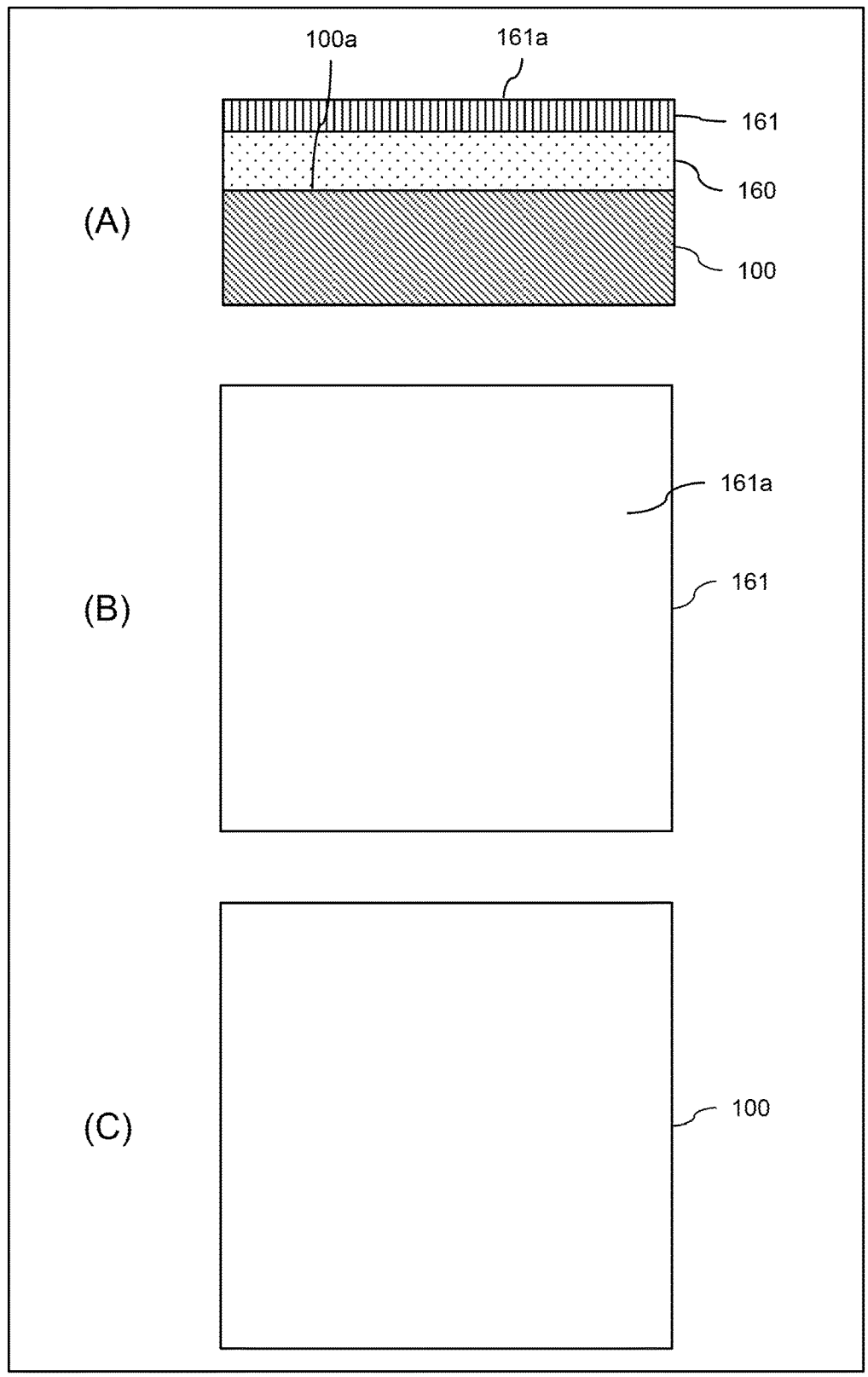
FIG. 36 is an explanatory view for illustrating a method (part 1) of manufacturing a membrane device according to the sixth embodiment.

FIG. 36 is an explanatory view for illustrating a method (part 1) of manufacturing a membrane device according to the sixth embodiment. In FIG. 36, the Si substrate 100 having a surface 100a of a plane direction {100} is prepared. The step of FIG. 36 includes depositing a SiO$_2$ layer 160, which is an insulation layer, to a thickness of from 1 micrometer to 20 micrometers on the Si substrate 100, and depositing a poly-Si layer 161 on the SiO$_2$ layer 160. The thickness of the poly-Si layer 161 is set to, for example, 100 nanometers.

Figure 37:
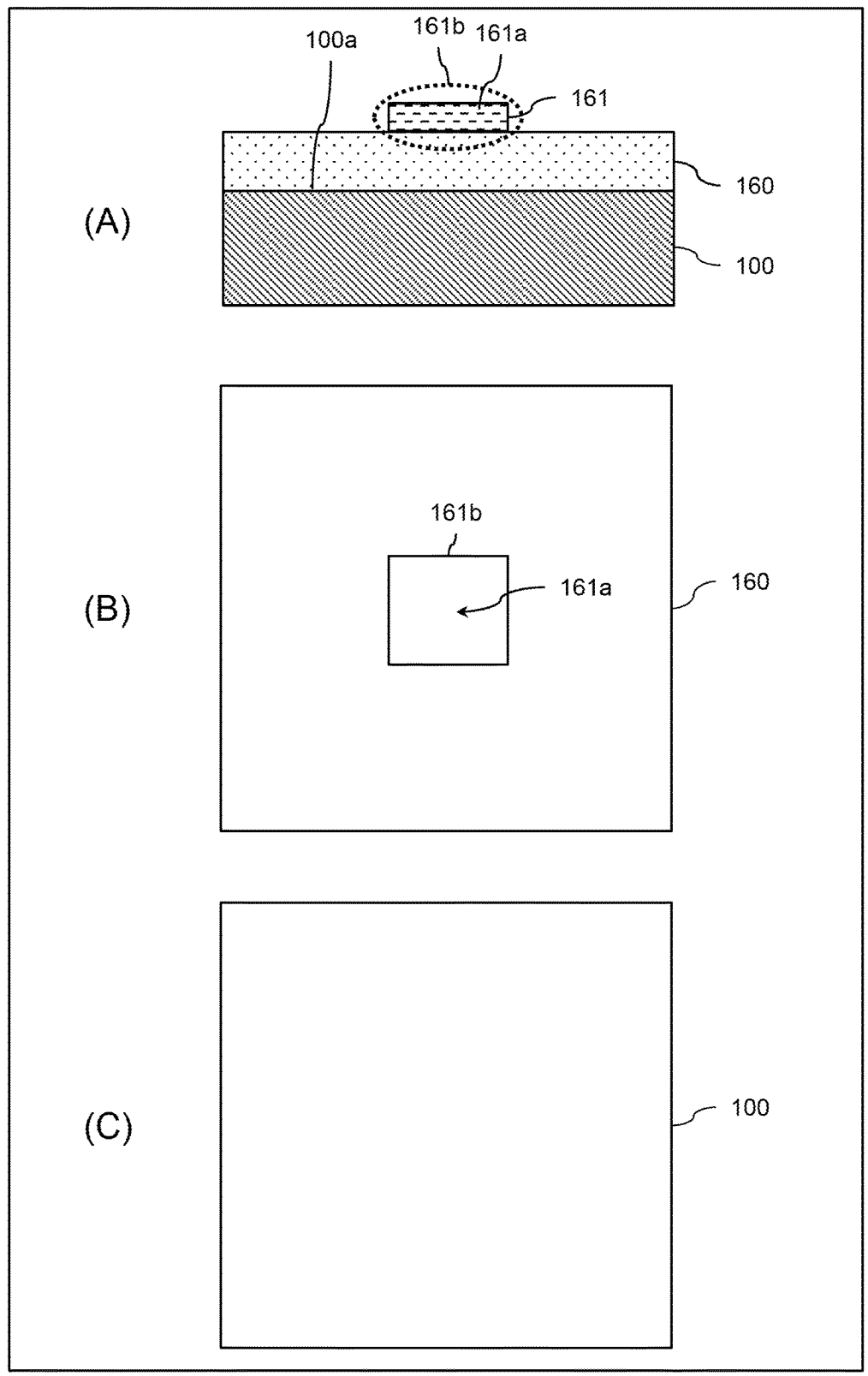
FIG. 37 is an explanatory view for illustrating a method (part 2) of manufacturing a membrane device according to the sixth embodiment.

FIG. 37 is an explanatory view for illustrating a method (part 2) of manufacturing a membrane device according to the sixth embodiment. The step of FIG. 37 includes patterning the poly-Si layer 161 formed on the Si substrate 100 obtained in FIG. 36 by dry etching, to thereby form an island pattern 161b of poly-Si. It is assumed that a region of the island pattern 161b of poly-Si has, for example, a vertical dimension of 3 micrometers and a horizontal dimension of 3 micrometers.

Figure 38:
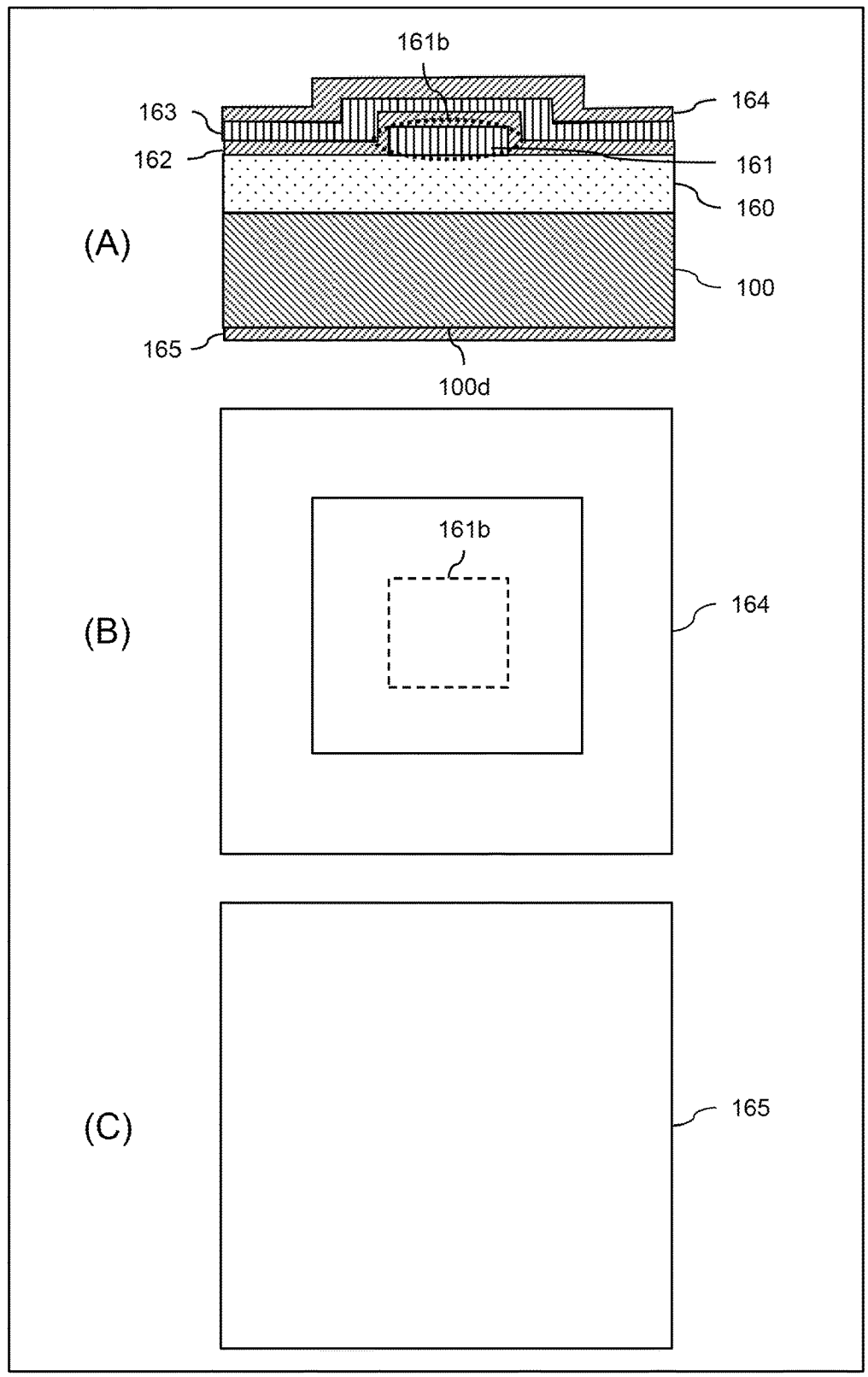
FIG. 38 is an explanatory view for illustrating a method (part 3) of manufacturing a membrane device according to the sixth embodiment.

FIG. 38 is an explanatory view for illustrating a method (part 3) of manufacturing a membrane device according to the sixth embodiment. The step of FIG. 38 includes depositing a SiN layer 162 on the SiO$_2$ layer 160 and the island pattern 161b formed on the Si substrate 100 obtained in the step of FIG. 37. The thickness of the SiN layer 162 is set to, for example, 3 nanometers. A poly-Si layer 163 and a SiN layer 164 are deposited on the SiN layer 162. The thickness of the poly-Si layer 163 is set to, for example, 150 nanometers, and the thickness of the SiN layer 164 is set to, for example, 100 nanometers. Further, an insulation layer 165 is deposited on the rear surface 100d of the Si substrate 100. The thickness of the insulation layer 165 is set to, for example, 100 nanometers.

Figure 39:
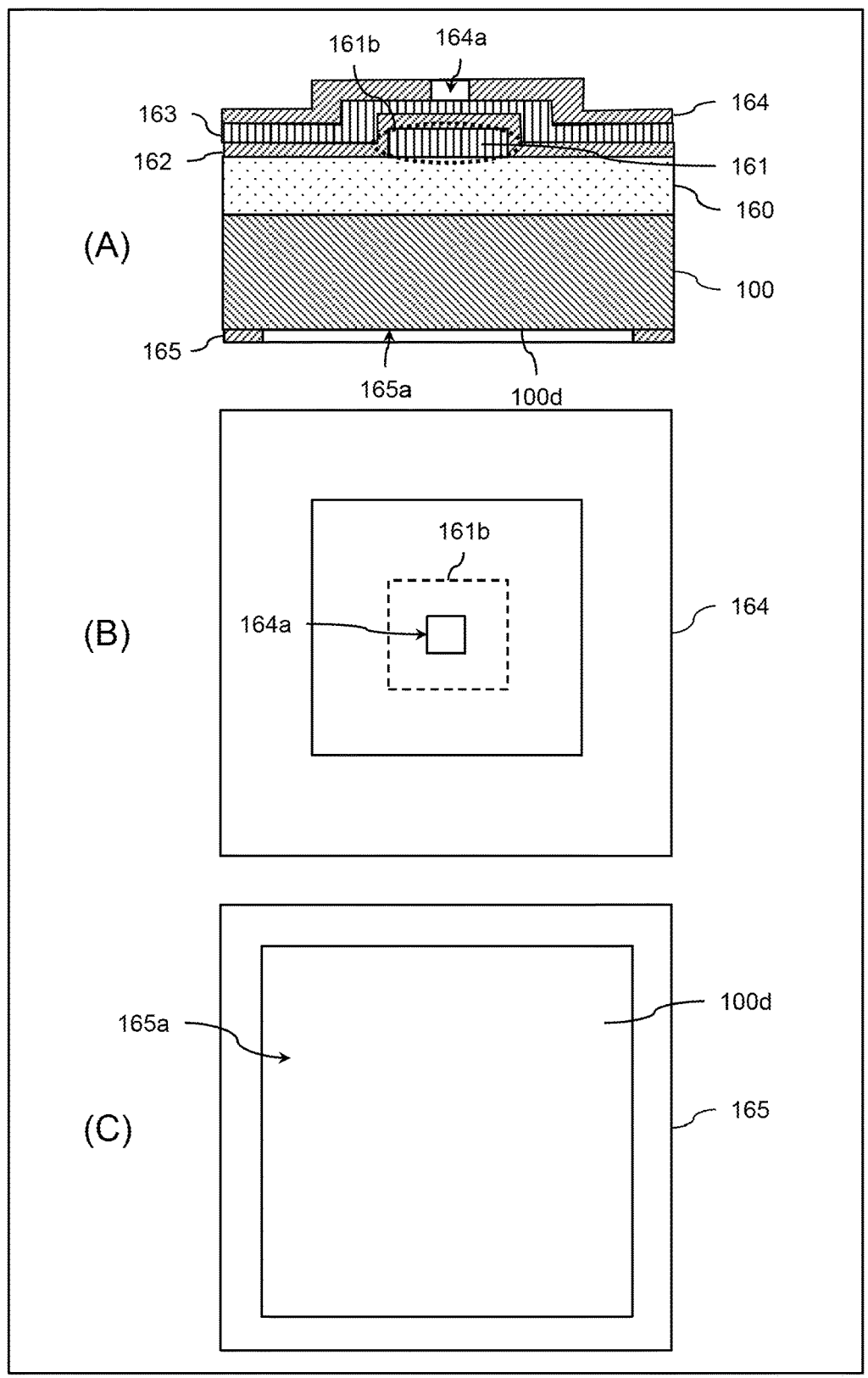
FIG. 39 is an explanatory view for illustrating a method (part 4) of manufacturing a membrane device according to the sixth embodiment.

FIG. 39 is an explanatory view for illustrating a method (part 4) of manufacturing a membrane device according to the sixth embodiment. The step of FIG. 39 includes opening a part of the SiN layer 164 obtained in the step of FIG. 38 through use of a lithography technology and a dry etching technology. An opening 164a is a rectangular region having an area of, for example, 100 nanometers×100 nanometers.

Further, the step of FIG. 39 includes patterning the insulation layer 165 on the rear surface 100d side of the Si substrate 100 through use of the general semiconductor lithography technology and dry etching technology as illustrated in parts (A) and (C) of FIG. 39. With this, Si is exposed from a partial region (patterned region 165a) of the rear surface 100d of the Si substrate 100. It is preferred that the size of the patterned region 165a, from which Si is exposed, be adjusted in accordance with the thickness of the Si substrate 100. For example, when the Si substrate 100 having a thickness of 725 micrometers is used, it is preferred that a region having, for example, a vertical dimension of 1,038 micrometers and a horizontal dimension of 1,038 micrometers be patterned as the patterned region 165a. The shape of the patterned region 165a is not limited to a square, and may be another polygon.

Figure 40:
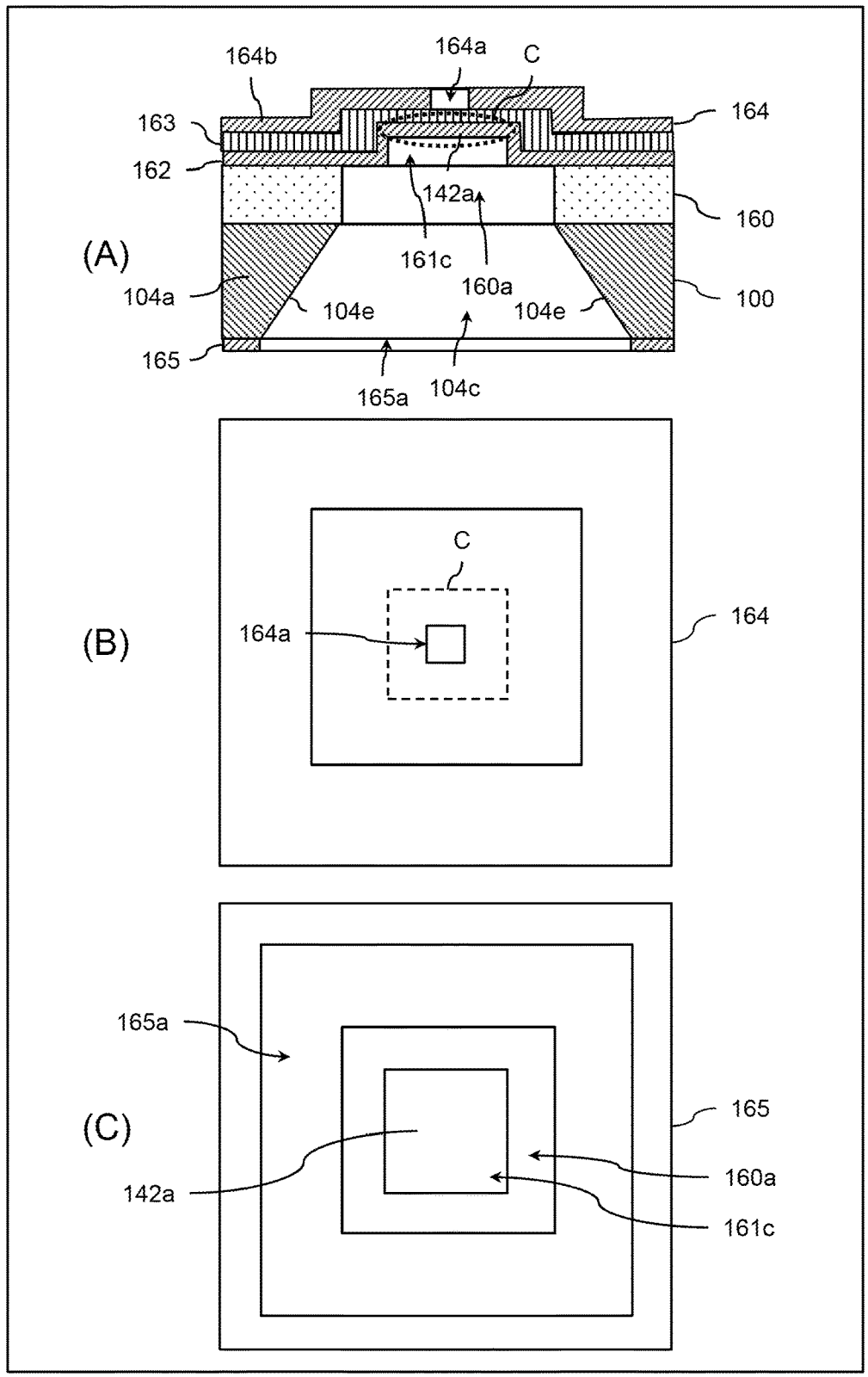
FIG. 40 is an explanatory view for illustrating a method (part 5) of manufacturing a membrane device according to the sixth embodiment.

FIG. 40 is an explanatory view for illustrating a method (part 5) of manufacturing a membrane device according to the sixth embodiment. The step of FIG. 40 includes applying an organic protective film (not shown) (for example, Pro-TEK B3 primer and ProTEK B3 manufactured by Brewer Science, Inc. are used) to a surface 164b of the SiN layer 164 obtained in the step of FIG. 39, and then etching the Si substrate 100 with a TMAH solution or a KOH aqueous solution from the rear surface 100d side.

After the Si substrate 100 is etched, the SiO₂ layer 160 is etched through use of, for example, hydrofluoric acid (HF) or buffered hydrofluoric acid (BHF). After the SiO₂ layer 160 is etched, the poly-Si layer 161 is etched with the TMAH solution or the KOH aqueous solution. Then, as illustrated in part (A) of FIG. 40, a tapered opening 104c, in which the inner peripheral surface 104e of the Si substrate 100 is exposed, is formed. In other words, through etching, the Si substrate 100 becomes the Si region 104a having the opening 104c formed therein. The inner peripheral surfaces 104e is a {111} plane.

Through etching, openings 160a and 161c are formed in the SiO₂ layer 160 and the poly-Si layer 161, respectively.

Then, the organic protective film applied to the surface 164b of the SiN layer 164 is removed through use of a solution that does not damage the SiN layer 164, for example, acetone.

With this, the center region C having a region defined by the poly-Si layer 161 is formed. Through manufacturing of the center region C with the dimensions used in the sixth embodiment, the center region C becomes a region of from about 2 micrometers to about 3 micrometers square. In the rear surface Si etching process, when the Si substrate 100 is etched from the rear surface 100d side under a state in which the etchant is held in contact only with the wafer rear surface side, it is not required to apply the organic protective film to the surface 164b of the SiN layer 164, and the number of processes can be thus reduced.

Figure 41:
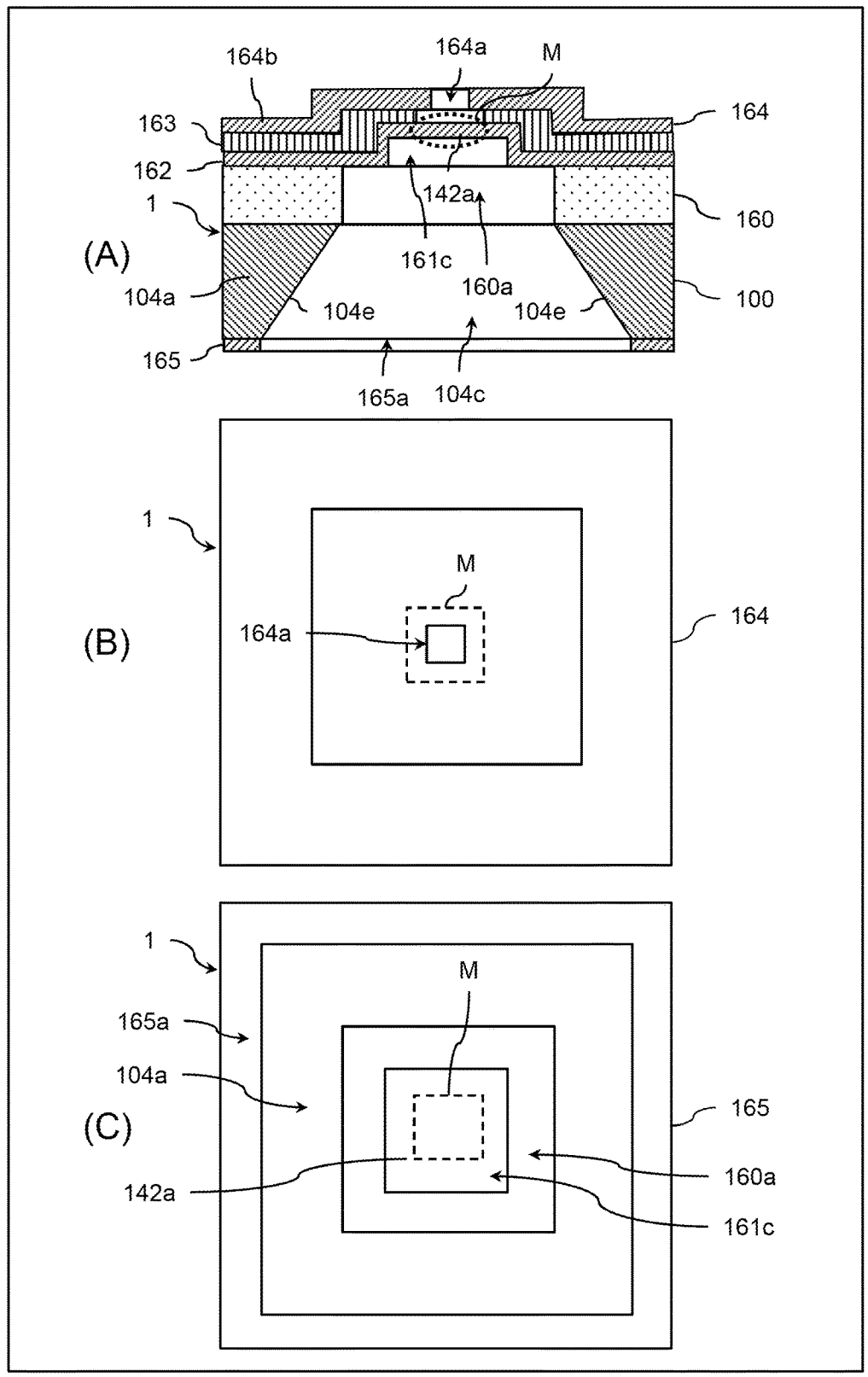
FIG. 41 is an explanatory view for illustrating a method (part 6) of manufacturing a membrane device according to the sixth embodiment.

FIG. 41 is an explanatory view for illustrating a method (part 6) of manufacturing a membrane device according to the sixth embodiment. The step of FIG. 41 includes etching a part of the poly-Si layer 163 obtained in the step of FIG. 40 with the SiN layer 164 being a mask through use of the KOH aqueous solution. With this, the membrane M having a region defined by the poly-Si layer 163 is formed to complete the membrane device 1. In consideration of variation in thickness of the poly-Si layer 163 and variation in etching rate by the KOH aqueous solution, it is preferred that etching in the step of FIG. 41 be performed for a long time period (that is, overetching be performed) as compared to a time period required for etching of the poly-Si layer 163 to a designed thickness. For example, it is preferred that overetching be performed so that the size of the membrane M extends to about a region of 500 nanometers×500 nanometers.

<Example of Forming Nanopore>

Figure 42:
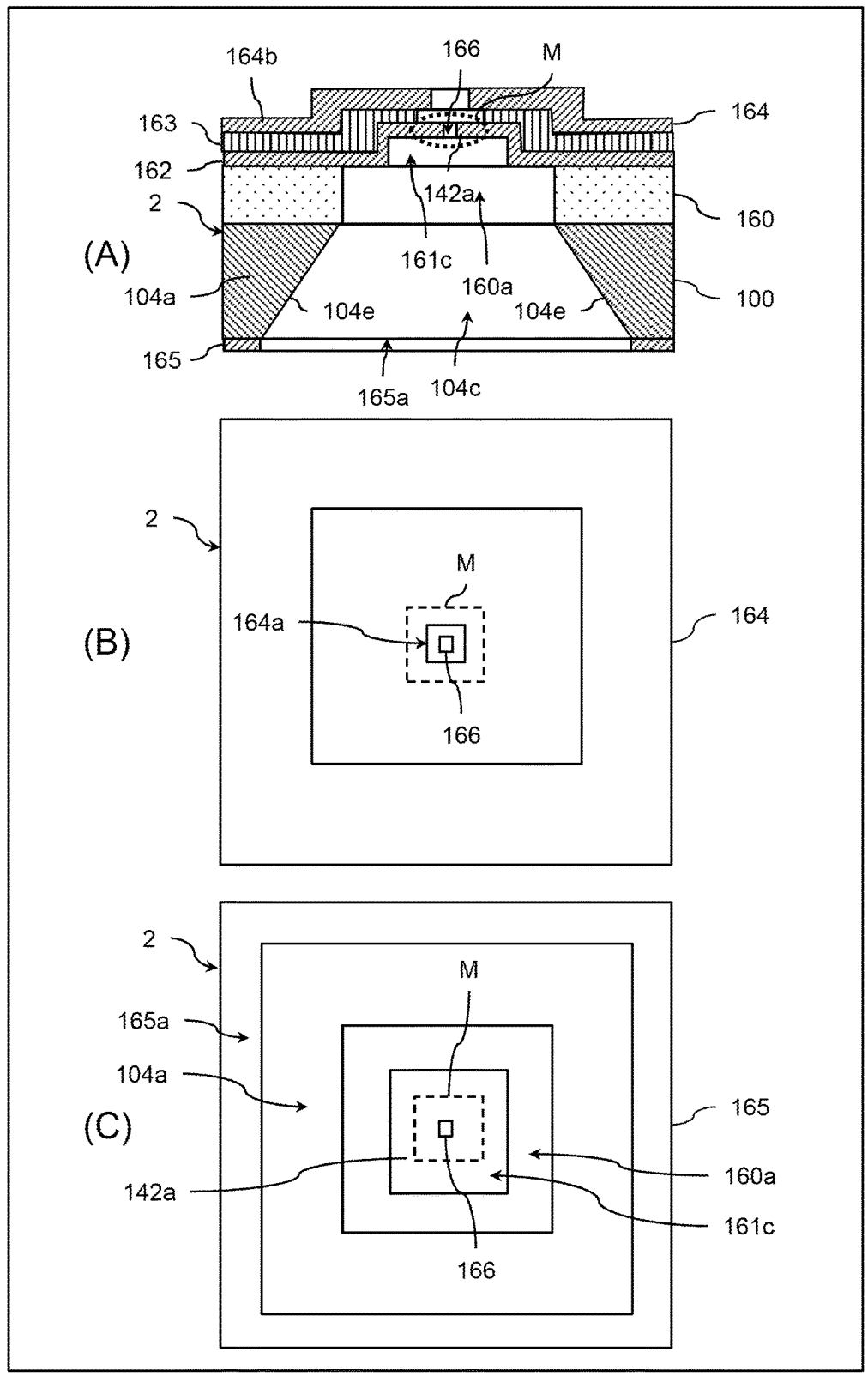
FIG. 42 is an explanatory view for illustrating an example of forming a nanopore in the membrane M in the sixth embodiment.

FIG. 42 is an explanatory view for illustrating an example of forming a nanopore in the membrane M in the sixth embodiment. The step of FIG. 42 includes forming a nanopore 166 in the membrane M through use of a known technology (electron beam irradiation process or puncture process) after forming the membrane M through the steps illustrated in FIG. 36 to FIG. 41. With this, the membrane device 1 becomes a nanopore device 2, and can measure an object to be measured that passes through the nanopore 166.

The manufacturing method according to the sixth embodiment enables formation of the membrane device 1 (nanopore device 2), in which the thickness of the SiO₂ layer 160 is large, that is, the electrostatic capacitance of the entire device is extremely small, and which has the small membrane M of a region of about 500 nanometers×about 500 nanometers. When the electrostatic capacitance of the entire device becomes low, noise at a time of measurement of ion current flowing when the DNA 110 passes through the nanopore 166 can also be reduced. Further, when the membrane M is reduced in size, there is a decreased probability that inevitable defects (a weak spot and a pinhole caused by, for example, a binding defect between atoms) occurring at a time of formation of the membrane M are present in the membrane M. Thus, the yield of the membrane M is improved.

Further, the nanopore device 2 manufactured by the manufacturing method according to the sixth embodiment can also be applied with the active drive system illustrated in FIG. 7 or FIG. 8. The poly-Si layer 163 and the SiN layer 164 are formed on the membrane M, but the total thickness of those layers is 250 nanometers in the sixth embodiment, which is not so large. Therefore, DNA sequencing can be performed under a state in which the DNA 110 is introduced into the nanopore 166 up to a portion of the DNA 110 fixed to the probe substrate 111, which is close to the fixed end 110a.

When the SiO₂ layer 160 having a thickness of from 1 micrometer to 20 micrometers in the sixth embodiment is formed on the membrane M, a region having a length of from at least 1 micrometer to at least 20 micrometers from the fixed end 110a of the DNA 110 fixed to the probe substrate 111 cannot be subjected to DNA sequencing by the active drive system. The membrane device 1 according to the sixth embodiment has a structure in which the SiO₂ layer 160 having a thickness of from 1 micrometer to 20 micrometers is formed below the membrane M, and only a laminated structure (poly-Si layer 163 and SiN layer 164) required for narrowing the region of the membrane M is formed above the membrane M. This structure is useful for reducing noise of a measurement current at a time of DNA sequencing in the active drive system.

Further, as compared to the nanopore device 2 illustrated in FIG. 35, which is described in the sixth embodiment, in the nanopore device 2 manufactured by the manufacturing method according to the fifth embodiment, the poly-Si layer 161 is not present when the nanopore device 2 is completed. Therefore, the electrostatic capacitance between the aqueous solutions filled into both sides of the nanopore device 2 (that is, the electrostatic capacitance of the nanopore device 2) becomes lower than that of the device described in the fifth embodiment. As a result, noise at a time of measurement of ion current flowing when the DNA 110 passes through the nanopore 166 also further decreases.

Advantageous points of the manufacturing method according to the sixth embodiment are described below. As in the fifth embodiment, in the manufacturing method according to the sixth embodiment, the etching rate of the SiO₂ layer by the KOH or TMAH solution is lower than that of the Si substrate 100. When the Si substrate 100 is etched with the KOH or TMAH solution, the thick SiO₂ layer 160 serves as an etching stopper. Further, the etching rate of the poly-Si layer 161 by hydrofluoric acid (HF) or buffered hydrofluoric acid (BHF) is lower than that of the SiO₂ layer 160. When the SiO₂ layer 160 is etched with hydrofluoric acid (HF) or buffered hydrofluoric acid (BHF), the poly-Si layer 161 serves as an etching stopper.

Therefore, when the poly-Si layer 161 (with a thickness of 100 nanometers in the sixth embodiment), which is thinner than the Si substrate 100 (with a thickness of 725 micrometers in the sixth embodiment), is etched after the SiO₂ layer 160 is etched, one surface of the membrane M can be exposed. The Si single crystal layer 161 is thinner than the Si substrate 100, and hence the overetching amount at a time of etching of the poly-Si layer 161 can also be reduced.

It is assumed that the thickness of the poly-Si layer 161 is set to 100 nanometers as in the sixth embodiment. In consideration of variation in etching speed within a wafer surface and variation in thickness of the poly-Si layer 161, etching is performed under a condition that enables the poly-Si layer 161 having a thickness of about 150 nanometers to be normally etched. With this, the poly-Si layer 161 (with a thickness of 100 nanometers) can be etched stably with less etching residue within a wafer surface. In other words, etching can be performed stably by overetching corresponding to 50% of the designed thickness of the poly-Si layer 161.

Meanwhile, in the method of the first embodiment, the second embodiment, Non Patent Literature 1, or Non Patent Literature 2, the Si substrate is etched without an etching stopper being formed along the path, to thereby expose a one-side portion of a thin film membrane. In this case, the overetching amount for performing etching stably without Si etching residue is required to be larger than that in the sixth embodiment. This is because the thickness of the Si substrate is, for example, normally 725 micrometers in an eight-inch wafer, and both variation in thickness within one wafer surface and variation in thickness between different wafers are as large as about several micrometers. Therefore, unless the overetching amount at a time of etching of the Si substrate is set to be larger than that in the sixth embodiment, etching cannot be stably performed without Si etching residue.

Further, in order to etch the Si substrate having a thickness of 725 micrometers, long-time etching (from about 8 hours to about 9 hours at 85° C. with the TMAH solution or the KOH aqueous solution) is required. Therefore, variation in Si etching completion time within a wafer surface, which is caused by variation in etching speed within a wafer surface, is also large. For this reason, unless the overetching amount is set to be larger than that in the sixth embodiment, etching cannot be performed stably without Si etching residue within the wafer surface.

From the foregoing, when the Si substrate is etched without an etching stopper being formed along the path as in the related-art examples (Non Patent Literature 1 and Non Patent Literature 2), unless at least overetching of from about 50 micrometers to about 100 micrometers is performed, etching cannot be performed stably without Si etching residue. The damage of the SiN film caused by the TMAH solution or the KOH aqueous solution is small, but is not zero. Therefore, as the overetching amount at a time of etching of the Si substrate increases, the probability that the SiN film to be a membrane is damaged increases. As a result, the foregoing causes an initial defect or the like of the membrane, and is a factor for decreasing the yield of the membrane to be manufactured.

In contrast, in the sixth embodiment, the $SiO_2$ layer 160 serving as an etching stopper is sandwiched between the Si substrate 100 and the poly-Si layer 161. Therefore, the overetching amount required at a time of final Si etching can be reduced to 1 micrometer or less. Thus, the probability that the membrane M having a region defined by the poly-Si layer 163 is damaged can be reduced. As a result, the initial defect of the membrane M having a region defined by the poly-Si layer 163 is reduced, and the yield of the membrane M to be manufactured can be improved.

Further, unlike Non Patent Literature 3, in the sixth embodiment, the membrane M is formed on the poly-Si layer 161 by film formation instead of the fishing method. Therefore, the membrane M has excellent flatness and less defects. Further, the process is simple, and a standard semiconductor process using a Si wafer is used as the process. Therefore, the sixth embodiment is excellent in mass productivity. Further, in the sixth embodiment, the exposed surface of the $SiO_2$ layer 160 is smaller than that in Non Patent Literature 3. It is known that the DNA 110 is well adsorbed to $SiO_2$. However, in the sixth embodiment, the exposed surface of the $SiO_2$ layer 160 is small, and hence the amount of the DNA 110 to be measured that is adsorbed to the $SiO_2$ layer 160, is also small. A phenomenon in which the DNA 110 is adsorbed to the surface of the $SiO_2$ layer 160 and peels therefrom causes noise at a time of measurement of ion current flowing when the DNA 110 passes through the nanopore 166. Thus, the structure in which the exposed surface of the $SiO_2$ layer 160 is small as in the sixth embodiment is advantageous from the viewpoint of reducing noise at a time of current measurement.

A $SiO_2$ layer can also be used instead of the poly-Si layer 163. The thickness of the $SiO_2$ layer is set to, for example, 150 nanometers. The $SiO_2$ layer can be etched with the KOH aqueous solution at a high temperature (from 50° C. to 100° C.). Meanwhile, the SiN layer 162 is hardly damaged even by the KOH aqueous solution at a high temperature (from 50° C. to 100° C.). Therefore, the membrane M can be formed stably. Thus, through use of the $SiO_2$ layer instead of the poly-Si layer 163, the electrostatic capacitance of the membrane device 1 sandwiched between the aqueous solutions of the upper and lower chambers is further decreased at a time of measurement. Accordingly, noise at a time of measurement can be further reduced.

The insulation layer 165 may be made of a material other than that described in the sixth embodiment as long as the material is less liable to be scraped at a time of TMAH or KOH etching. For example, in the above-mentioned example, the insulation layer 165 is formed of the SiN layer, but may be formed of a $SiO_2$ layer. In other words, it is only required that the insulation layer 165 be made of such a material that the etching rate of the insulation layer 165 by TMAH or KOH etching is sufficiently low as compared to the etching rate of Si by TMAH or KOH etching. Further, it is only required that the membrane M be made of a material that is hardly damaged at a time of TMAH or KOH etching. For example, $HfO_2$ or HfAlO may be used instead of SiN.

When the Si substrate 100 or the poly-Si layer 161 is etched, an aqueous solution other than the TMAH solution or the KOH aqueous solution may be used. For example, it is only required that the aqueous solution be an alkaline aqueous solution that enables crystal anisotropy etching of Si, hardly damages the membrane M, and achieves an etching rate of the $SiO_2$ layer 160 and the insulation layer 165 sufficiently lower than that of Si.

The membrane device 1 formed by the manufacturing method described in the sixth embodiment has a feature in its finished shape. Specifically, for example, the inner peripheral surface 104e of the Si substrate 100 being a {111} plane is exposed, and the $SiO_2$ layer 160 is sandwiched between the Si substrate 100 and the SiN layer 162.

Further, the poly-Si layer 161 does not remain when the device is completed.

As described above, through use of the manufacturing method according to the sixth embodiment, the membrane M can be formed stably with satisfactory yield. Further, after the nanopore 166 is formed in the membrane M, noise at a time of measurement of ion current flowing when the DNA 110 passes through the nanopore 166 can also be reduced. Further, the membrane device 1 (nanopore device 2), which is also suitable for application to the active drive system at a time of DNA sequencing, can be formed.

Seventh Embodiment

In a seventh embodiment of this invention, description is given of an example in which the nanopore device 2 is formed by performing the steps of FIG. 1 to FIG. 5 without depositing the SiN layer 102 in the manufacturing method according to the first embodiment.

Figure 43:
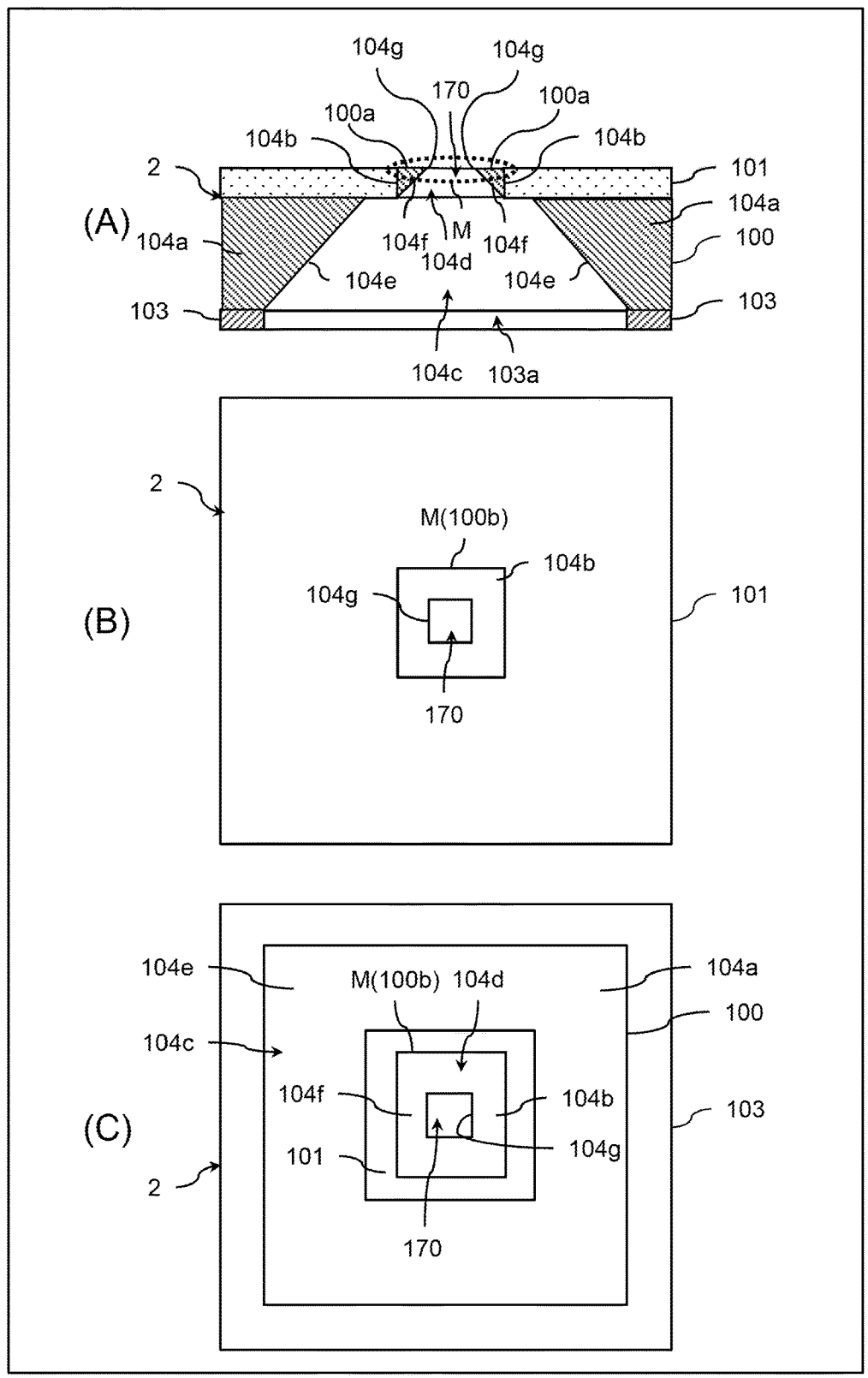
FIG. 43 is an explanatory view for illustrating an example of forming a nanopore device in the seventh embodiment.

FIG. 43 is an explanatory view for illustrating an example of forming a nanopore device in the seventh embodiment. The size of a nanopore 170 can be controlled by the size of the island pattern 100b of the Si substrate 100 formed in the step of FIG. 1 as described in the first embodiment. For example, in the step of FIG. 1, it is assumed that a vertical dimension of the island pattern 100b of Si is 100 nanometers, a horizontal dimension thereof is 100 nanometers, and the height thereof is from 60 nanometers to 70 nanometers. Through steps corresponding to those of FIG. 2 to FIG. 5, the nanopore (hole region) 170 is formed.

The nanopore 170 is formed on the surface 100a of the island pattern 100b, and hence has a peripheral edge 104g having an acute-angled shape. The nanopore 170 is a region having a vertical dimension and a horizontal dimension each being from about 1 nanometer to about 20 nanometers. In the seventh embodiment, the surface 100a of the island pattern 100b corresponds to the membrane M.

In other words, the fine nanopore 170 having a size equal to or smaller than that defined by the current lithography technology can be formed and used for measurement. Specifically, an aqueous solution is filled into upper and lower portions of the nanopore device 2 of FIG. 43, and an ion current flowing when the DNA passes through the nanopore 170 is measured. Then, based on a change in ion current that fluctuates at a time when an object to be measured, for example, the DNA 110, enters the nanopore 170, the characteristics and structural quantity of the object to be measured are observed.

The nanopore device 2 formed in the seventh embodiment has a feature in that the peripheral edge 104g defining the nanopore 170 is formed through use of anisotropic etching of Si, and hence is pointed. In other words, the plane direction of the surface 100a of the island pattern 100b viewed from an upper surface side of the nanopore device 2 is an exposed {100} plane. The plane direction of the inner peripheral surface 104e of the island pattern 100b viewed from a lower surface side of the nanopore device 2 is an exposed {111} plane.

As one of the important factors for determining DNA reading accuracy of the nanopore sequencer, there is given the thickness of the membrane M. Specifically, it is preferred that the thickness of the membrane M be as small as possible. The reason is as follows. Each interval between adjacent bases of four kinds of bases (A, G, C, and T) arranged in a DNA strand is about 0.34 nanometer. As the thickness of the membrane M becomes larger as compared to the interval, a larger number of bases simultaneously enter the nanopore.

Then, a signal obtained by current measurement is also a signal derived from a plurality of bases. Therefore, the determination accuracy of a base sequence is deteriorated, and signal analysis also becomes more complicated. Further, even when structural features of various biological molecules other than the DNA 110 are intended to be acquired, as the thickness of the membrane M becomes larger, spatial resolution decreases. Thus, in order to improve structure determination accuracy of an object to be measured, it is important to reduce the thickness of the membrane M having a nanopore to the extent possible.

In this respect, in the nanopore device 2 formed in the seventh embodiment, the nanopore 170 formed on the surface 100a of the island pattern 100b is defined by the acute peripheral edge 104g, and hence the substantial thickness of the membrane M in the vicinity of the nanopore 170 is as thin as about one atom. Therefore, in measurement of an object to be measured in the nanopore 170, the spatial resolution of measurement can be increased.

As described above, with each of the manufacturing methods according to the first to seventh embodiments, the device in which breakage of a membrane is suppressed and that includes a membrane having a low electrostatic capacitance can be manufactured. Further, in each of the devices manufactured in the first to seventh embodiments, noise at a time of measurement of an ion current flowing when the DNA passes through a nanopore formed in the membrane can be reduced. Thus, the structure determination accuracy of an object to be measured passing through the nanopore can be improved.

It should be noted that this invention is not limited to the above-mentioned embodiments, and encompasses various modification examples and the equivalent configurations within the scope of the appended claims without departing from the gist of this invention. For example, the above-mentioned embodiments are described in detail for a better understanding of this invention, and this invention is not necessarily limited to what includes all the configurations that have been described. Further, a part of the configurations according to a given embodiment may be replaced by the configurations according to another embodiment. Further, the configurations according to another embodiment may be added to the configurations according to a given embodiment. Further, a part of the configurations according to each embodiment may be added to, deleted from, or replaced by another configuration.

What is claimed is:

1. A method of manufacturing a membrane device, comprising:
    a first step of forming a pillar structure on a part of a Si substrate by etching;
    a second step of forming a first insulation layer on the Si substrate so as to expose a Si surface of an upper part of the pillar structure;
    a third step of forming a second insulation layer on the pillar structure and the first insulation layer; and
    a fourth step of etching the Si substrate from an opposite side of the second insulation layer and etching the pillar structure with the first insulation layer being a mask, to thereby form a membrane so that a part of the pillar structure remains outside of the membrane, which is a region free of the pillar structure and narrower than a width of the pillar structure orthogonal to the etching direction in the second insulation layer.

2. The method of manufacturing a membrane device according to claim 1,
    wherein the fourth step comprises using any one of a solution containing TMAH, a solution containing KOH, and an alkaline solution for the etching, and
    wherein etching rates of the first insulation layer and the second insulation layer performed by the any one of the solutions are each lower than an etching rate of the Si substrate.

3. The method of manufacturing a membrane device according to claim 2,
    wherein the third step comprises forming the second insulation layer through use of one of SiN, $HfO_2$, and HfAlO.

4. The method of manufacturing a membrane device according to claim 2,
    wherein the second step comprises forming the first insulation layer through use of one of $SiO_2$ and SiN.

5. The method of manufacturing a membrane device according to claim 1, wherein the first step comprises forming the pillar structure on the Si substrate so that the membrane has an area falling within a range of from 100 square nanometers to 250,000 square nanometers.

6. The method of manufacturing a membrane device according to claim 1,
wherein the second step comprises forming the first insulation layer so that the first insulation layer has a thickness falling within a range of from 100 nanometers to 20 micrometers.

7. The method of manufacturing a membrane device according to claim 1, further comprising:
a fifth step of, after the third step, forming an intermediate layer on the second insulation layer and forming a third insulation layer on the intermediate layer;
a sixth step of forming an opening in a region above the pillar structure in the third insulation layer formed in the fifth step; and
a seventh step of etching the intermediate layer from the opening formed in the sixth step to expose the second insulation layer,
wherein the fourth step comprises etching the Si substrate from an opposite side of the third insulation layer and the pillar structure with the first insulation layer being a mask, to thereby form, as the membrane, so that a part of the pillar structure remains outside of the membrane, a region free of the pillar structure and the intermediate layer narrower than a width of the pillar structure orthogonal to the etching direction in the second insulation layer.

8. The method of manufacturing a membrane device according to claim 7,
wherein the fifth step comprises forming the intermediate layer through use of one of poly-Si and $SiO_2$, and
wherein the seventh step comprises using any one of a solution containing TMAH, a solution containing KOH, and an alkaline solution for the etching of the intermediate layer.

* * * * *